US011185384B2

(12) United States Patent
Feinberg et al.

(10) Patent No.: US 11,185,384 B2
(45) Date of Patent: Nov. 30, 2021

(54) TISSUE EXPANDERS HAVING INTEGRATED DRAINAGE AND INFUSION ASSEMBLIES

(71) Applicant: Mentor Worldwide LLC, Irvine, CA (US)

(72) Inventors: Marc Feinberg, Ringoes, NJ (US); Leo B. Kriksunov, Ithaca, NY (US); Robert J. Tannhauser, Bridgewater, NJ (US); Michael Hoffman, Hillsborough, NJ (US); Jonathan Frenzel, Los Alamitos, CA (US)

(73) Assignee: Mentor Worldwide LLC, Irvine, CA (US)

( * ) Notice: Subject to any disclaimer, the term of this patent is extended or adjusted under 35 U.S.C. 154(b) by 82 days.

(21) Appl. No.: 16/662,751

(22) Filed: Oct. 24, 2019

(65) Prior Publication Data

US 2020/0129258 A1    Apr. 30, 2020

Related U.S. Application Data

(60) Provisional application No. 62/752,813, filed on Oct. 30, 2018.

(51) Int. Cl.
*A61B 90/00* (2016.01)
*A61F 2/12* (2006.01)
*A61F 2/30* (2006.01)

(52) U.S. Cl.
CPC .............. *A61B 90/02* (2016.02); *A61F 2/12* (2013.01); *A61F 2002/30691* (2013.01); *A61F 2250/0003* (2013.01)

(58) Field of Classification Search
CPC .......... A61B 90/02; A61B 2017/00792; A61B 2017/00796; A61B 2090/3925;
(Continued)

(56) References Cited

U.S. PATENT DOCUMENTS 4,398,910 A    8/1983  Blake et al.
4,429,693 A    2/1984  Blake et al.
(Continued)

FOREIGN PATENT DOCUMENTS

GB    2192338    1/1988

OTHER PUBLICATIONS

International Search Report issued in corresponding International Application No. PCT/IB2019/059228, dated Mar. 30, 2020, 7 pages.

(Continued)

*Primary Examiner* — Brian A Dukert
*Assistant Examiner* — Rebecca Lynee Zimmerman
(74) *Attorney, Agent, or Firm* — Doherty IP Law Group LLC

(57) ABSTRACT

A tissue expander having an integrated drain includes an outer shell having an opening and one or more drainage holes. An injection port is disposed in the opening of the shell and forms a fluid-tight seal with the shell. The injection port includes a needle guard having a needle guard base with a top surface, and a barrier membrane that overlies the top surface of the needle guard base. The barrier membrane defines an inflation chamber located between the top surface of the needle guard base and a bottom surface of the barrier membrane, and a drainage chamber overlying a top surface of the barrier membrane. The tissue expander includes one or more inflation ports that are in fluid communication with the inflation chamber for inflating and deflating the outer shell with a first fluid. A drainage conduit is in fluid communication with and extends between the drainage chamber and the one or more drainage holes for draining a second fluid from outside the shell.

24 Claims, 44 Drawing Sheets

(58) Field of Classification Search
CPC .............. A61F 2/12; A61F 2002/30691; A61F 2250/0003; A61F 2250/0067; A61M 2039/0205; A61M 2039/0226; A61M 2205/04; A61M 1/0001; A61M 39/0208
See application file for complete search history.

(56) References Cited

U.S. PATENT DOCUMENTS

| | | | |
|---|---|---|---|
| 5,630,843 | A | 5/1997 | Rosenberg |
| 6,544,214 | B1 | 4/2003 | Utterberg |
| 6,743,254 | B2 | 6/2004 | Guest et al. |
| 8,454,690 | B2 | 6/2013 | McClellan |
| 9,636,210 | B2 | 5/2017 | Hristov et al. |
| 9,700,404 | B2 | 7/2017 | Martin et al. |
| 2011/0153017 | A1* | 6/2011 | McClellan .............. A61B 90/02 623/8 |
| 2011/0160854 | A1 | 6/2011 | Berg et al. |
| 2014/0277440 | A1* | 9/2014 | Martin .................. A61B 90/02 623/8 |
| 2017/0035999 | A1 | 2/2017 | Wijay |
| 2017/0079737 | A1 | 3/2017 | Jones et al. |

OTHER PUBLICATIONS

International Search Report issued in related International Application No. PCT/IB2019/059230, dated Feb. 3, 2020, 6 pages.

* cited by examiner

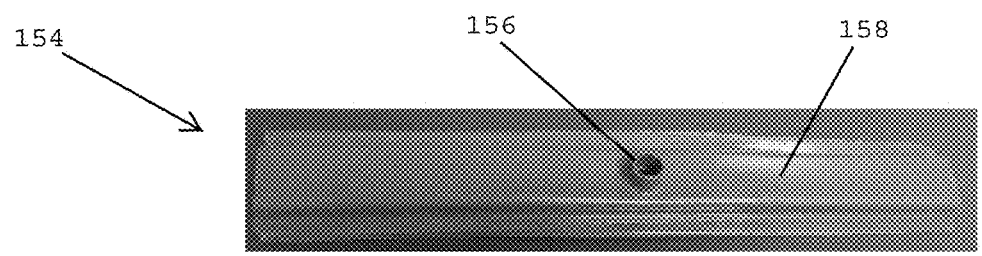
FIG. 5A
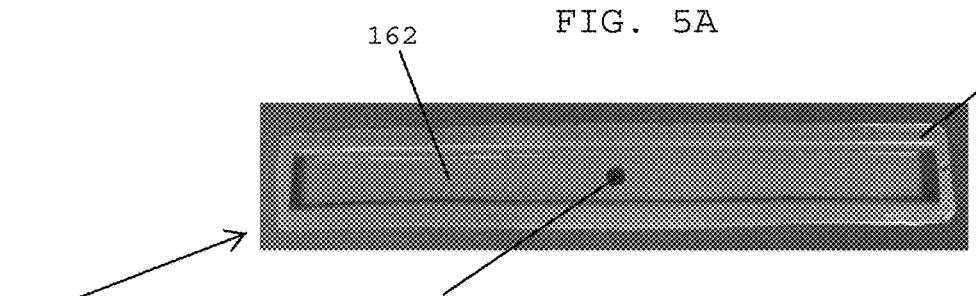
FIG. 5B
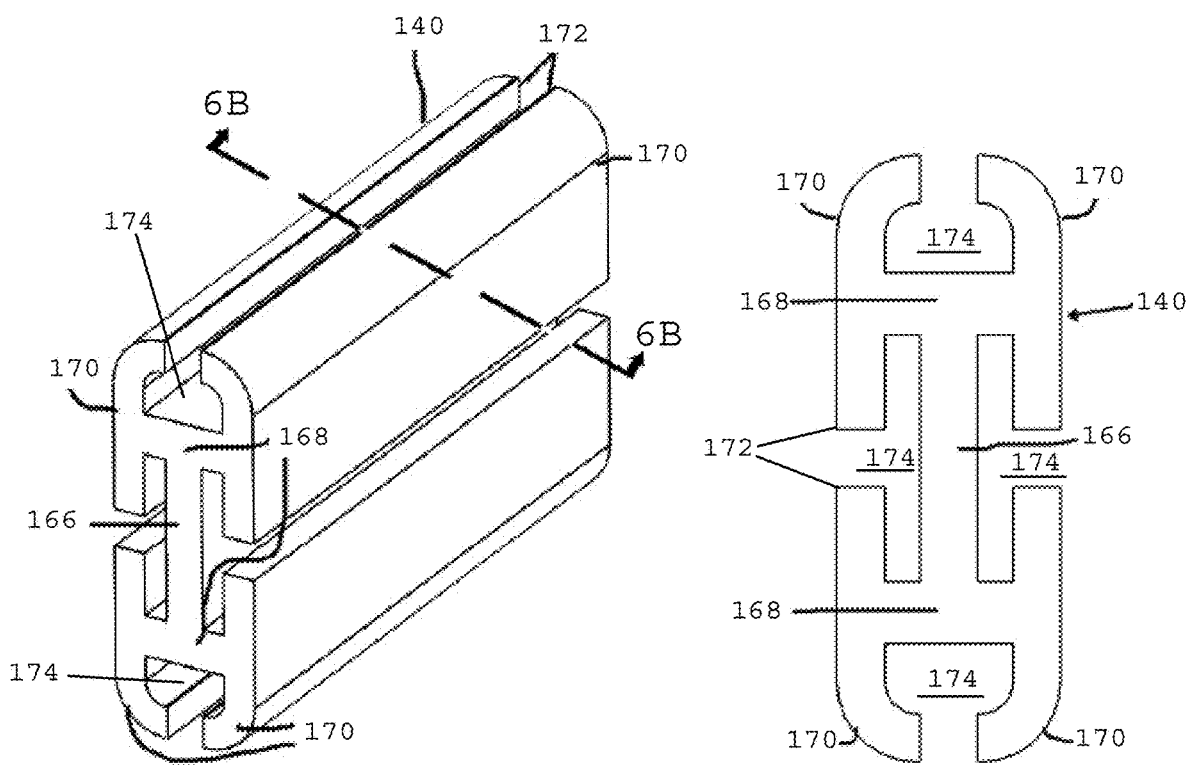
FIG. 6A
FIG. 6B

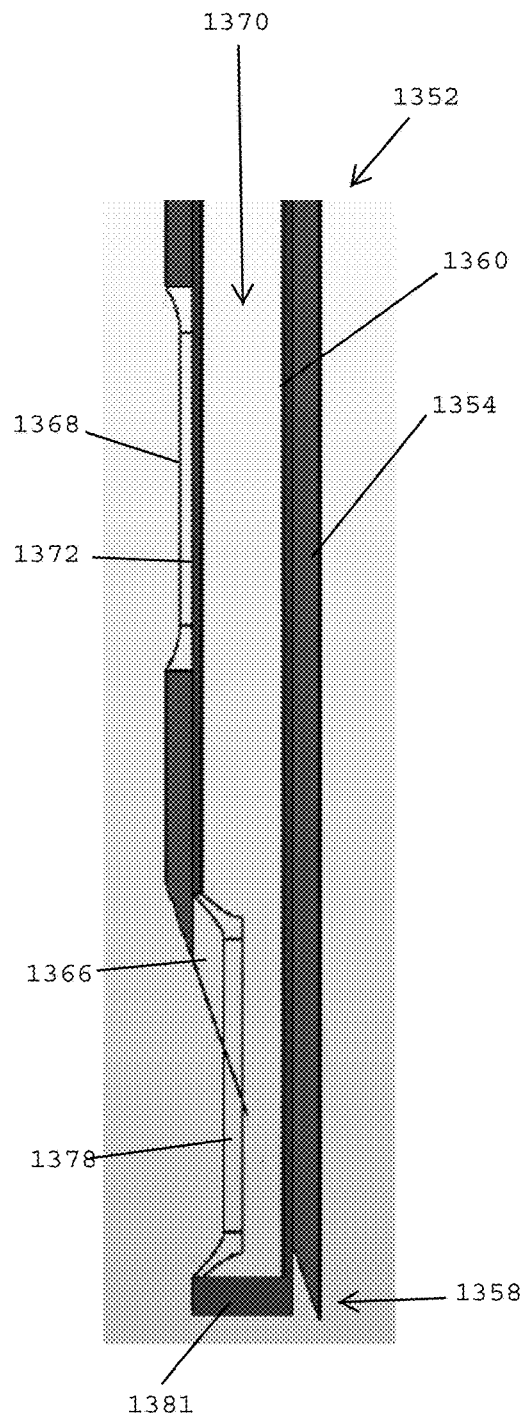
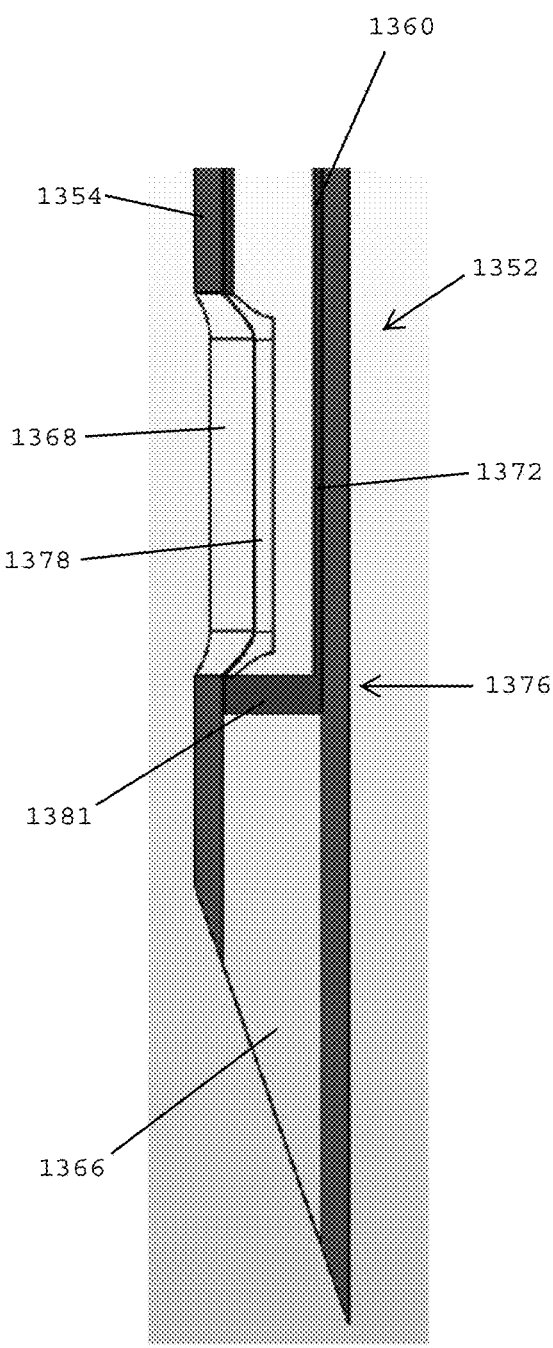
FIG. 33
FIG. 34

TISSUE EXPANDERS HAVING INTEGRATED DRAINAGE AND INFUSION ASSEMBLIES

CROSS-REFERENCE TO RELATED APPLICATIONS

The present patent application claims benefit of U.S. Provisional Application Ser. No. 62/752,813, filed Oct. 30, 2018, and is related to U.S. Provisional Application Ser. No. 62/752,839, filed Oct. 30, 2019, the disclosures of which are hereby incorporated by reference herein.

BACKGROUND OF THE INVENTION

Field of the Invention

The present patent application is generally related to implantable devices, and is more specifically related to tissue expanders having integrated drainage and fluid delivery components.

Description of the Related Art

Tissue expanders are devices that are implanted beneath the skin or muscle and then gradually inflated to stretch the overlying tissue. Expanders are commonly used to either create a pocket for receiving a permanent prosthesis, or to generate an increased skin surface area in anticipation of the new skin being utilized for grafting or reconstruction.

Tissue expanders are typically formed of a silicone polymer shell. After implantation, a fluid, such as saline, is periodically injected into the tissue expander to enlarge it over time. Between injections, the surrounding skin is permitted to stretch and grow to create the increased skin surface and the increased tissue pocket for receipt of a permanent implant. Typically, a tissue expander has an injection element through which fluid can be introduced into or withdrawn from the expander. One such injection element is an integrated port having a septum that can be pierced with a hypodermic needle for the introduction into or withdrawal of fluid from the expander. Alternatively, the injection element may be a self-sealing area on the tissue expander which allows penetration by a hypodermic needle and self-closing after the needle has been withdrawn from the expander.

Conventional, commercially available tissue expanders have a single port that is used for inflating and deflating the shell of the tissue expander. They have no means for draining fluid (e.g., seroma) that forms around the outside of the shell of the tissue expander after implantation.

After surgery, patients typically have surgical drains placed to prevent blood and lymphatic fluid from building up under the skin, allowing for a quicker recovery. Some patients are sent home with drains that are implanted and connected to an external reservoir. Emptying these reservoirs can be traumatic because the patients have to measure and empty the reservoirs periodically (e.g., every morning). Many patients loathe surgical drains and look forward to having the drains removed.

In view of the above-noted problems, there is a need for tissue expanders having a single injection port that may be used for both inflating and deflating the tissue expander and draining fluid that collects around the tissue expander following surgery. There is also a need for tissue expanders having a single injection port that may be used for inflation/deflation, draining fluid and infusing fluid (e.g., an antibiotic solution) around the outside of an implanted tissue expander.

Moreover, there remains a need for tissue expanders that remove seroma fluid without the need for a drain being attached 24 hours a day to a patient.

SUMMARY OF THE INVENTION

In one embodiment, a tissue expander preferably has a single injection port that may be used for inflating and deflating the tissue expander and draining fluid that forms around the outside of the tissue expander after implantation. Having a single injection port allows the empty tissue expander to be more easily folded and have a lower profile, which reduces the incision size needed for implantation. In addition, having a single injection port desirably reduces the total metal content of the tissue expander, which helps with MRI visualization and patient radiation. In addition, having only one injection port (with less metal than found in tissue expanders having two injection ports) will reduce the overall weight of the tissue expander.

In one embodiment, the injection port desirably includes a needle guard having a needle guard base and a needle guard rim that projects upwardly from the needle guard base. In one embodiment, the needle guard may be made of metal. In one embodiment, the needle guard may be made of polymer materials such as plastic. The injection port preferably includes a barrier membrane that is positioned in the needle guard. The barrier membrane divides the injection port into two distinct chambers, an inflation chamber in fluid communication with one or more inflation/deflation ports that are used for inflating and deflating the tissue expander, and a drainage chamber in fluid communication with one or more drainage ports that are used for draining fluid that collects outside the tissue expander.

In one embodiment, the shape, size and configuration of the barrier membrane of the injection port creates a space without occluding the inflation/deflation ports of the tissue barrier. The drainage chamber is coupled with the drainage ports and at least one drainage conduit (e.g., tubing) that connects to at least one drainage hole formed in the outer shell of the tissue expander. In one embodiment, the drainage conduit desirably includes a one-way check valve (e.g., a duck bill valve). In one embodiment, the one-way check valve allows fluid (e.g., seroma) to be drawn from the tissue surrounding the tissue expander without the possibility of inadvertently delivering saline into the patient.

In one embodiment, a first, conventional injection needle may be used for inflating and deflating the tissue expander with a fluid (e.g., a saline solution). In one embodiment, the first needle is the standard, injection needle that is used for inflation and deflation of the tissue expander. In one embodiment, the first needle may be used for injecting a solution (e.g., saline solution) into an outer shell to expand the size of the tissue expander. The first needle may also be used for removing the solution from the outer shell for reducing the size of the tissue expander.

In one embodiment, a second, specially designed needle, referred to as a drainage needle, may be used for draining fluid (e.g., seroma) that collects around the outer shell of the tissue expander following implantation. In one embodiment, the second drainage needle is used for drainage purposes only. The drainage needle desirably includes a hollow, cylindrical shaft made of medical grade material (e.g., stainless steel). In one embodiment, the distal end of the hollow, cylindrical shaft is closed and has a sharpened tip. The drainage needle preferably includes a side port formed in the side of the hollow needle shaft that is proximally spaced from the sharpened tip. The side port desirably enables fluid such as seroma fluid to be drawn into the drainage needle. The distance between the side port opening and the sharpened distal tip preferably positions the side port in communication with a drainage chamber as described in more detail herein.

In one embodiment, a tissue expander preferably includes integrated drainage and infusion systems. In one embodiment, the tissue expander desirably has a single injection port that may be used for inflating and deflating the tissue expander, for draining fluid that builds up around the tissue expander following surgery and implantation, and for delivering fluids around the outside of the shell following implantation.

In one embodiment, a tissue expander having an integrated drain preferably includes a shell having an opening and one or more drainage holes, and an injection port disposed in the opening of the shell and forming a fluid-tight seal with the shell, the injection port including a needle barrier having a needle barrier base with a top surface. In one embodiment, the injection port preferably includes a moveable barrier membrane overlying the top surface of the needle barrier base. In one embodiment, the moveable barrier membrane is moveable between a first position for inflating and deflating the shell with a first fluid and a second position for draining a second fluid from outside the shell.

In one embodiment, a magnet is coupled with the moveable barrier membrane. In one embodiment, a compressible spring is connected with the magnet. In one embodiment, the compressible spring is compressed for storing energy as the moveable barrier membrane moves from the first position to the second position. The energy may be released for returning the membrane to the first position.

In one embodiment, a needle may overlie the injection port and a second magnet may be coupled with the needle. In one embodiment, the second magnet repels the first magnet that is coupled with the moveable barrier for moving the moveable barrier from the first position to the second position.

In one embodiment, the tissue expander preferably includes an inflation port for inflating the shell with the first fluid, and a drainage port for draining the second fluid from outside the shell. In one embodiment, the inflation port is open and the drainage port is closed when the moveable barrier membrane is in the first position. In one embodiment, the inflation port is closed and the drainage port is open when the moveable barrier membrane is in the second position.

In one embodiment, a tissue expander preferably includes an injection port having a moveable barrier membrane that divides the injection port into an inflation chamber for inflating and deflating the tissue expander, and a drainage chamber for removing fluid that tends to collect around implants following surgery. In one embodiment, the moveable barrier membrane is connected to a magnet that, in turn, is coupled with a compressible spring. The barrier membrane is moveable between a first extended position in which the connected spring is extended, and a second retracted position in which the spring is compressed for storing energy in the spring.

In one embodiment, a first syringe with a needle is used for inflating and deflating the tissue expander. In one embodiment, a second syringe with a second needle contains a reversed pole magnet to repel the magnet coupled with the moveable membrane to occlude various openings. In the extended position, the moveable barrier membrane occludes a drainage port, with the compression spring keeping the moveable barrier membrane in place (i.e., in the extended position). With the barrier membrane in the extended position, saline injection for inflation and deflation is accomplished. A magnet mounted on the second syringe will repel the magnet coupled with the barrier membrane to push the movable barrier membrane down allowing drainage via syringe suction.

In one embodiment, a tissue expander having an integrated drain preferably includes a shell having an opening and one or more drainage holes, and an injection port disposed in the opening of the shell and forming a fluid-tight seal with the shell. In one embodiment, the injection port may include a needle barrier having a needle barrier base with a top surface, and a barrier membrane overlying the top surface of the needle barrier base. In one embodiment, the barrier membrane defines an inflation chamber located between the top surface of the needle guard base and a bottom surface of the barrier membrane, and a drainage chamber overlying a top surface of the barrier membrane. In one embodiment, one or more inflation ports are in fluid communication with the inflation chamber for inflating and deflating the shell with a first fluid. In one embodiment, a drainage conduit is in fluid communication with and extends between the drainage chamber and the one or more drainage holes for draining a second fluid from outside the shell.

In one embodiment, a first needle is used for inflating the shell and a second needle is used for draining fluid from around the outside of the shell. In one embodiment, the first needle has an opening at a pointed distal tip. In one embodiment, the first needle is adapted for insertion into the injection port so that the opening at the pointed distal tip is aligned with the inflation chamber for selectively inflating and deflating the shell using the first fluid. In one embodiment, the second needle has a closed distal tip and a side port spaced proximally from the closed distal tip. The second needle is adapted from insertion into the injection port so that the side port of the second needle is aligned with the drainage chamber for draining the second fluid from outside the shell.

In one embodiment, a tissue expander may include an infusion chamber overlying the top surface of the barrier membrane and separated from the drainage chamber, and an infusion conduit in fluid communication with and extending between the infusion chamber and at least one of the drainage holes for delivering an infusion fluid to the outside the shell.

In one embodiment, the tissue expander includes a needle assembly that is adapted for insertion into the injection port assembly. In one embodiment, the needle assembly has a first configuration in which an inflation lumen of the needle assembly is in fluid communication with the inflation chamber for selectively inflating and deflating the shell using the first fluid and a second configuration in which a drainage lumen of the needle assembly is in fluid communication with the drainage chamber for draining the second fluid from outside the shell.

In one embodiment, the needle assembly preferably includes a needle having an elongated shaft with a proximal end and a distal end. In one embodiment, the needle desirably includes the inflation lumen located at the distal end of the elongated shaft that is aligned with the inflation chamber and the drainage lumen that is proximal to the inflation lumen that is aligned with the drainage chamber, whereby the barrier membrane isolates the inflation lumen from the drainage lumen.

In one embodiment, the needle assembly includes an insert disposed inside the elongated shaft of the needle, which is moveable between an extended position in which the inflation lumen is open and the drainage lumen is closed, and a retracted position in which the inflation lumen is closed and the drainage lumen is open.

In one embodiment, the insert of the needle assembly preferably includes an elongated shaft having a proximal end that is open, a distal end that is closed by a distal end wall, and an elongated conduit that extends from the proximal end to the distal end of the insert. In one embodiment, the insert preferably has a side port formed in an outer wall of the elongated shaft of the insert that is in communication with the elongated conduit of the insert. In one embodiment, the side port of the insert is in alignment with the inflation lumen of the needle when the insert is in the extended position and the side port of the insert is in alignment with the drainage lumen of the needle when the insert is in the retracted position.

In one embodiment, the needle guard desirable has a needle guard rim that extends upwardly from the needle guard base.

In one embodiment, a barrier membrane support projects from the top surface of the needle guard base and toward the bottom surface of the barrier membrane for supporting an underside of the barrier membrane.

In one embodiment, the injection port assembly preferably includes an injection dome secured to an upper end of the needle guard rim. In one embodiment, the injection dome desirably includes a base having a bottom surface with an annular groove formed therein, whereby the upper end of the needle guard rim is disposed within the annular groove of the injection dome for securing the injection dome to the needle guard.

In one embodiment, the needle guard rim has a first height, and the injection dome has a second height that is less than the first height of the needle guard rim.

In one embodiment, the needle guard rim has one or more assembly openings formed therein that are located adjacent the upper end of the needle guard rim. In one embodiment, the one or more assembly openings are disposed within the annular groove of the injection dome.

In one embodiment, a drainage port passes through the needle guard rim for interconnecting the drainage chamber and the drainage conduit. In one embodiment, the drainage port is located between the bottom surface of the base of the injection dome and the needle guard base.

In one embodiment, silicone material (e.g., uncured silicone), such as silicone sheeting, preferably overlies the upper end of the needle guard rim and is in contact with the one or more assembly openings formed in the needle guard rim for securing the injection dome to the upper end of the needle guard rim.

In one embodiment, the drainage chamber is located between the bottom surface of the injection dome and the top surface of the barrier membrane.

In one embodiment, the one or more inflation ports pass through lateral openings provided in the needle guard rim. In one embodiment, the one or more inflation ports are located between the drainage port and a top surface of the needle guard base.

In one embodiment, the drainage conduit preferably has a second end that is coupled with a drain, which, in turn, is in fluid communication with the one or more drainage holes that are formed in the shell.

In one embodiment, the tissue expander may include a drainage manifold that is aligned with and covers the one or more drainage holes formed in the shell.

In one embodiment, the drainage manifold includes a drainage manifold port. In one embodiment, the second end of the drainage conduit may be secured to the drainage manifold port for connecting the drainage conduit to the drainage manifold.

In one embodiment, the drainage conduit preferably includes a one-way check valve that is configured to enable fluid passing through the drainage conduit to move in only one direction toward the drainage chamber of the injection port assembly.

In one embodiment, the drainage manifold has an inner face and an outer face. In one embodiment, the drainage manifold port projects from the inner face of the drainage manifold, and the outer face of the drainage manifold is secured to an inner surface of the shell to form a water-tight seal between the drainage manifold and the inner surface of the shell.

In one embodiment, the inner face of the drainage manifold surrounds a trough. In one embodiment, the tissue expander includes one or more drains that are disposed in the trough and that are aligned with the one of more drainage holes formed in the shell. In one embodiment, the drainage manifold port is in fluid communication with the trough and the one or more drains that are disposed within the trough.

In one embodiment, a tissue expander may include a drainage manifold having an inner face and an outer face, the outer face of the drainage manifold forming a water-tight seal with the inner surface of the shell and surrounding the one or more drainage openings formed in the shell.

In one embodiment, an integral drain preferably includes a sealed drain cover that is secured with the inner face of the drainage manifold. In one embodiment, a second end of the drainage conduit is preferably coupled with the drainage manifold.

In one embodiment, a tissue expander may include an infusion chamber that overlies the top surface of the barrier membrane, whereby the barrier membrane separates the infusion chamber from the drainage chamber.

In one embodiment, an infusion conduit in fluid communication with and extends between the infusion chamber and at least one of the one or more drainage holes formed in the shell for delivering an infusion fluid to the outside the shell.

In one embodiment, a tissue expander having an integrated drain preferably includes a shell having an injection port opening and one or more drainage holes formed in the shell, and an injection port assembly disposed in the injection port opening for forming a fluid-tight seal with the shell, the injection port assembly including a needle guard having a needle guard base with a top surface.

In one embodiment, a barrier membrane is disposed within the needle guard and overlies the top surface of the needle guard base.

In one embodiment, the barrier membrane define an inflation chamber that is located between the top surface of the needle guard base and a bottom surface of the barrier membrane for inflating and deflating the shell with a first fluid.

In one embodiment, the barrier membrane defines a drainage chamber located within the needle guard that overlies a top surface of the barrier membrane for draining a second fluid from outside the shell through the one or more drainage holes.

In one embodiment, a needle assembly is preferably configured for insertion into the injection port assembly. In one embodiment, the needle assembly has a first configuration in which an inflation lumen of the needle assembly is in fluid communication with the inflation chamber for selectively inflating and deflating the shell using the first fluid and a second configuration in which a drainage lumen of the needle assembly is in fluid communication with the drainage chamber for draining the second fluid from outside the shell.

In one embodiment, a barrier membrane support projects from the top surface of the needle guard base toward the bottom surface of the barrier membrane for supporting an underside of the barrier membrane.

In one embodiment, the needle guard preferably includes a needle guard rim that extends upwardly from the needle guard base.

In one embodiment, the injection port assembly preferably includes an injection dome that is secured to an upper end of the needle guard rim. In one embodiment, the injection dome preferably includes a base having a bottom surface with an annular groove formed therein, whereby the upper end of the needle guard rim is disposed within the annular groove of the injection dome for securing the injection dome to the needle guard.

In one embodiment, the needle guard rim has one or more assembly openings (e.g., elongated slots) that are formed therein that are located adjacent the upper end of the needle guard rim.

In one embodiment, the one or more assembly openings are disposed within the annular groove of the injection dome.

In one embodiment, silicone material overlies the upper end of the needle guard rim and is in contact with the one or more assembly openings formed in the needle guard rim.

In one embodiment, the silicone material preferably secures the injection dome to the upper end of the needle guard rim.

Dip molding using an appropriately sized and shaped mandrel can be used to form the outer shell, although other suitable means such as injection molding or spraying may also be used. With dip molding, the mandrel is dipped into silicone dispersion and then removed to allow for partial cure and solvent evaporation. The process is generally repeated several times. Once the outer shell has been formed it is removed from the mandrel. The dip molding process results in the formation of a partial shell that has an opening, e.g., a circular hole (patch hole), on the posterior side. The injection port is installed and the patch hole is subsequently covered with a patch that seals the hole, thus forming a complete, fluid impervious shell. The patch may be attached to the partial shell using silicone rubber or other similar biocompatible adhesive. The completed shell can either be non-filled or partially prefilled. After implantation, the expander is intraoperatively filled through the injection port with saline, gel, foam, or combinations of these materials or other suitable materials known in the art to gradually expand the tissue expander to the desired dimensions. Filling through the injection port typically takes place over the course of multiple office visits.

These and other preferred embodiments of the present invention will be described in more detail below.

BRIEF DESCRIPTION OF THE DRAWINGS

FIG. 5A shows an inner face of a drainage manifold of an integrated drainage system of a tissue expander, in accordance with one embodiment of the present patent application.

FIG. 5B shows an outer face of the drainage manifold shown in FIG. 5A.

FIG. 6A shows a perspective view of a drain assembled with the drainage manifold of FIGS. 5A and 5B, in accordance with one embodiment of the present patent application.

FIG. 6B shows a cross-sectional view of the drain shown in FIG. 6A.

FIG. 33 is a cross-sectional view of the needle assembly shown in FIG. 30 including the needle of FIGS. 31A-31O with the insert of FIGS. 32A-32B disposed inside the needle with the insert in an extended position, in accordance with one embodiment of the present patent application.

FIG. 34 is a cross-sectional view of the distal end of the needle and the insert of FIG. 33 with the insert in a retracted position, in accordance with one embodiment of the present patent application.

DETAILED DESCRIPTION OF PREFERRED EMBODIMENTS

Figure 1A:
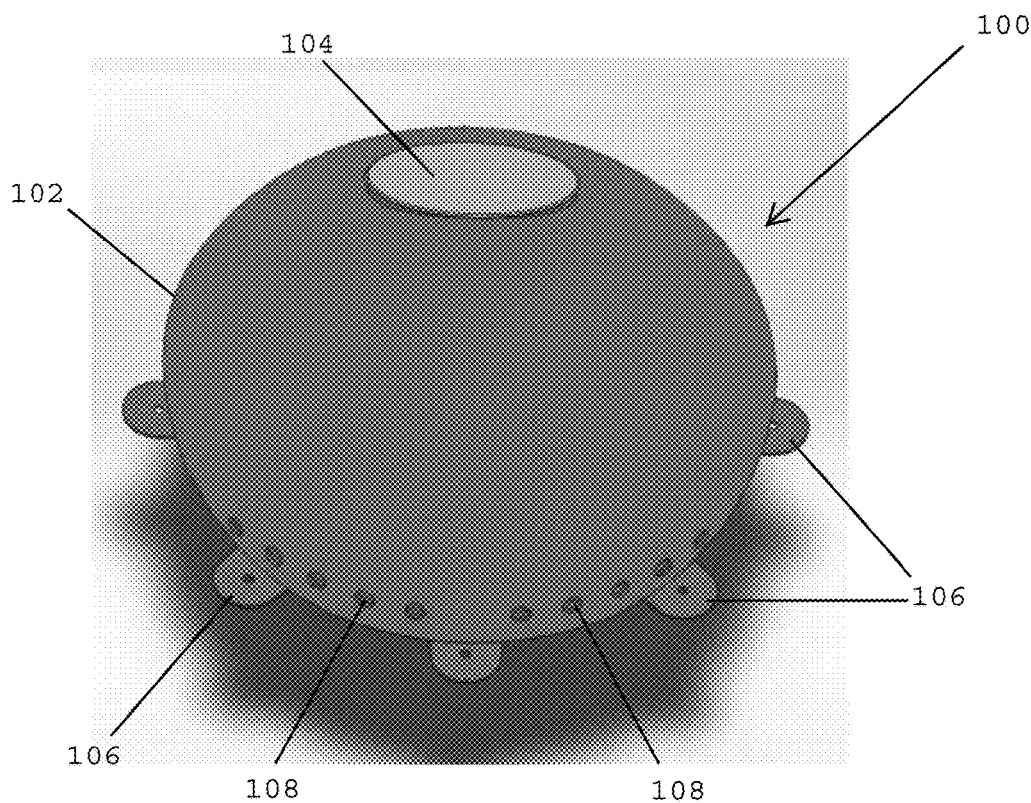
FIG. 1A shows a perspective view of a tissue expander having an integrated drainage system, in accordance with one embodiment of the present patent application.
Figure 1B:
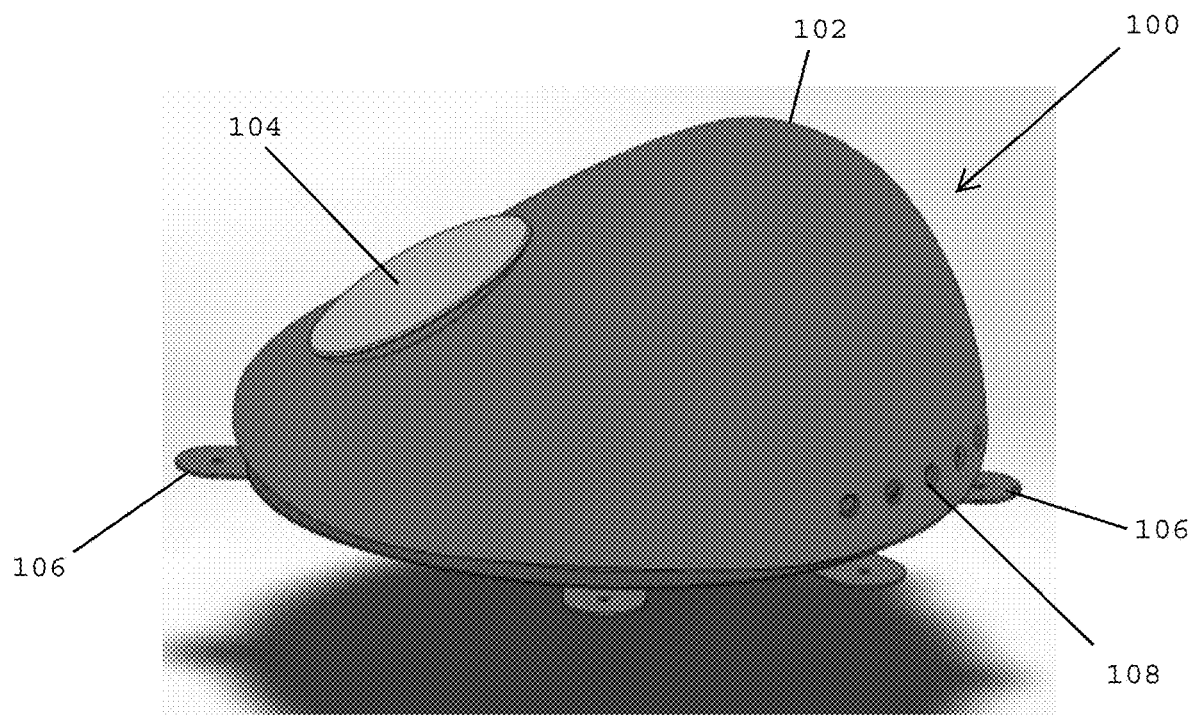
FIG. 1B shows a side view of the tissue expander shown in FIG. 1A.

Referring to FIGS. 1A and 1B, in one embodiment, a tissue expander 100 preferably includes a shell 102 and an injection port 104 located at a top side of the shell. The shell 102 may have any desired shape and any thickness that is suitable for the purpose of the particular tissue expander. The shell 100 may be formed of a biocompatible elastomer material such as silicone.

In one embodiment, the tissue expander 100 preferably includes one or more stability tabs 106 that may be used for securing the tissue expander 100 to tissue. In one embodiment, sutures or surgical fasteners may be utilized for securing the one or more stability tabs 106 to a patient's tissue. In one embodiment, the tissue expander 100 desirably includes one or more drainage holes 108 that are provided on the shell 102. The one or more drainage holes 108 may be used to drain fluid (e.g., seroma fluid) that may accumulate around the tissue expander 100 following surgical implantation.

Figure 2:
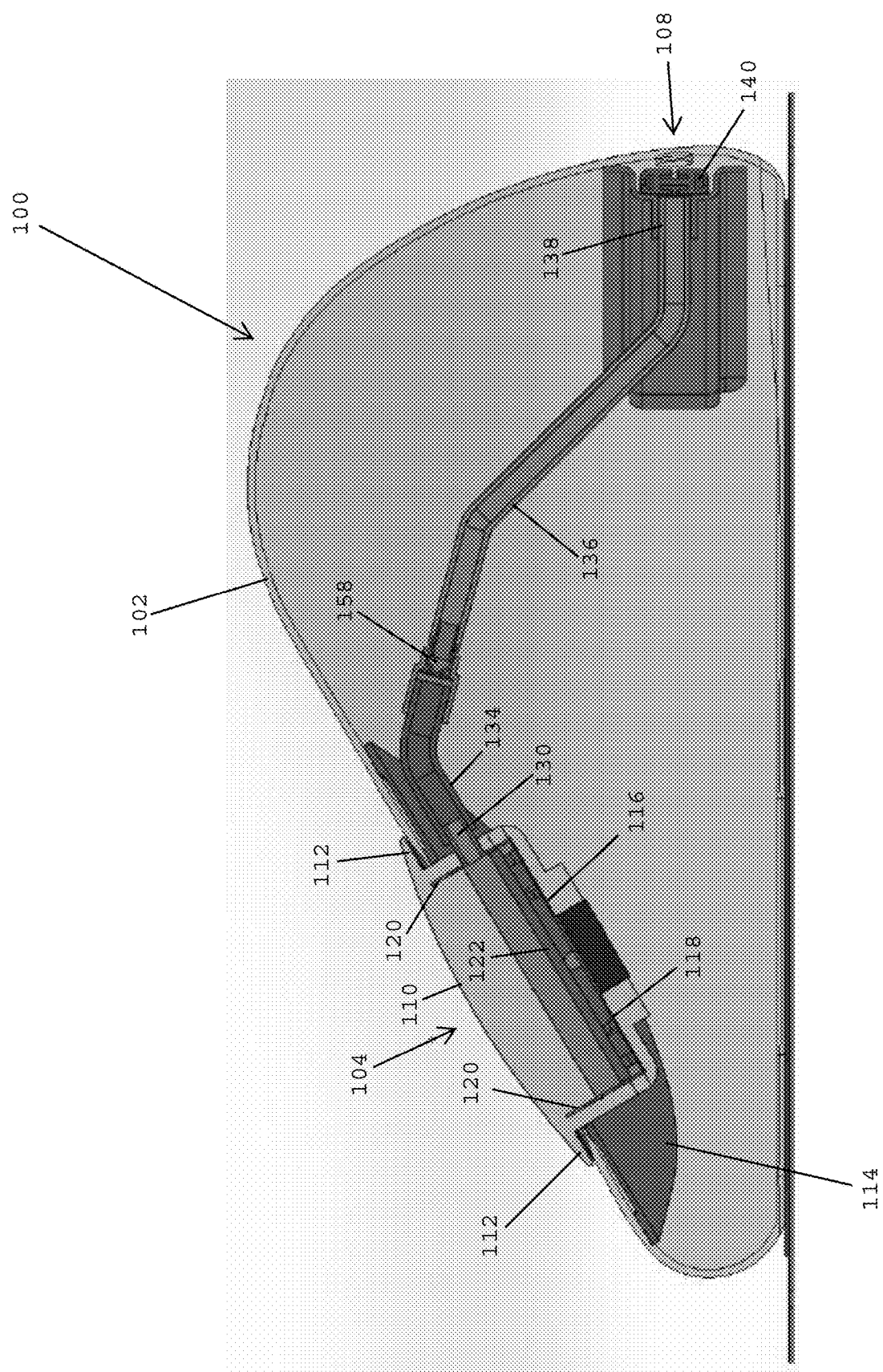
FIG. 2 shows a cross-sectional view of a tissue expander having an integrated drainage system, in accordance with one embodiment of the present patent application.
Figure 3:
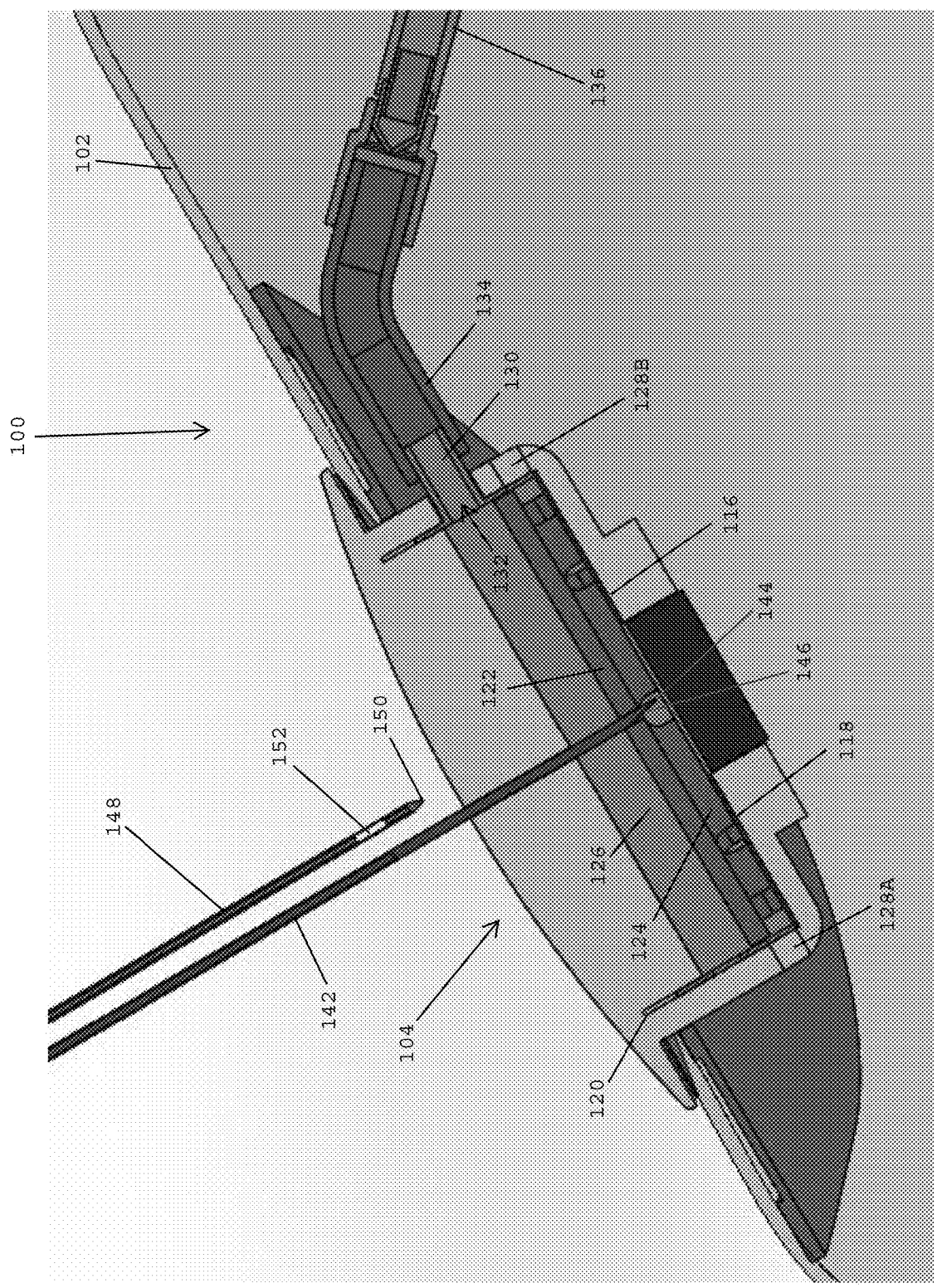
FIG. 3 shows a magnified view of an injection port of the tissue expander shown in FIG. 3.

Referring to FIGS. 2 and 3, in one embodiment, the injection port 104 may be secured to an opening that is present in the shell for sealing the shell 102. In one embodiment, the injection port 104 is fitted into the opening in the shell 102 at a location that faces toward a patient's skin surface. The injection port may be formed of an elastomeric material. In one embodiment, the injection port 104 desirably includes a septum region 110 that is preferably located at the central region of the upper surface of the injection port 104 and/or the tissue expander 100. The septum region 110 is desirably self-sealing for preventing the leaking of fluid from the tissue expander 100 after an injection needle is removed from the injection port 104.

In one embodiment, the injection port 104 desirably includes an outer flange 112 that overhangs the outer surface of the shell 102. In one embodiment, the injection port 104 desirably includes a self-sealing, safety patch 114 that is secured to the inner surface of the shell 102, whereby the shell is at least partially sandwiched between the flange 112 of the injection port and the self-sealing, safety patch 114. The self-sealing, safety patch preferably has a diameter that is larger than the flange 112 of the injection port 104 so that the safety patch extends beyond the outer perimeter of the flange 112.

In one embodiment, an appropriately sized and shaped mandrel may be used to form the shell 102 of the tissue expander 100. In one embodiment, the shell 102 may be formed using a dip molding methodology, although other methodologies may be used including spraying a mandrel with a shell forming solution or injection molding. During a dip molding method, a mandrel is dipped into silicone dispersion and then removed to allow for partial cure and solvent evaporation. The dipping step is repeated several times. Once the shell has been formed, it is removed from the mandrel. The dip molding process results in the formation of a partial shell that has an opening, e.g., a circular hole (patch hole). The injection port 104 and the safety patch 114 are installed, thus forming a complete, fluid impervious shell. The safety patch 114 may be attached to the inner surface of the shell 102 using silicone rubber or other similar biocompatible adhesives. The completed shell can be non-filled or partially pre-filled. After implantation, the tissue expander 100 is filled through the septum region 110 with saline, gel, foam, or combinations of these materials or other suitable materials known in the art to gradually expand the tissue expander 100 to the desired dimensions. This typically takes place over the course of multiple office visits.

In one embodiment, the injection port 104 desirably includes a needle guard 116 having needle guard base 118 and a needle guard rim 120 that extends upwardly from the needle guard base 118. In one embodiment, the needle guard rim 120 completely surrounds the outer perimeter of the needle guard base 118.

In one embodiment, the injection port 104 desirably includes a barrier membrane 122 that extends from one side of the needle guard rim 120 to an opposite side of the needle guard rim portion 120. In one embodiment, the barrier membrane 122 preferably overlies the needle guard base 118 and is co-extensive with the area of the needle guard base 118. The barrier member 122 preferably divides the injection port 104 into an inflation chamber 124 that is used to introduce an inflation solution into the shell 102 to expand the tissue expander and/or remove a solution from the shell to deflate the tissue expander, and a drainage chamber 126 that is used to drain fluid (e.g., seroma fluid) that may collect around the shell 102 of the tissue expander 100 following implantation.

In one embodiment, the inflation chamber 124 is in fluid communication with shell inflation ports 128A, 128B that pass through lateral openings provided in the needle guard rim 120. In one embodiment, an injection needle may be used to introduce fluid (e.g., saline solution) into the inflation chamber 124 whereupon it flows through the inflation ports 128A, 128B for inflating the shell 102 with the solution. In one embodiment, an injection needle may be used to generate a vacuum within the inflation chamber with removing fluid from the shell 102 to deflate the tissue expander 100.

In one embodiment, the drainage chamber 126 of the injection port 104 preferably includes a drainage port 130 that passes through an opening 132 formed in the needle guard rim 120 of the needle guard 116. In turn, the drainage port 130 is connected to a first end 134 of a drainage conduit 136. The drainage conduit 136 desirably has a second end 138 that is coupled with a drain 140, which is in fluid communication with one or more drainage holes 108 formed in the shell 102.

In one embodiment, a first needle 142 is utilized for inflating and deflating the shell 102 of the tissue expander 100. The first needle 142 preferably has a pointed tip 144 and an opening 146 provided at the pointed tip 144. In one embodiment, the pointed tip 144 of the first needle 142 is passed through the septum 110 and the barrier membrane 122 so that the opening 146 at the distal tip 144 of the first needle 142 is aligned with the inflation chamber 124 of the injection port 104. Once the opening 146 of the first needle 142 is positioned within the inflation chamber 124, a fluid (e.g., saline solution) may be passed through the needle opening 146 whereupon the injected fluid flows into the inflation chamber 124, through lateral openings in the needle guard rim 120, and through the inflation ports 128A, 128B for inflating the shell 52 with the injected fluid. In order to deflate the tissue expander 100, the first needle 142 may be used to remove fluid from the shell by withdrawing fluid through the inflation ports 128A, 128B and into the inflation chamber 124, whereupon the fluid may be removed from the shell 102 via the first needle 142.

In one embodiment, a second needle 148 may be used to drain fluid that collects around the outer perimeter of the tissue expander 100. In one embodiment, the second needle 148 has a pointed distal tip 150 and a side port 152 that is spaced proximally away from the pointed distal tip 150. As will be described in more detail herein, the side port 152 of the second needle enables fluid that has collected around the outside of the shell to be drained and removed from a patient's body.

Figure 4A:
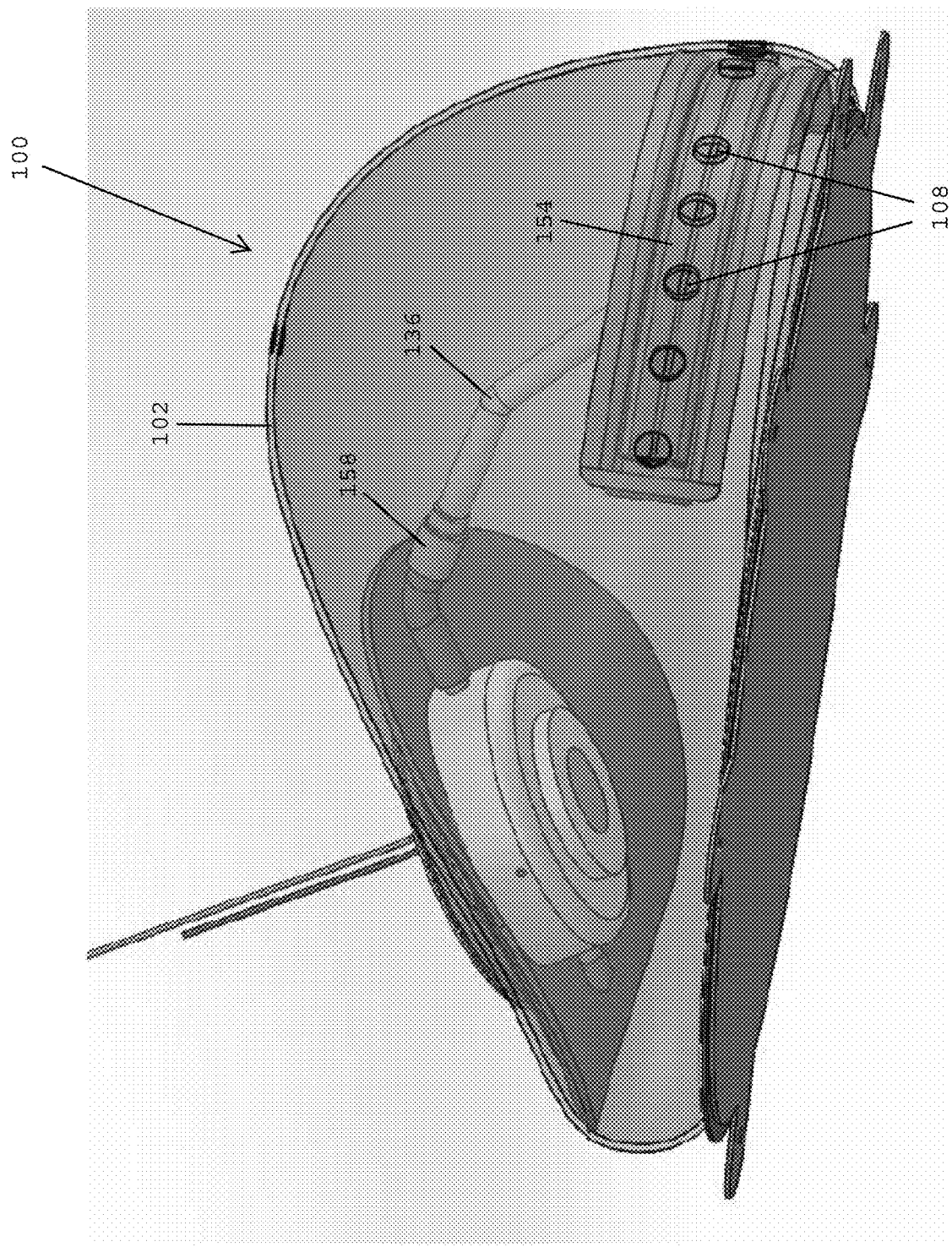
FIG. 4A shows a partial cross-sectional side view of the tissue expander shown in FIGS. 1A and 1B.
Figure 4B:
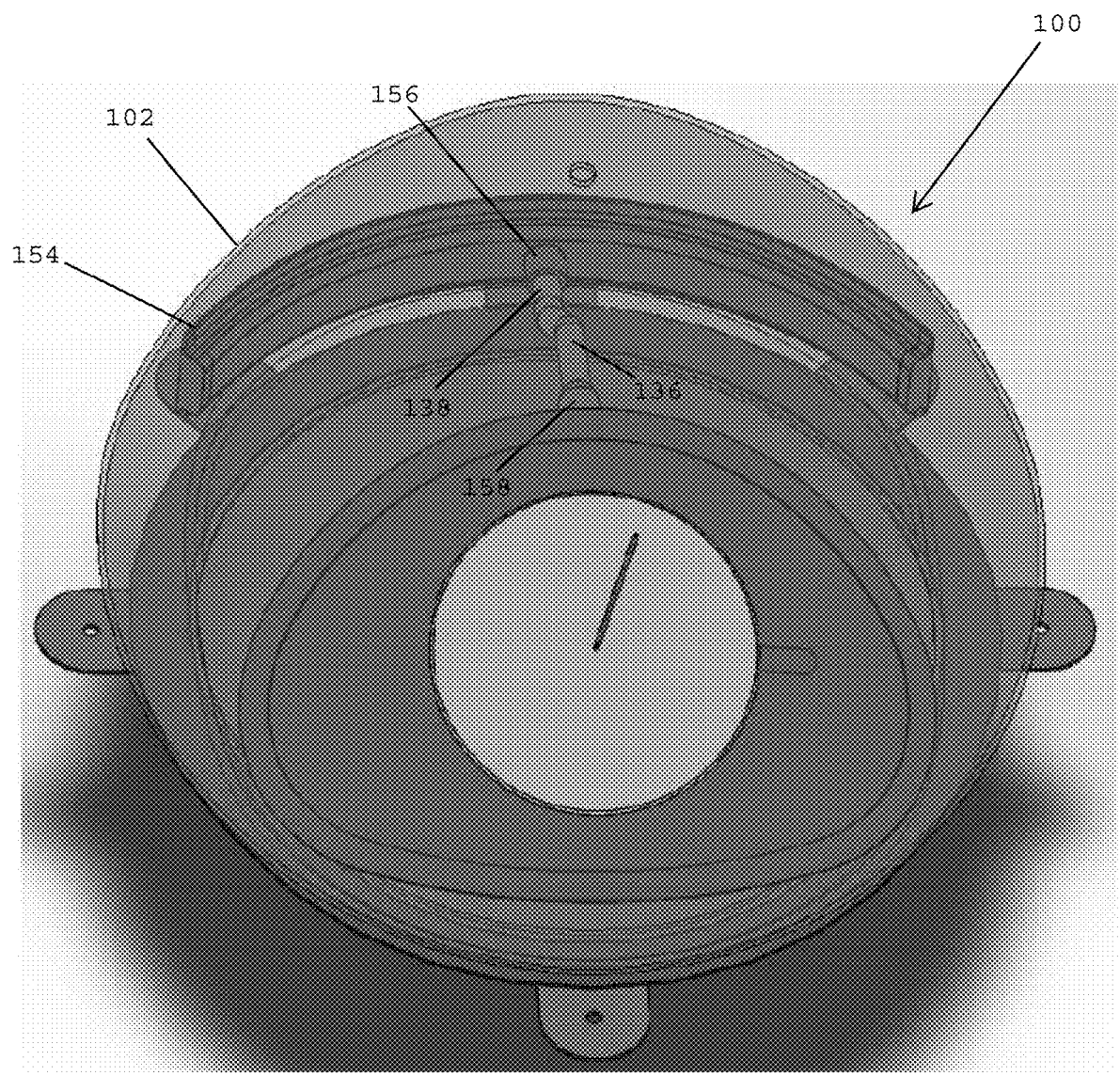
FIG. 4B shows a partial cross-section top view of the tissue expander shown in FIGS. 1A and 1B.

Referring to FIGS. 4A and 4B, in one embodiment, the tissue expander 100 preferably includes a drainage manifold 154 that is aligned with and covers the one or more drainage holes 108 that are provided on the shell 102. In one embodiment, the second end 138 of the drainage conduit 136 is secured to a drainage manifold port 156 for connecting the drainage conduit 136 to the drainage manifold 154.

In one embodiment, the drainage conduit 136 desirably includes a one-way check valve 158 (FIG. 2) that enables the fluid passing through the drainage conduit to move in only one direction designated DIR1, i.e., toward the drainage chamber 126 (FIG. 3) of the injection port 104.

Referring to FIGS. 5A and 5B, in one embodiment, the drainage manifold 154 desirably includes the drainage manifold port 156 that projects from an inner face 158 of the drainage manifold 154. In one embodiment, the drainage manifold 154 preferably has an outer face 160 that surrounds a trough 162, which is adapted to receive one or more drains 140 (FIG. 2) that are preferably aligned with the one or more drainage holes 108 (FIG. 1A) provided on the shell. The drainage manifold port 156 is desirably in fluid communication with the trough 162 provided at the front face 160 of the drainage manifold 154. In one embodiment, the outer face 160 of the drainage manifold 154 is preferably secured to the inner surface of the shell 102 (FIG. 1A) to form a water-tight seal with the inner surface of the shell so as to divide the fluid that is used to inflate and deflate the shell from the fluid that is drained from outside the shell.

In one embodiment, one or more drains 140 (FIG. 2) are desirably positioned within the trough 162 of the drainage manifold 154 for draining fluid from around the perimeter of the tissue expander. In one embodiment, the drains are desirably aligned with the drainage holes 108 (FIG. 1A) formed in the shell 102 of the tissue expander 100.

Referring to FIGS. 6A and 6B, in one embodiment, a drain 140 preferably has a core 166 with struts 168 that project from the core 166 along the longitudinal axis of the core. Each of the outer ends of the struts 168 have respective overhang portions 170 which extend longitudinally throughout the length of the struts 168. As shown in FIG. 6B, in one embodiment, the overhang portions 170 are arcuate members that extend on either side of their respective struts 168. The overhang portions 170 are sized to form a generally oval shaped member at the periphery of the drain 140, with small gaps between the adjacent overhang portions 170. Each of these gaps forms a longitudinal groove 172, parallel to the longitudinal axis of the core 166, and extending throughout the length of the drain 140. The core portion 166, the struts 168, and the overhand portions 170 cooperate to form plural channels or lumens 174 that extend along the length of the drain 140. The longitudinal grooves 172 permit fluid communication between the respective lumens 174 and a wound.

In one embodiment, the drain 140 may be similar to the surgical drains disclosed in U.S. Pat. No. 4,398,910 to Blake et al., the disclosure of which is hereby incorporated by reference herein.

Figure 7:
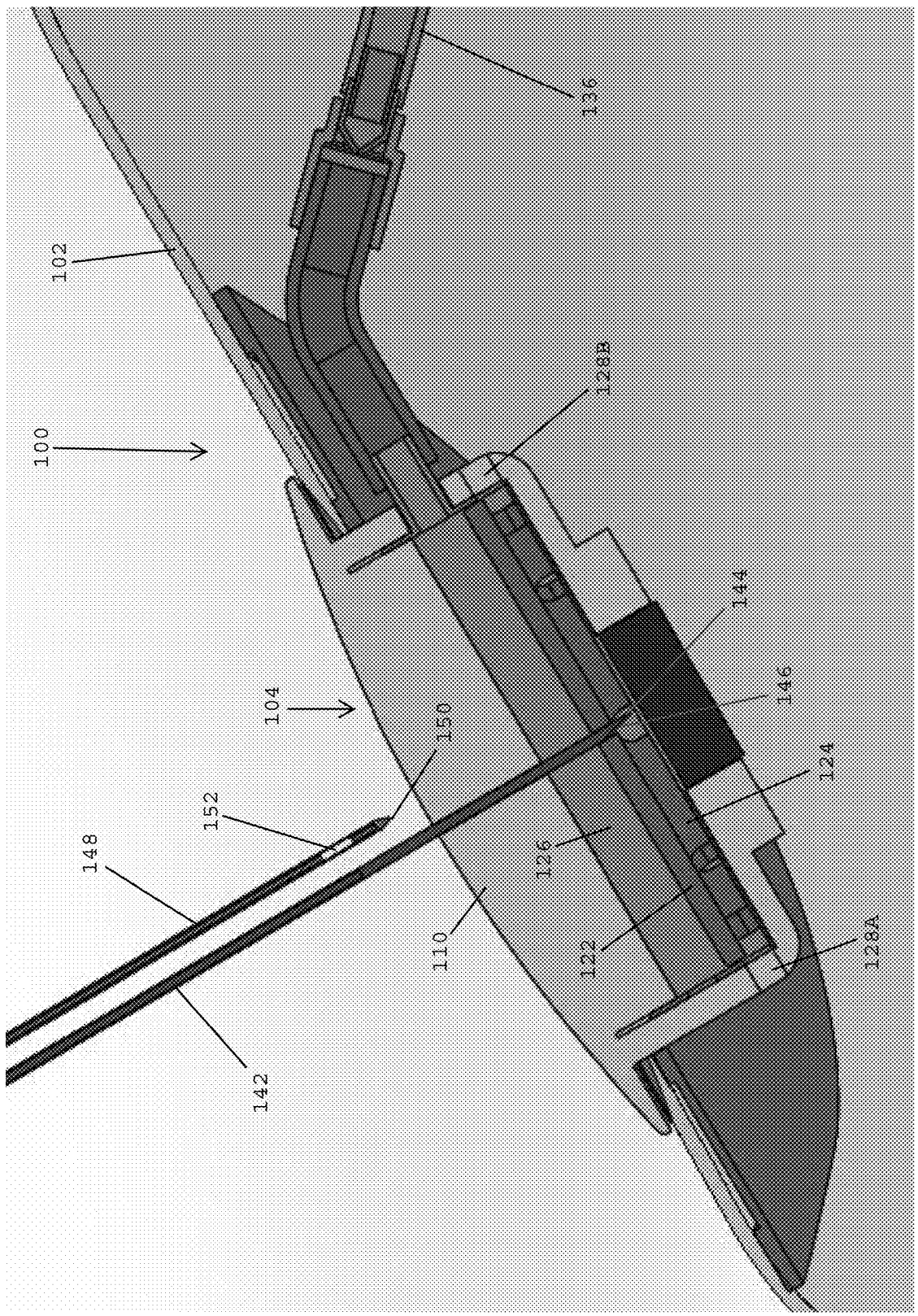
FIG. 7 shows a method of inflating a tissue expander, in accordance with one embodiment of the present patent application.

Referring to FIG. 7, in one embodiment, in order to inflate the tissue expander 100, the pointed distal tip 144 of the first needle 142 is passed through both the septum region 110 of the injection port 104 and the barrier membrane 122 until the opening 146 at the distal tip 144 of the inflation needle 142 is aligned with the inflation chamber 124 of the injection port. In one embodiment, a fluid (e.g., saline solution) is injected from the opening 146 at the distal tip 144 of the first needle 142 whereupon the injected fluid flows into the inflation chamber 124 and through the inflation ports 128A, 128B for inflating the shell 102 and expanding the tissue expander 100. The distal tip 144 is desirably halted by the needle guard base 118 of the needle guard 116 for prevented the distal tip of the first needle from passing through the bottom of the injection port 104 and/or damaging the shell of the tissue expander. If the opening 146 at the distal tip 144 of the first needle 142 were improperly aligned with the drainage chamber 126 of the injection port 104 and fluid under pressure was injected from the opening 146 of the first needle 142, the one-way check valve 158 (FIG. 2) provided inside the drainage conduit 136 will prevent the fluid from passing through the drainage conduit and reaching the drain 140 located at the second end 138 of the drainage conduit 136.

Figure 8A:
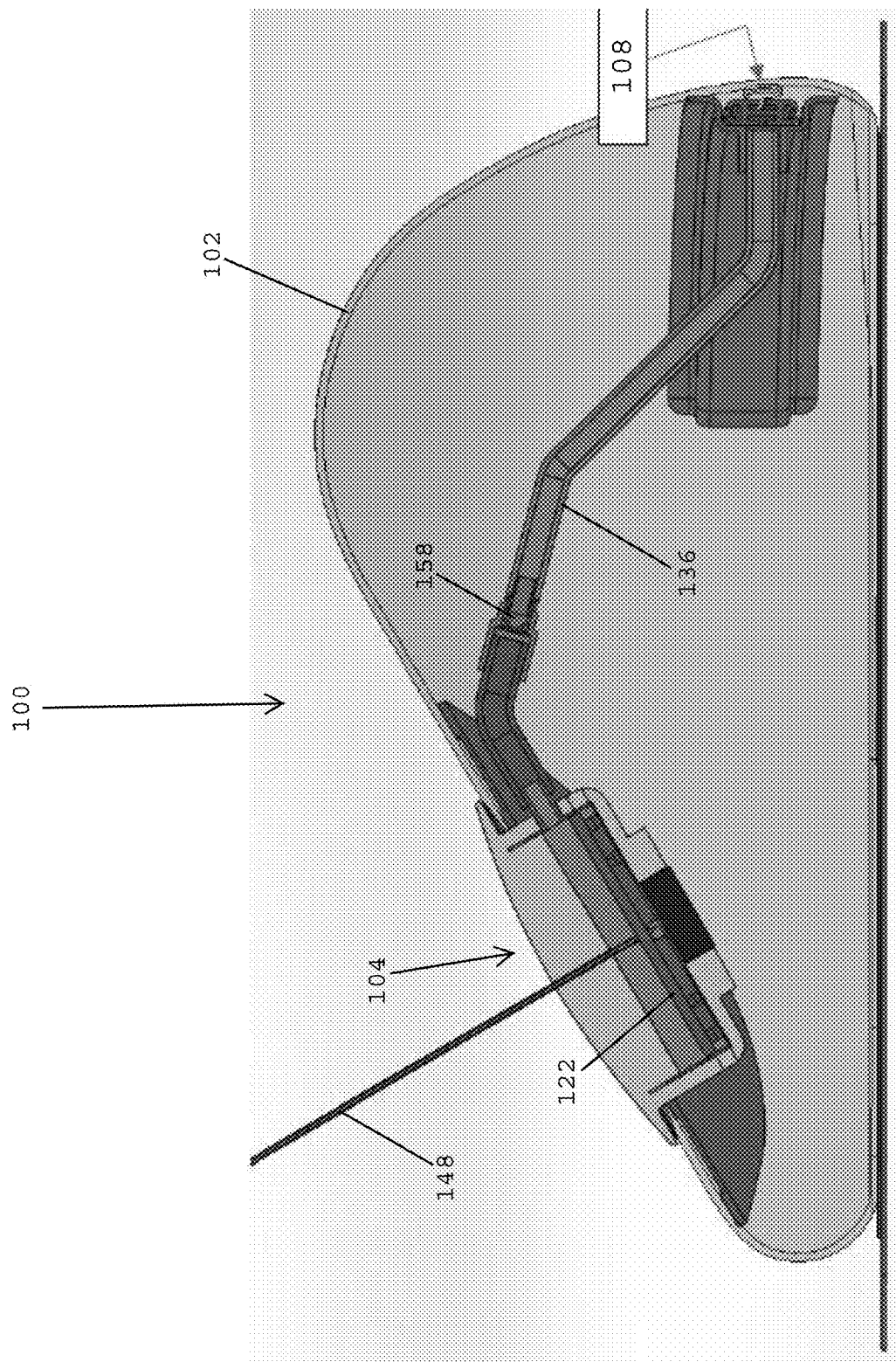
FIG. 8A shows a method of draining a tissue expander having an injection port and an integrated drainage system, in accordance with one embodiment of the present patent application.
Figure 8B:
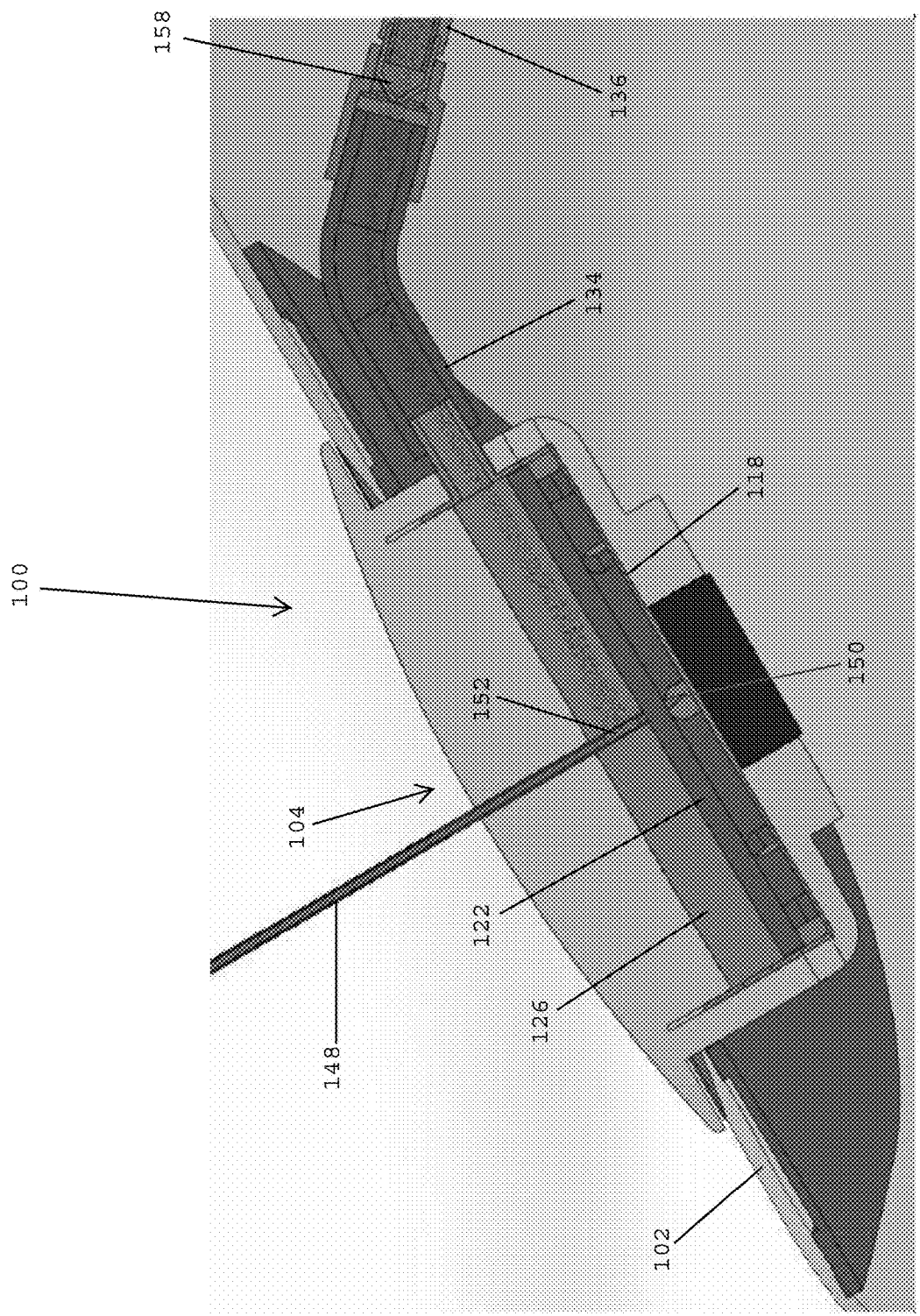
FIG. 8B shows a magnified view of the injection port of the tissue expander shown in FIG. 8A.

Referring to FIGS. 8A and 8B, in one embodiment, bodily fluid that collect around the shell 102 of the tissue expander 100 may be drained from the one or more drainage openings 108 (FIG. 1A) provided on the shell 102. In one embodiment, the second needle 148 (FIG. 3) is utilized for draining the fluid that has accumulated around the outer perimeter of the shell 102. In one embodiment, the pointed distal tip 150 of the second needle 148 is advanced through the barrier membrane 122 until the pointed tip 150 abuts against the top surface of the needle guard base 118 of the needle guard 116. When the pointed distal tip 150 of the second needle 148 engages the needle guard base 118, the side port 152 of the second needle 148 (which is spaced from the distal tip 150) is preferably aligned with the drainage chamber 126 of the injection port 104 that overlies the top surface of the barrier membrane 122. A vacuum may then be drawn through the second needle 148 for withdrawing fluid (e.g., seroma) through the drainage conduit 136. The drainage conduit 136 preferably includes the one-way check valve 158 that enables the accumulated fluid to flow in only one direction (e.g., toward the injection port 104). The drained fluid preferably passes through the one-way check valve 158, through the drainage port 130, and into the drainage chamber 126 where it is withdrawn through the side port 152 of the drainage needle 148. FIG. 8B shows the flow of the drained fluid as it flows through the one-way check valve 158, the first end 134 of the drainage conduit 136, the drainage chamber 126, and into the side port 152 of the second needle 148 for being removed from the shell 102 of the tissue expander 102.

Figure 9:
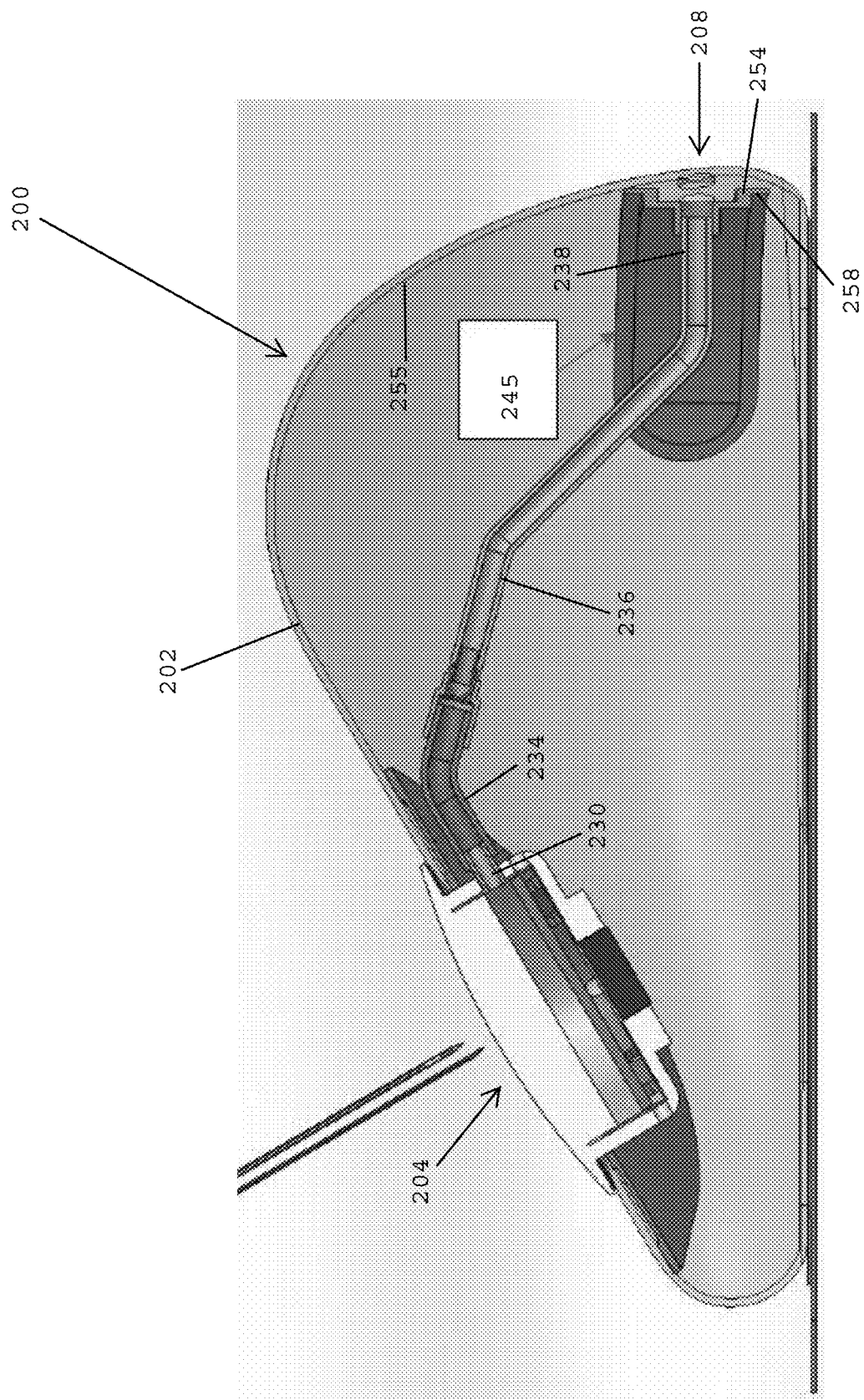
FIG. 9 shows a cross-sectional view of a tissue expander having an integrated drain, in accordance with one embodiment of the present patent application.

Referring to FIG. 9, in one embodiment, a tissue expander 200 has an integral drain provided therein for draining fluid and/or liquids that accumulate around the perimeter of the shell 202 of the tissue expander. In one embodiment, the tissue expander 200 preferably includes a drainage conduit 236 having a first end 234 that is coupled with a drainage port 230 of an injection port 204, and a second end 238 that is coupled with a drainage manifold 254 that is positioned adjacent drainage openings 208 provided on the shell 202. In one embodiment, the integral drain does not include a drain 140 (FIG. 6A) similar to that shown and described above in FIGS. 6A and 6B. Rather, the integral drain includes a sealed drain cover 245 that is secured with an inner face 258 of the drainage manifold 254. The outer face 260 of the drainage manifold 254 is preferably secured to an inner surface 255 of the shell 202 to form a water-tight seal between the inner surface of the shell and the outer face of the drainage manifold 254 for separating the inflation fluid that circulates inside the shell 202 from the liquid that accumulates around the shell 202 and that is drained through the one or more drainage holes 208.

Figure 10A:
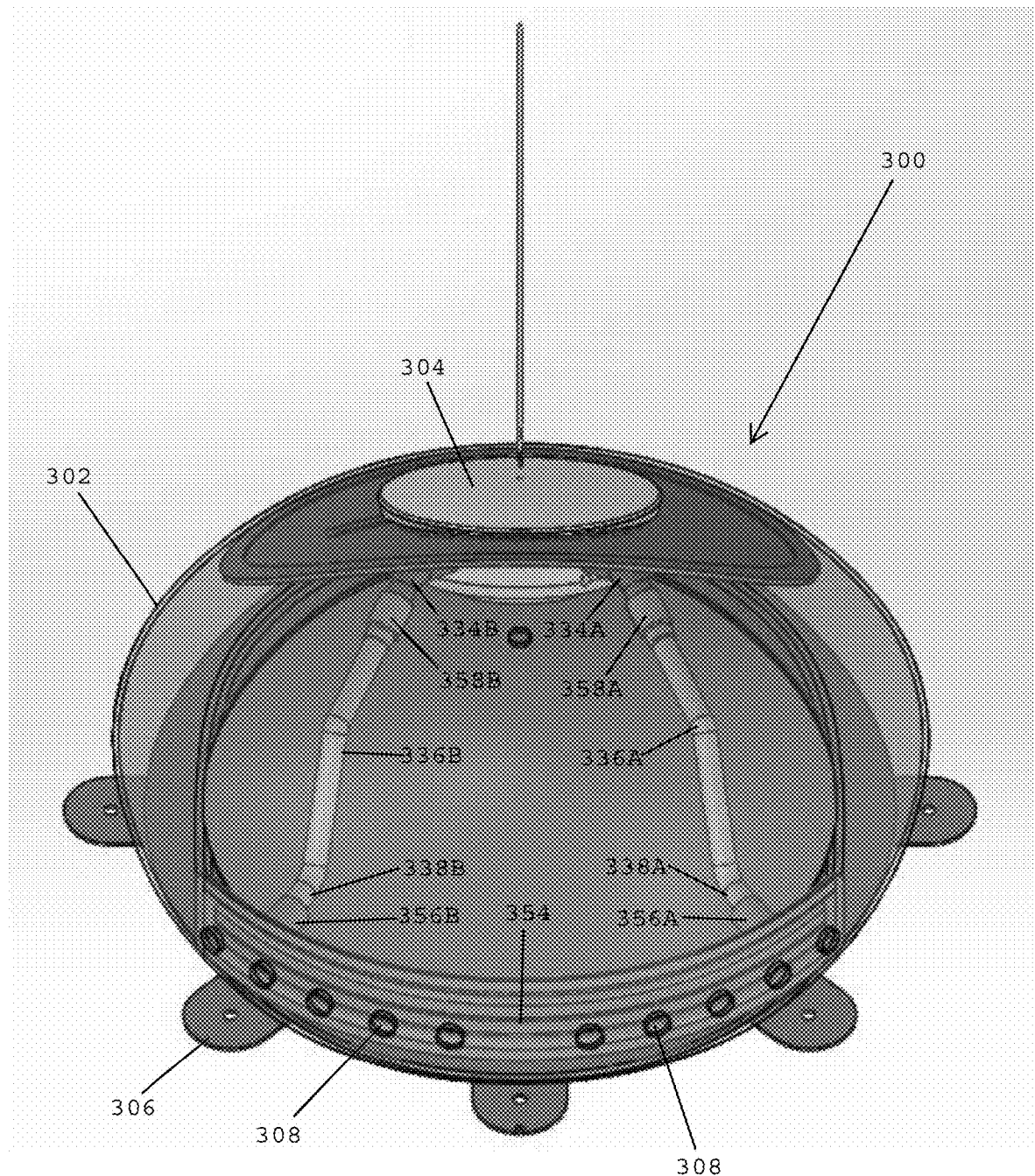
FIG. 10A shows a partial cross-sectional view of a tissue expander having an integrated drainage and infusion system, in accordance with one embodiment of the present patent application.
Figure 10B:
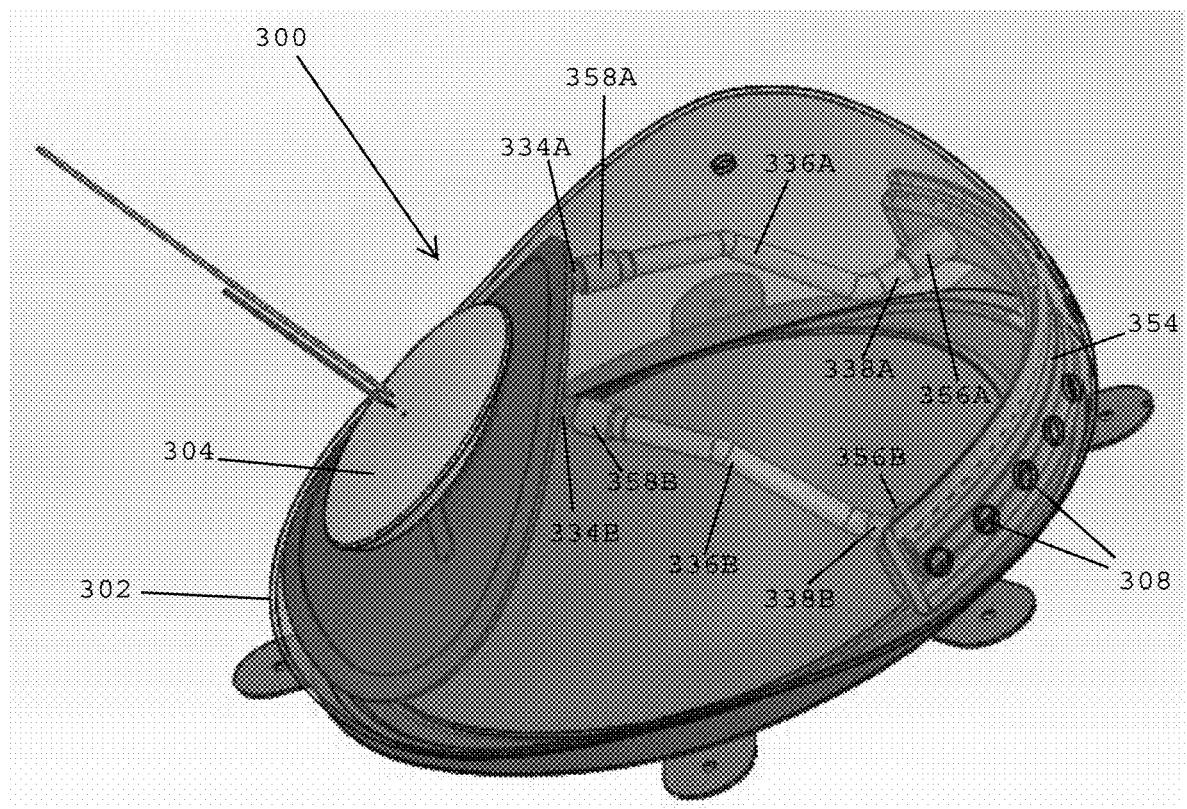
FIG. 10B shows a side view of the tissue expander shown in FIG. 10A.
Figure 10C:
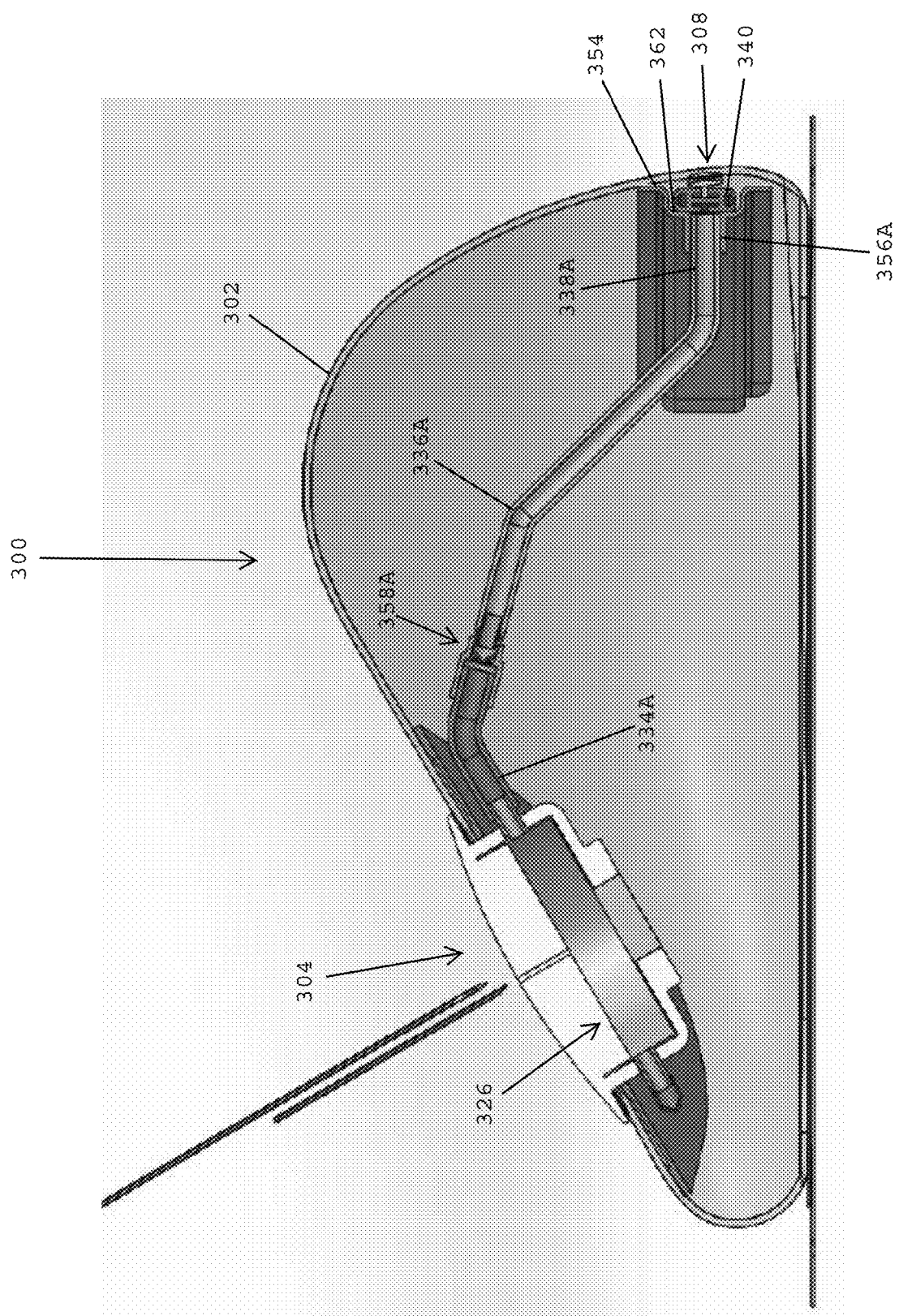
FIG. 10C shows a cross-sectional side view of the tissue expander shown in FIGS. 10A and 10B.

Referring to FIGS. 10A-10C, in one embodiment, a tissue expander 300 preferably includes an outer shell 302, an injection port 304, stabilizing tabs 306, and drainage and infusion holes 308 provided on the shell 302. In one embodiment, the tissue expander 300 desirably includes a manifold 354 that is preferably used for both drainage and infusion and that is positioned inside the shell 302 adjacent the drainage and infusion holes 308. In one embodiment, a drainage conduit 336A has a first end 334A coupled with a drainage and infusion chamber 326 of the injection port 304 and a second end 338A coupled with a drainage port 356A of the manifold 354. As will be described in more detail herein, the drainage conduit 336A desirably includes a one-way check valve 358A that allows fluid that is drained through the holes 308 to flow from the second end 338A to the first end 334A of the drainage conduit 336A, but not in the opposite direction from the first end 334A to the second end 338A of the drainage conduit 336A.

In one embodiment, the tissue expander 300 desirably includes an infusion conduit 336B having a first end 334B coupled with the drainage and infusion chamber 325 of the injection port 304 and a second end 338B coupled with an infusion port 356B provided on the manifold 354. In one embodiment, a solution (e.g., a medical solution, an antibiotic) may be passed through the infusion conduit 336B for being dispensed from the holes 308 formed in the shell 252. In one embodiment, the infusion conduit 336B desirably includes a one-way check valve 358B that allows an infusion solution to flow from the first end 334B of the infusion conduit 336B to the second end 338B of the infusion conduit 336B, but not flow through the infusion conduit 336B in the opposite direction.

Figure 11:
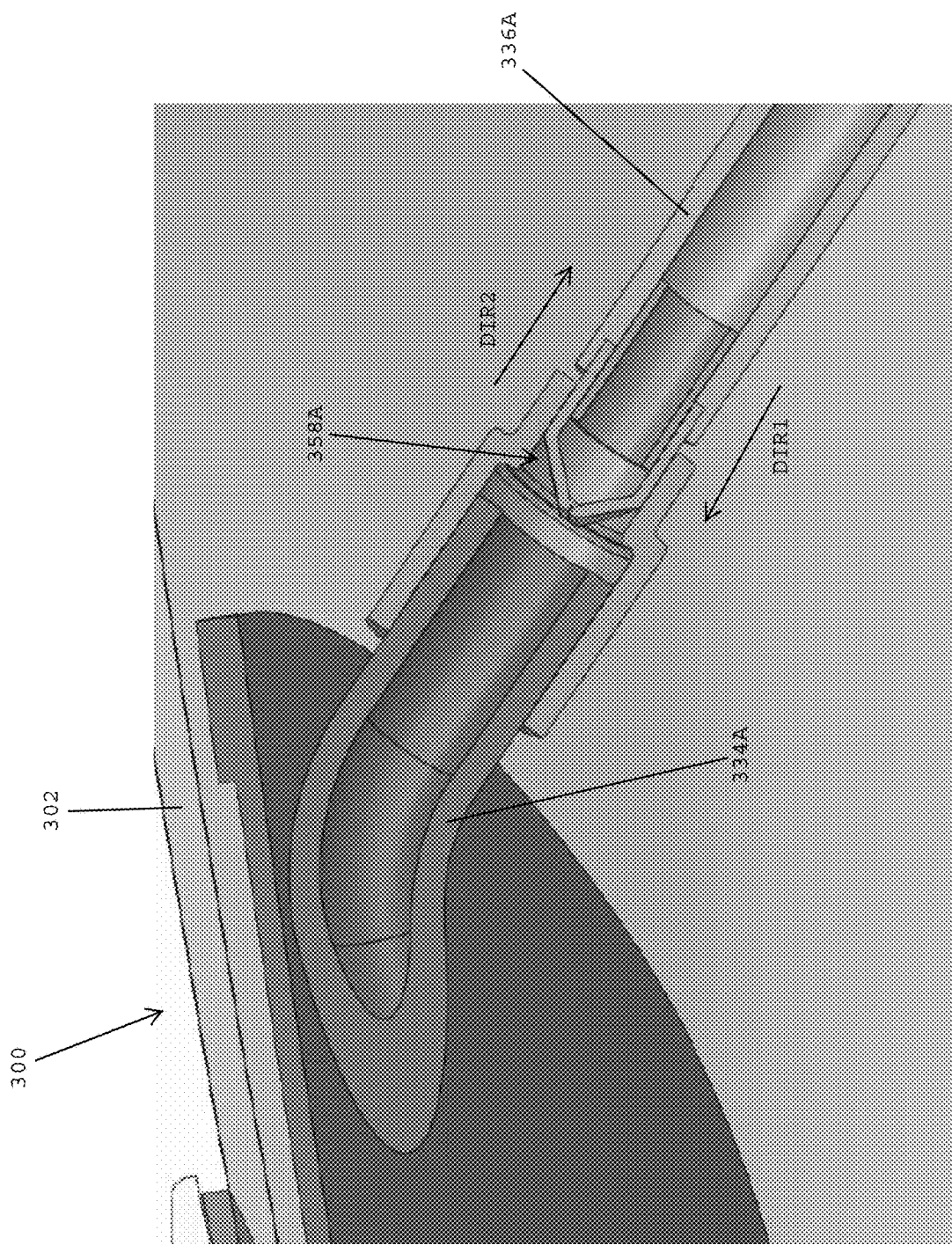
FIG. 11 shows a drainage conduit of the tissue expander shown in FIGS. 10A-10C, in accordance with one embodiment of the present patent application.

Referring to FIGS. 100 and 11, in one embodiment, the tissue expander 300 desirably includes the drainage conduit 336A having a one-way check valve 358A that allows the drained fluid to flow from the second end 338A to the first end 334A of the drainage conduit 336A in the direction designed DIR1, but not in the reverse direction designed DIR2. In one embodiment, the manifold 354 is secured to the second end 338A of the drainage conduit 336A. The drainage system desirably includes one of more drains 340 that are located within the trough 362 of the manifold 354 and that are located between the opening at the second end 338A of the drainage conduit 336A and the one or more holes 308 formed in the shell 302. The fluid that is drained through the one or more holes 308 passes through the one or more drains 340 and into the drainage conduit 336A.

Figure 12:
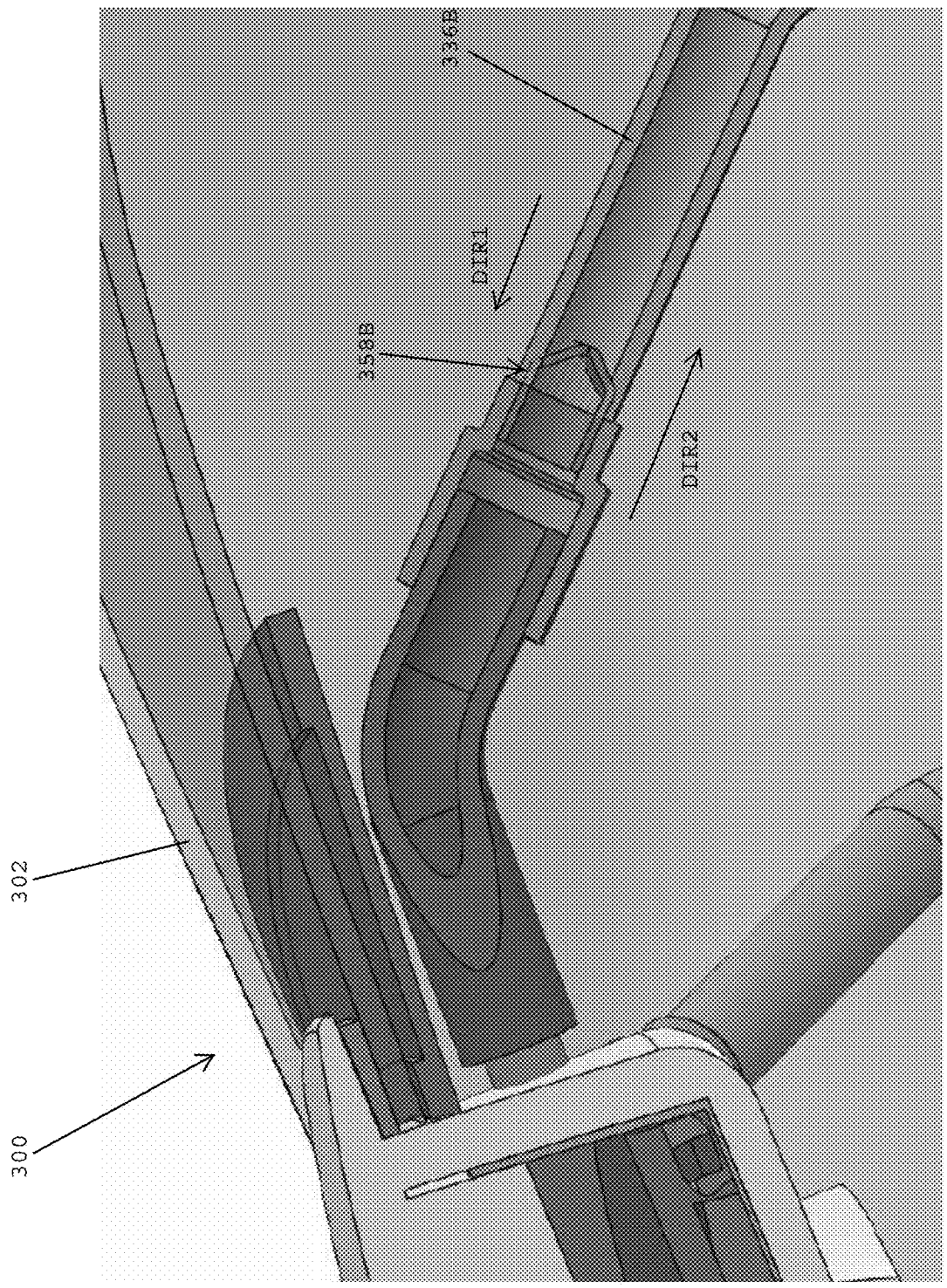
FIG. 12 shows an infusion conduit of the tissue expander shown in FIGS. 10A-10C, in accordance with one embodiment of the present patent application.

FIG. 12 shows the one-way check valve 358B provided in the infusion conduit 336B. The one-way check valve 358B enables the infusion fluid to flow in only one direction designed DIR2 from the first end 284B to the second end 288B of the infusion conduit 286B, but not in the opposite direction designated DIR1.

Figure 13:
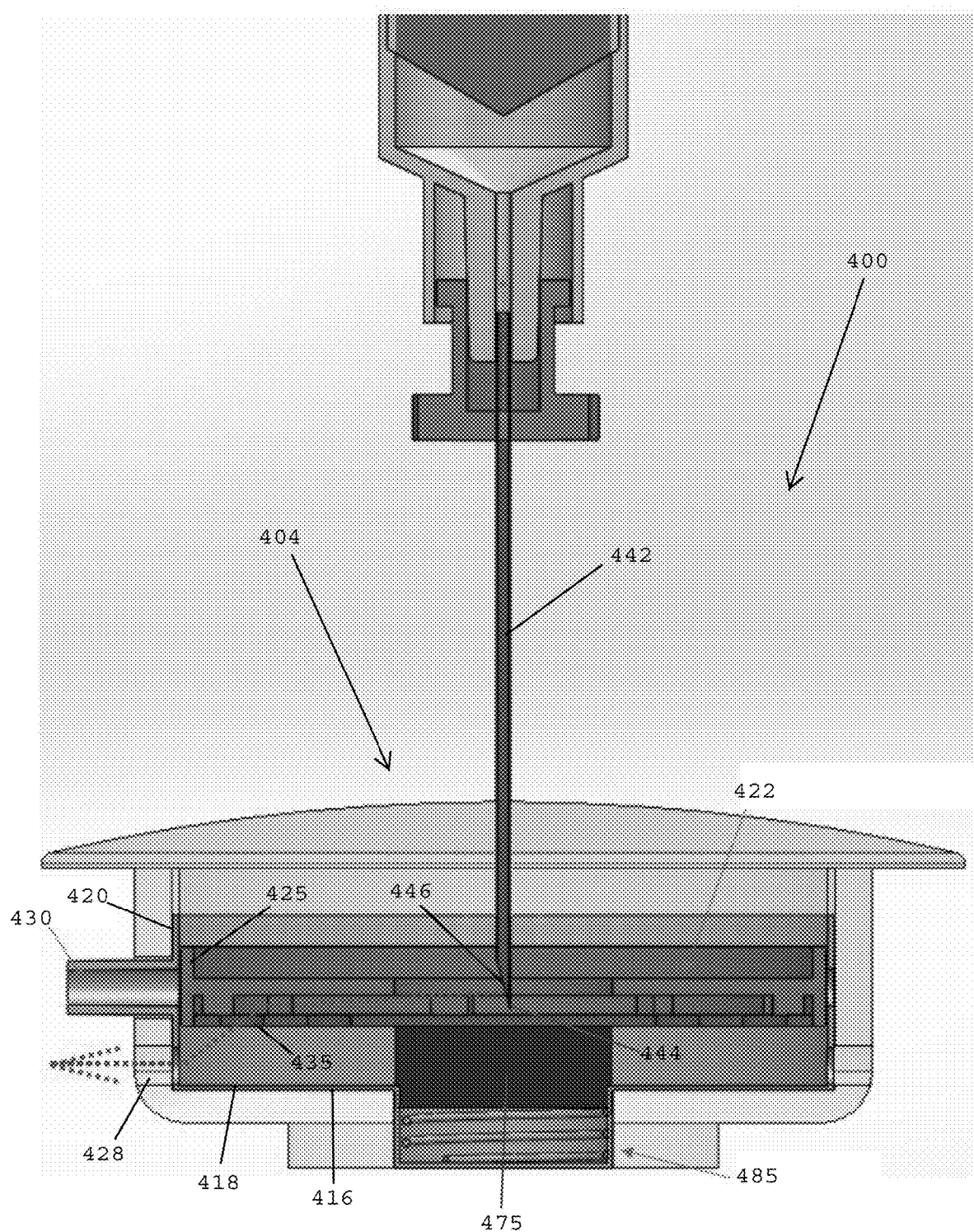
FIG. 13 shows an injection port of a tissue expander, the injection port having a moveable membrane that is coupled with a magnetic element, in accordance with one embodiment of the present patent application.

Referring to FIG. 13, in one embodiment, an injection port 404 of a tissue expander 400 desirably includes a moveable barrier membrane 422 that is positioned inside a needle guard 416 having needle guard base 418 and a needle guard rim 420 that projects upwardly from the needle guard base 418. The injection port 404 preferably includes a magnet 475 that is positioned atop a compressible spring 485 that normally urges the moveable barrier membrane 422 into an extended position shown in FIG. 13. In one embodiment, the moveable barrier membrane 422 desirably includes a membrane rim 425 that blocks a drainage port 430 when the moveable barrier membrane 422 is in the extended position shown in FIG. 13. In one embodiment, the magnet 475 and the movable barrier membrane 422 are connected together and move together between an extended position shown in FIG. 13 and a compressed position shown in FIG. 14B.

In one embodiment, in order to inflate a shell of a tissue expander with a solution, an inflation needle 442 having a distal tip 444 with an opening 446 is preferably passed through the dome 410 of the injection port 404 until the distal tip 444 of the needle 442 abuts against the top surface of the needle guard base 418 of the needle guard 416. The compression spring 485 is extended so that the magnet 475 and the moveable barrier membrane 422 are in the extended position. When a solution is injected from the opening 446 at the distal tip 444 of the needle 442, the injected solution desirably flows through openings 435 in a floor of the barrier membrane 422 and through an inflation port 428 for filling an outer shell of the tissue expander 400.

Figure 14A:
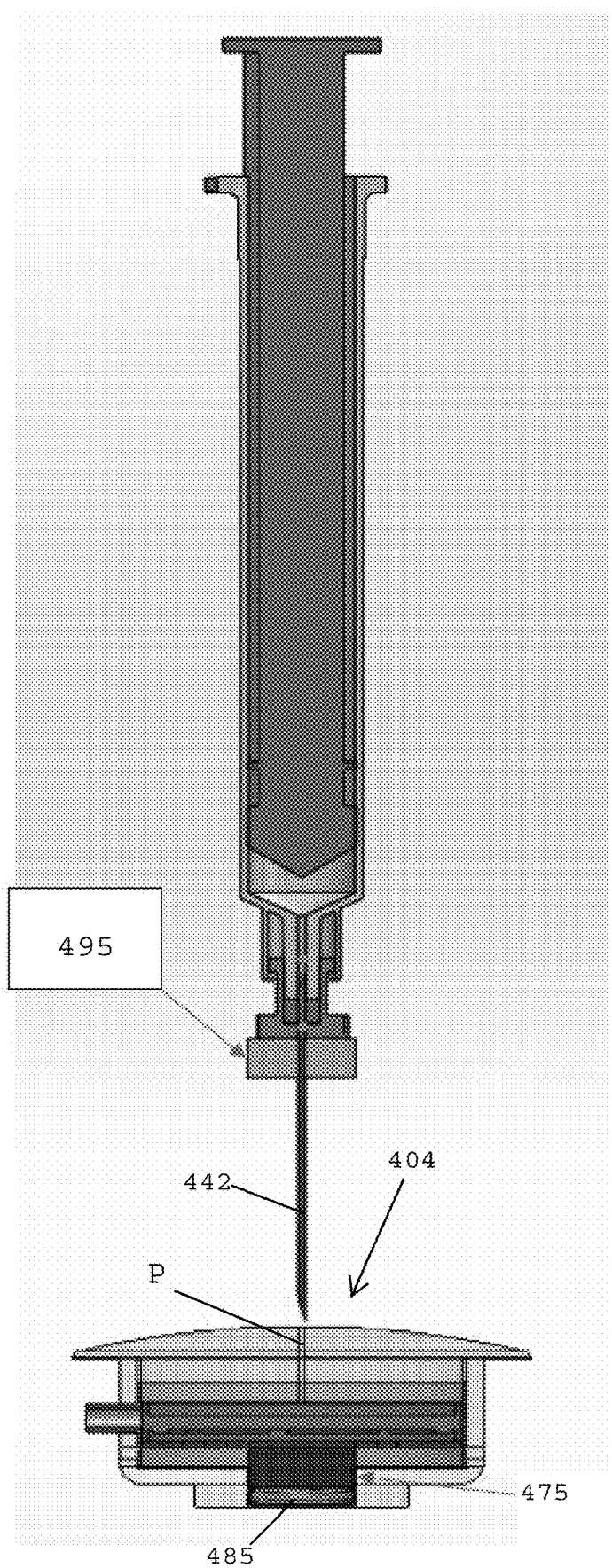
FIG. 14A shows a first step of a method of using the injection port of FIG. 13 for draining fluid from around the perimeter of a tissue expander, in accordance with one embodiment of the present patent application.

Referring to FIG. 14A, in one embodiment, a second magnet 495 may be positioned over the elongated shaft of the injection needle 442. The second magnet 495 may be positioned adjacent a lower end of a syringe. The second magnet 495 preferably generates a magnetic field that repels the first magnet 475 located inside the injection port 440 The repelling forces between the magnets 475, 495 move the movable barrier membrane 422 into the compressed position shown in FIG. 14A, whereupon the barrier rim 422 of the barrier membrane 422 is positioned below an opening of a drainage port 430 so that fluid accumulating around the perimeter of the tissue expander may be withdrawn through the drainage port. FIG. 14A shows a phantom line P that indicates a possible insertion path for the needle 442 when the needle is inserted into the injection port 404.

Figure 14B:
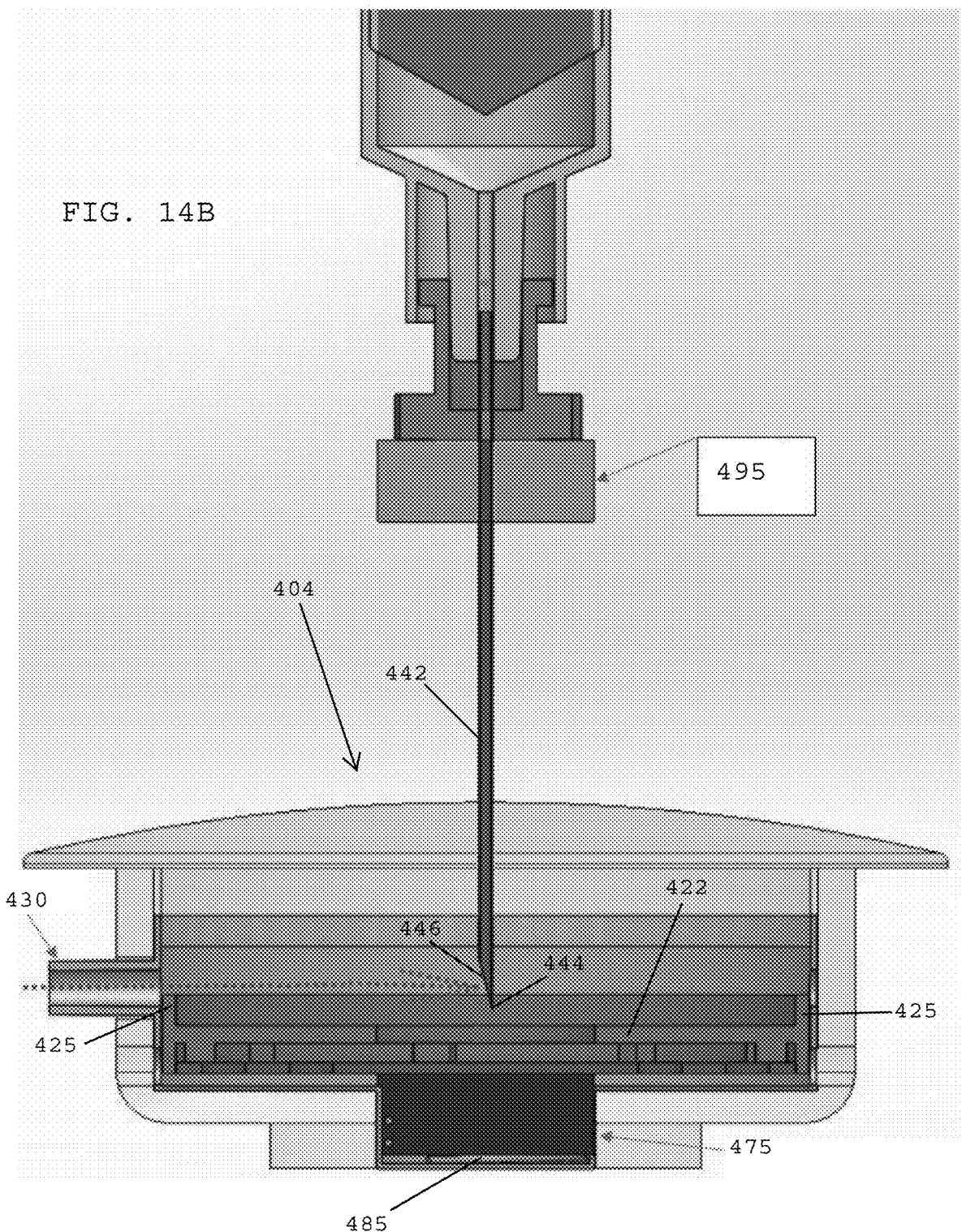
FIG. 14B shows a second step of a method of using the injection port of FIG. 13 for draining fluid from around the perimeter of a tissue expander, in accordance with one embodiment of the present patent application.

Referring to FIG. 14B, the second magnet 495 around the injection needle 442 repels the first magnet 475 within the injection port 404 for compressing the spring 485 and moving the movable barrier membrane 422 into the compressed position. The peripheral rim 425 of the moveable barrier membrane 422 no longer blocks the drainage port 430 so that drainage fluid may be drawn into the opening 446 at the pointed tip 444 of the injection needle 442. As the moveable barrier membrane 422 moves into the lower, compressed position shown in FIG. 14B, the compression spring 485 coupled with an underside of the first magnet 475 is compressed. When the second magnet 495 is moved away from the injection port 404, the energy stored in the compression spring 485 will return the movable barrier membrane 422 back to the extended position shown in FIG. 13. When the movable barrier membrane 422 is returned to the extended position shown in FIG. 13, the peripheral rim 425 of the movable barrier membrane 422 once again blocks the drainage port 430 of the injection port 404 of the tissue expander 400.

Figure 15A:
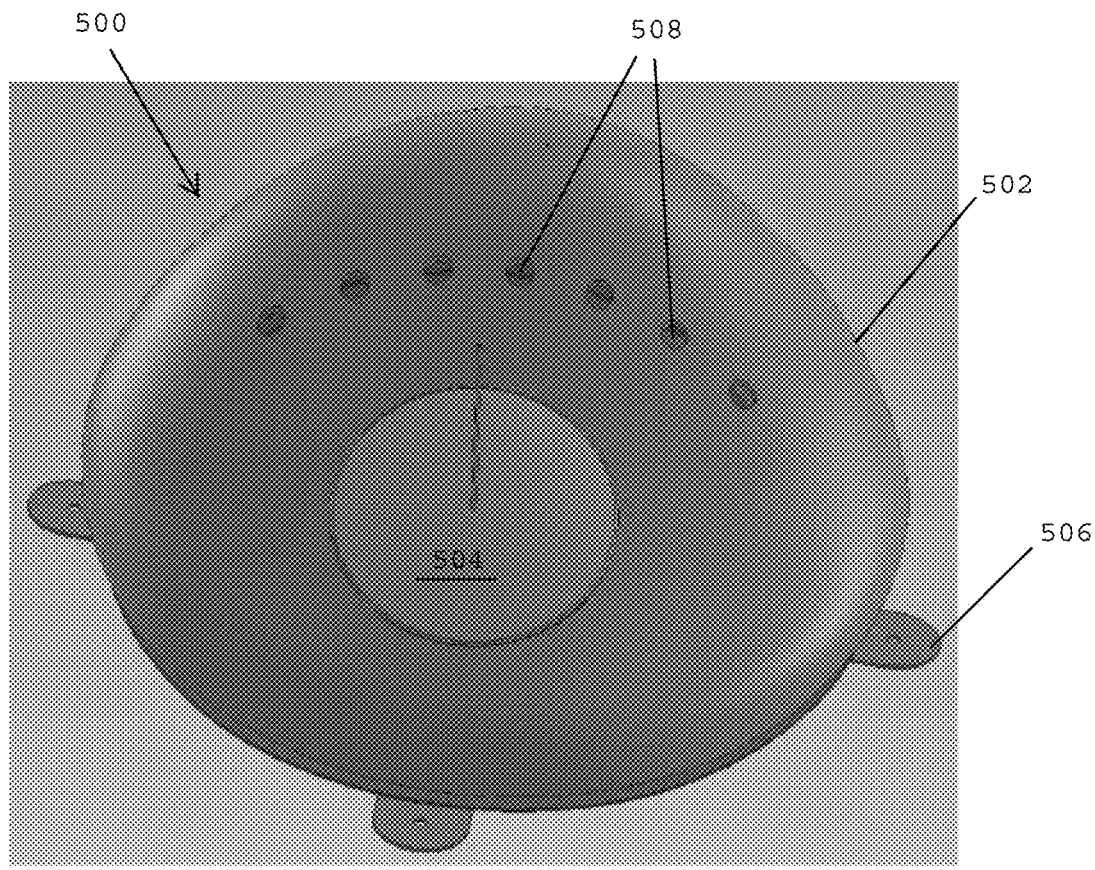
FIG. 15A shows a top view of a tissue expander having an integrated drainage system including drainage holes provided on a top side of an outer shell, in accordance with one embodiment of the present patent application.
Figure 15B:
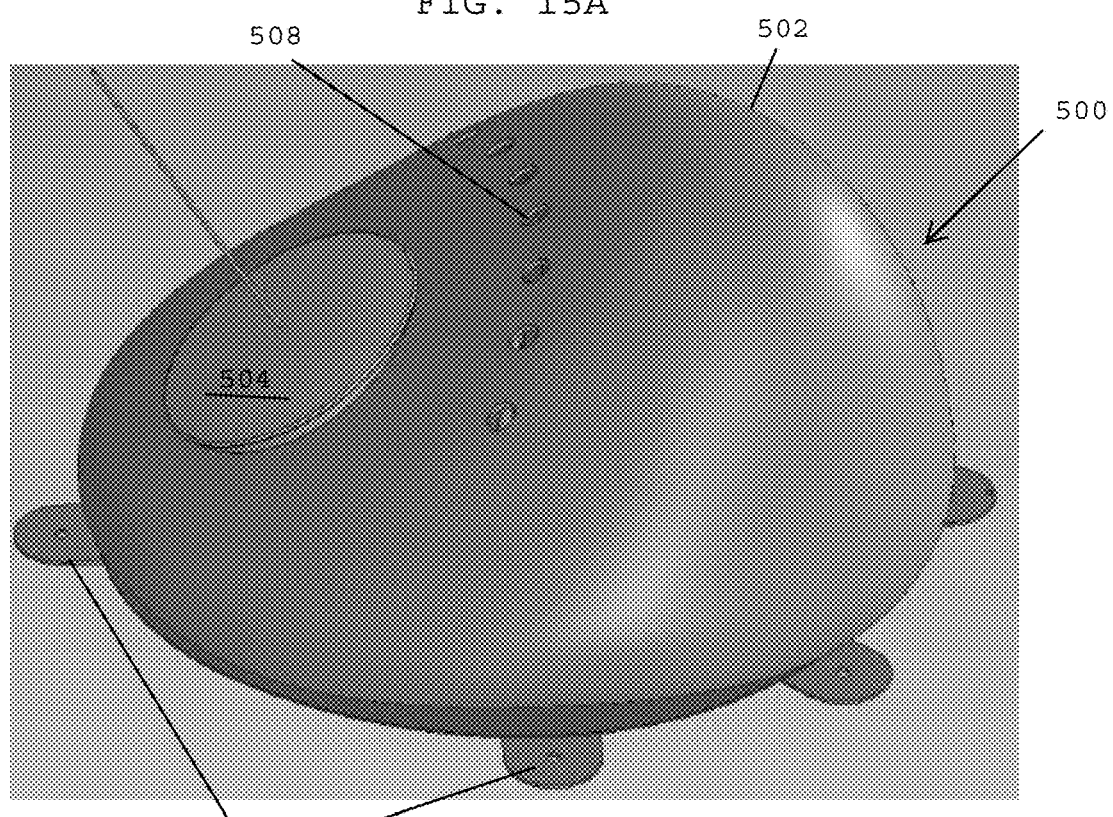
FIG. 15B shows a side perspective view of the tissue expander shown in FIG. 15A.

Referring to FIGS. 15A and 15B, in one embodiment, a tissue expander 500 desirably includes an outer shell 502, and an injection port 504. The tissue expander 500 desirably includes a plurality of holes 508 that are formed in a top side of the outer shell 502. The series of holes 508 may be utilized for draining fluid that accumulates around the outside of the shell 502 and/or or infusing a medical solution through the holes 508 and around the outside of the shell 502. In one embodiment, the tissue expander 500 may include one or more drainage conduits and drains as disclosed herein. In one embodiment, the tissue expander 500 may include one or more infusion conduits as disclosed herein. In one embodiment, the tissue expander 500 may include a drainage conduit in communication with one or more of the holes 508 and an infusion conduit in communication with one or more of the holes 508.

Figure 16A:
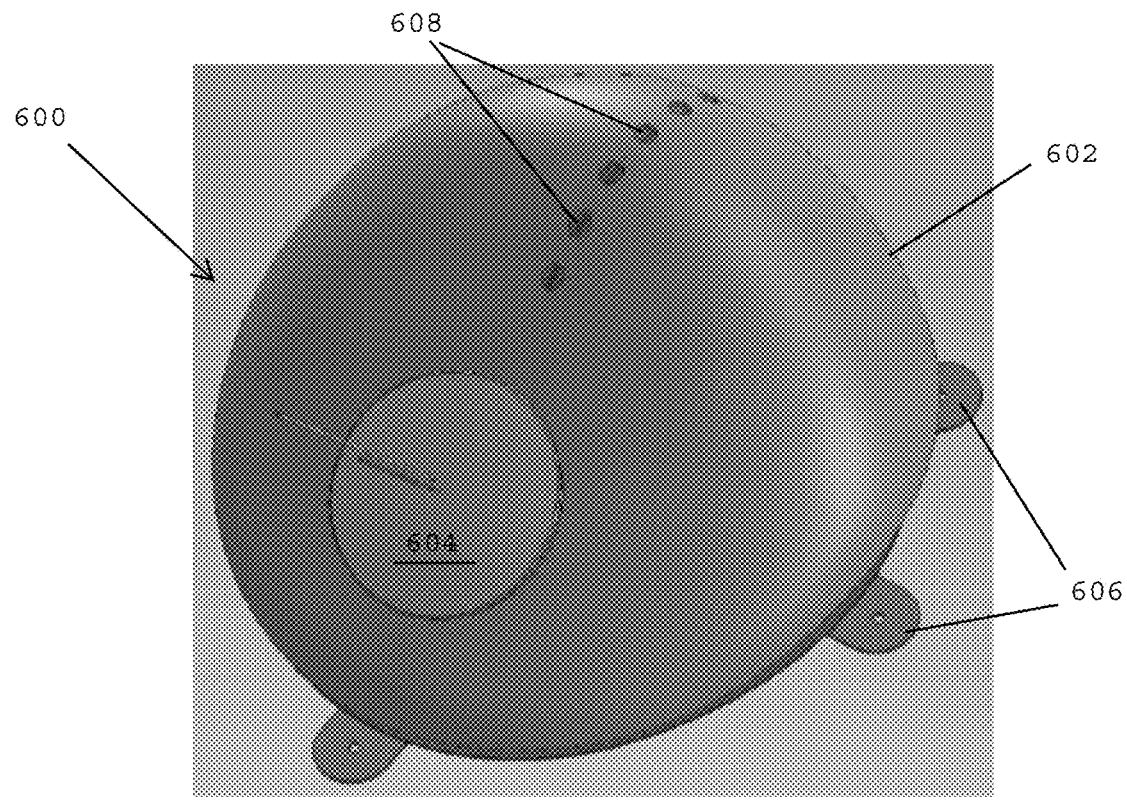
FIG. 16A shows a top perspective view of a tissue expander having an integrated drainage system including radially extending drainage holes, in accordance with one embodiment of the present patent application.
Figure 16B:
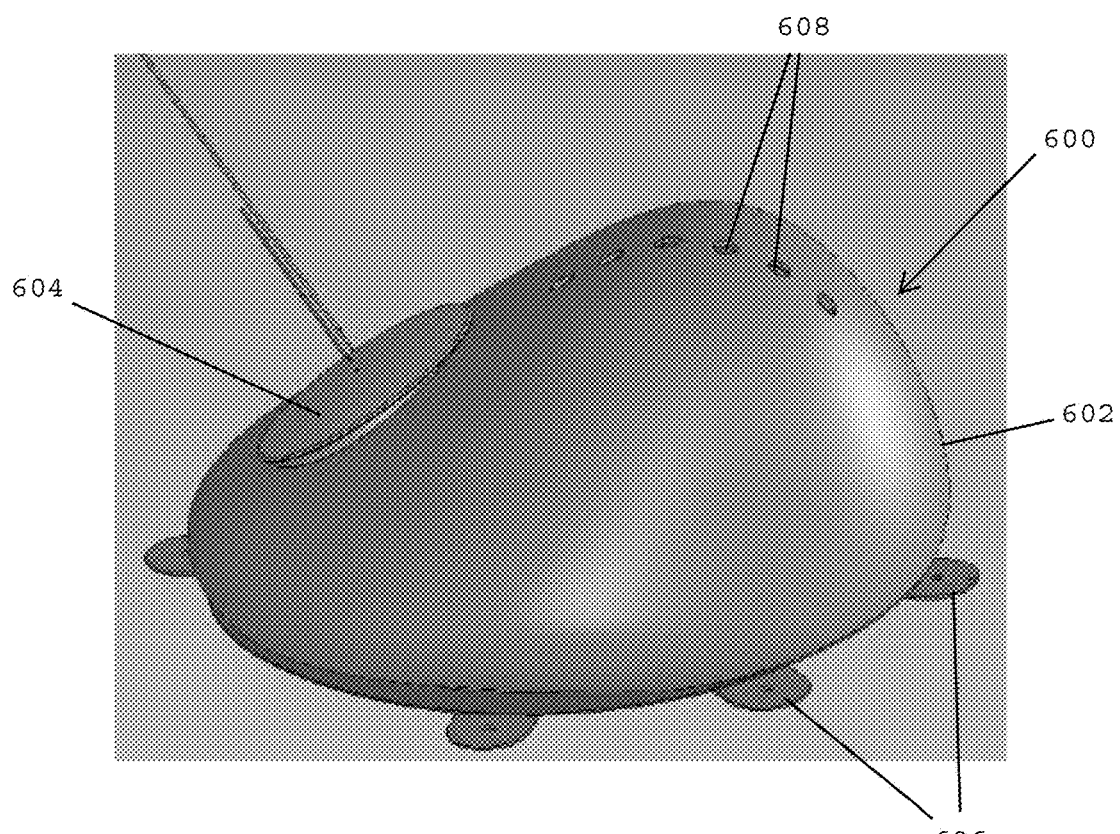
FIG. 16B shows a side view of the tissue expander shown in FIG. 16A.

Referring to FIGS. 16A and 16B, in one embodiment, a tissue expander 600 desirably includes an outer shell 602, and an injection port 604. The tissue expander 600 desirably includes a series of radially extending holes 608 that may be used for draining fluid that has accumulated around the outside of the shell 602 and/or infusing fluid from the holes to flow around the outside of the shell 602.

Figure 17:
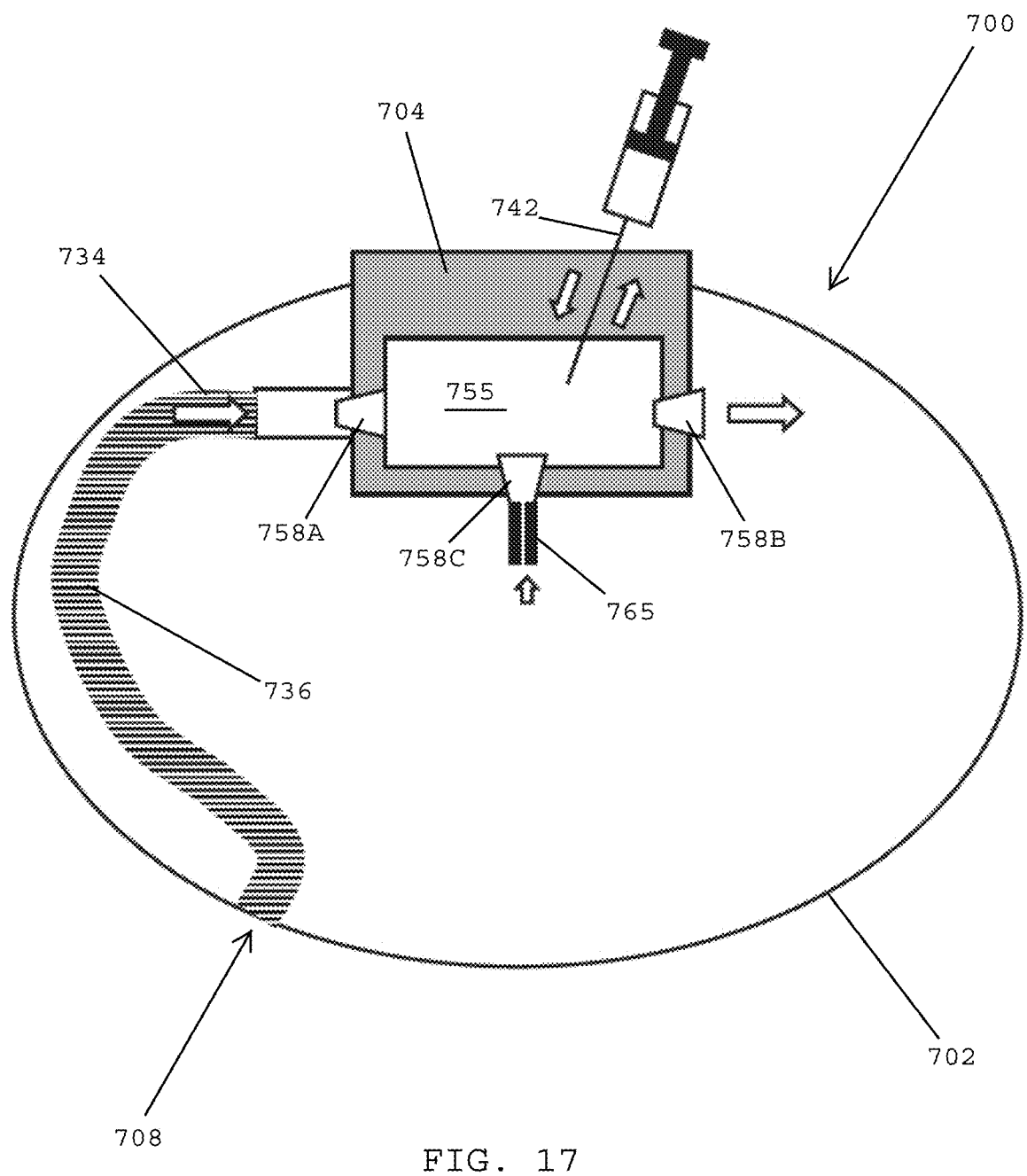
FIG. 17 shows a schematic view of a tissue expander having an integrated drainage system, in accordance with one embodiment of the present patent application.

Referring to FIG. 17, in one embodiment, a tissue expander 700 preferably includes a shell 702 and an injection port 704 that is positioned in an opening of the shell 702. In one embodiment, the shell 702 preferably has a drainage opening 708 formed therein, and a drainage conduit 736 that extends between the drainage opening 708 and the injection port 704.

In one embodiment, the injection port 704 preferably includes an injection compartment 755. A first one-way check valve 758A is positioned between a first end 734 of the drainage conduit 736 and the injection compartment 755. Under vacuum, the first one-way check valve 758A opens for allowing fluid to be drawn into the injection compartment 755, such as by using a needle 742. Under pressure, the first one-way check valve 758A remains closed.

In one embodiment, the tissue expander 700 preferably includes a second one-way check valve 758B that enables inflation fluid (e.g., saline solution) to be introduced into the injection compartment 755 and flow past the second one-way check valve 758B into the interior of the outer shell 702 for inflating the tissue expander 700. The second one-way check valve 758B opens under pressure and remains closed under vacuum. Thus, the first one-way check valve 758A opens under vacuum and the second one-way check valve 758B open under pressure so that the first and second one-way check valves 758A and 758B are not open at the same time. In one embodiment, the same syringe/needle 742 may be used for delivering an inflation fluid into the injection compartment 755 on a forward stroke and evacuating drainage fluid from the injection compartment 755 on a reverse stroke.

In one embodiment, the injection port 704 of the tissue expander 700 desirably includes a third one-way check valve 758C that is located between the injection compartment 755 and an interior region of the shell 702. The third one-way check valve 758C is desirably opened under vacuum, but has a highly restricted aperture 765 so that under vacuum the third one-way check valve 758C will bleed some saline back into the injection compartment 755 for flushing the compartment and to also deflate the tissue expander 700.

Figure 18:
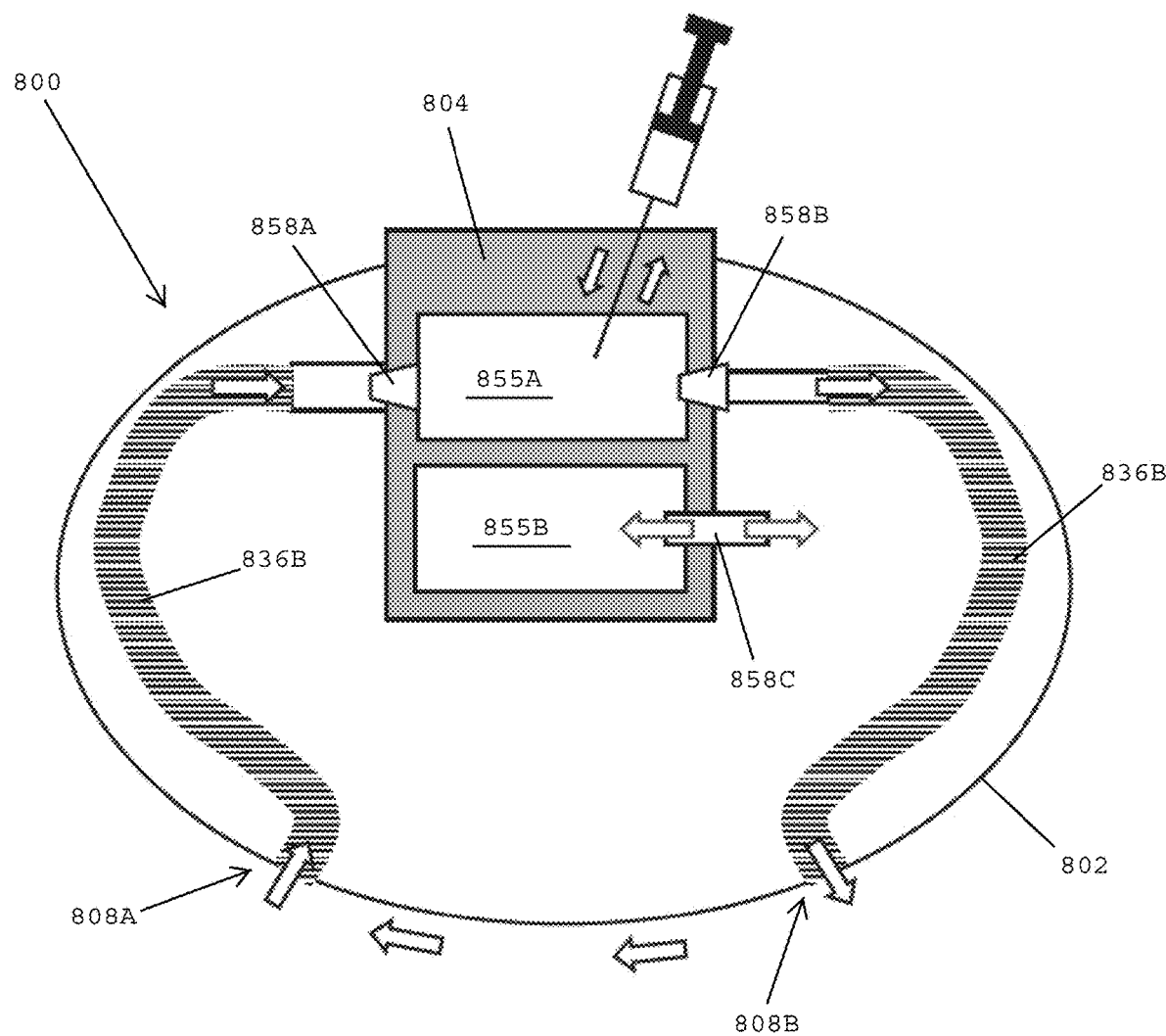
FIG. 18 shows a schematic view of a tissue expander having integrated systems for draining and infusing fluid, in accordance with one embodiment of the present patent application.

Referring to FIG. 18, in one embodiment, a tissue expander 750 desirably includes an outer shell 802 and an injection port 804. The injection port 804 desirably includes a first injection chamber 855A that is in communication with first and second check valves 858A, 858B, and a second injection chamber 855B that is in communication with a third check valve 858C. A membrane 865 divides the first injection chamber 855A from the second injection chamber 855B. A distal end of an injection needle 852 may be passed through the membrane for accessing the second injection chamber 855B to inject a fluid into or remove a fluid from the second ejection chamber 855B.

In one embodiment, the first check valve 858A is coupled with a drainage conduit 836A in communication with a drainage opening 808A formed in the outer shell 802. The second check valve 858B is desirably in communication with an infusion conduit 836B that is coupled with an infusion opening 808B formed in the outer shell 802 of the tissue expander 800. The first one-way check valve 858A opens under vacuum in the first injection chamber 855A for draining fluid that has accumulated around the tissue expander through the drainage opening 808A and the drainage conduit 836A. The drained fluid may be removed from the first injection chamber 855A using a needle 842. The second one-way check valve 858B opens under pressure in the first injection chamber 855A for passing infusion fluid through the infusion conduit 836B to the infusion opening 808B. Thus, in one embodiment, the same syringe 842 may be used to deliver a fluid (e.g., an antibiotic solution) on a forward stroke via the infusion conduit 836B and to evacuate drainage fluid (e.g., seroma) via the drainage conduit 836A and the drainage opening 808A on a reverse stroke.

In one embodiment, the third valve 858C is located in the second injection chamber 855B. The third valve 858C may be used for inflating and deflating the outer shell 802 of the tissue expander 800. Under pressure, fluid in the second injection chamber 855B passes through the third valve 858C for inflating the outer shell 802. Under vacuum, fluid in the outer shell 802 is drawn through the third valve 858C into the second injection chamber 855B where it may be withdrawn using the needle 842.

Figure 19:
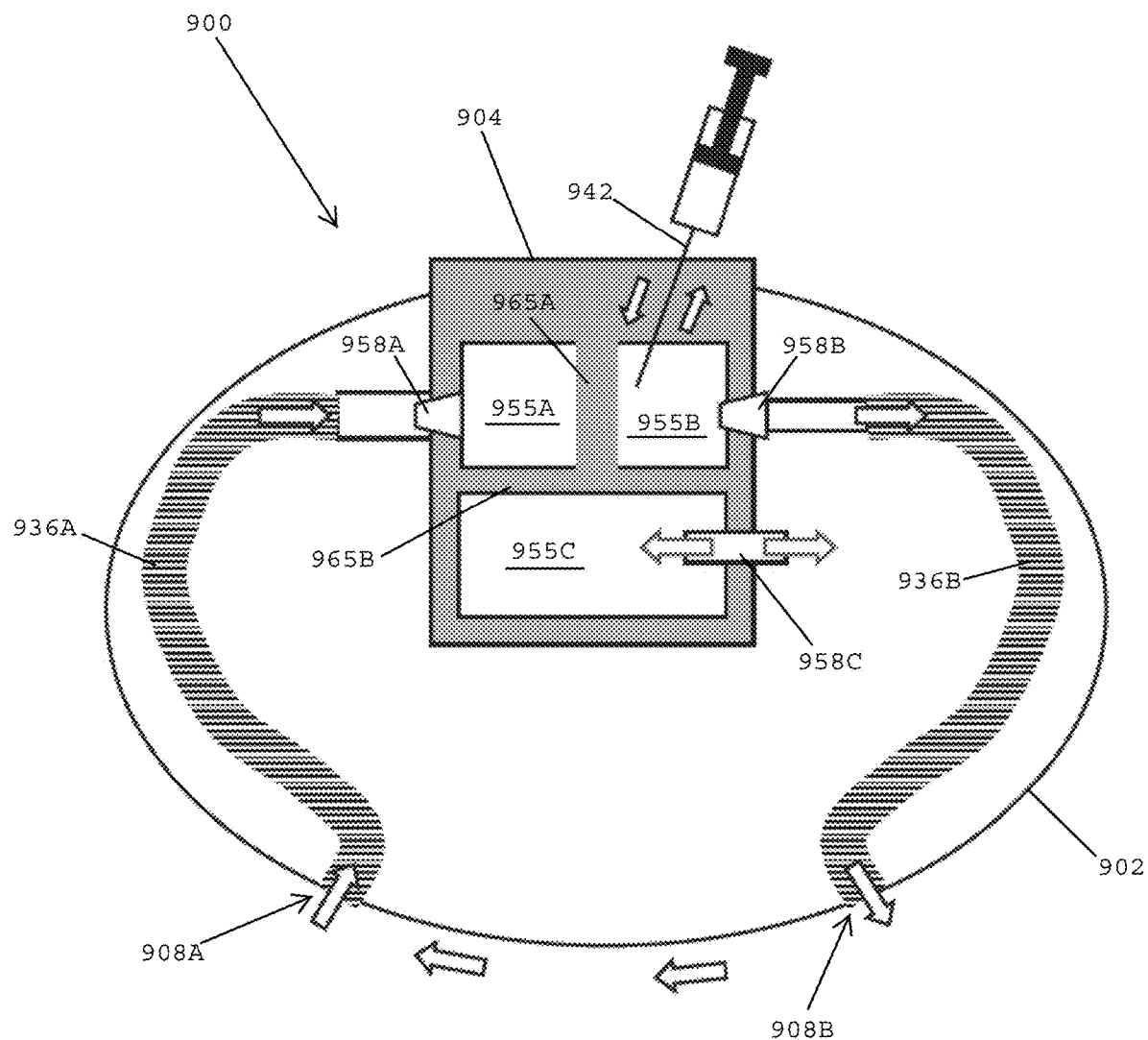
FIG. 19 shows a schematic view of a tissue expander having integrated, inflation, drainage and infusion systems, in accordance with one embodiment of the present patent application.

Referring to FIG. 19, in one embodiment, tissue expander 900 includes an outer shell 902 with an injection port 904. The injection port desirably includes a first injection chamber 955A that is in communication with a drainage conduit 936A, and a second injection chamber 955B that is in communication with an infusion conduit 936B. In one embodiment, a first membrane 965A separates the first and second injection chambers 955A and 955B from one another. In one embodiment, the injection port 904 may include injection zone markers for locating and distinguishing between the first and second injection chambers 955A and 955B, as disclosed in commonly assigned U.S. Pat. No. 9,636,210 to Hristov et al., the disclosure of which is hereby incorporated by reference herein. The injection zone makers may be made of a material having ultrasonically detectable markers incorporated therein. In one embodiment, the markers may include a plurality of microcavities that are located relative to the first and second injection chambers of the injection port so that, when ultrasonically detected, such detection includes the locations of the first and second injection chambers.

The tissue expander 900 desirably includes a first check valve 958A that is coupled with a first end of the drainage conduit 936A. The drainage conduit 936A, in turn, is coupled with a drainage hole 908A provided in the outer shell 902. Under vacuum within the first injection chamber 955A, the first check valve 958A opens for allowing drainage fluid to be drawn through the drainage opening 908A, the drainage conduit 936A, and the first one-way check valve 958A, and into the first injection chamber 885A for being withdrawn from the first injection chamber using a needle 892.

The second check valve 958B is provided at a first end of the infusion conduit 936B. The infusion conduit 936B has a second end that is coupled with an infusion hole 908B formed in the outer shell 902. Under pressure within the second injection chamber 955B, the second one-way check valve 958B opens for allowing fluid injected into the second injection chamber 955B to pass by the second valve 908B, through the infusion conduit 936B and out of the infusion hole 908B for infusing the outer surface of the shell with a fluid.

In one embodiment, the third injection chamber 955C may be utilized for introducing fluid into the outer shell 852 for expanding the size of the tissue expander or withdrawing fluid from the outer shell 902 for reducing the size (i.e., deflating) the tissue expander 900. In one embodiment, the tissue expander 900 desirably includes a third valve 958C coupled with the third injection chamber 955C. A second membrane 965B separates the first and second injection chambers 955A, 955B from the third injection chamber 955C. A needle 942 may be passed through the first and second membranes for selectively accessing each of the injection chambers 955A-955C. Under pressure, the third check valve 908C opens for allowing solution, such as saline solution, to flow through the valve 908C and into outer shell 902 for inflating the tissue expander 900. Under vacuum, the third check valve 958C opens for drawing fluid from the outer shell 902 into the third injection chamber 955C for reducing the size of the tissue expander.

Figure 20:
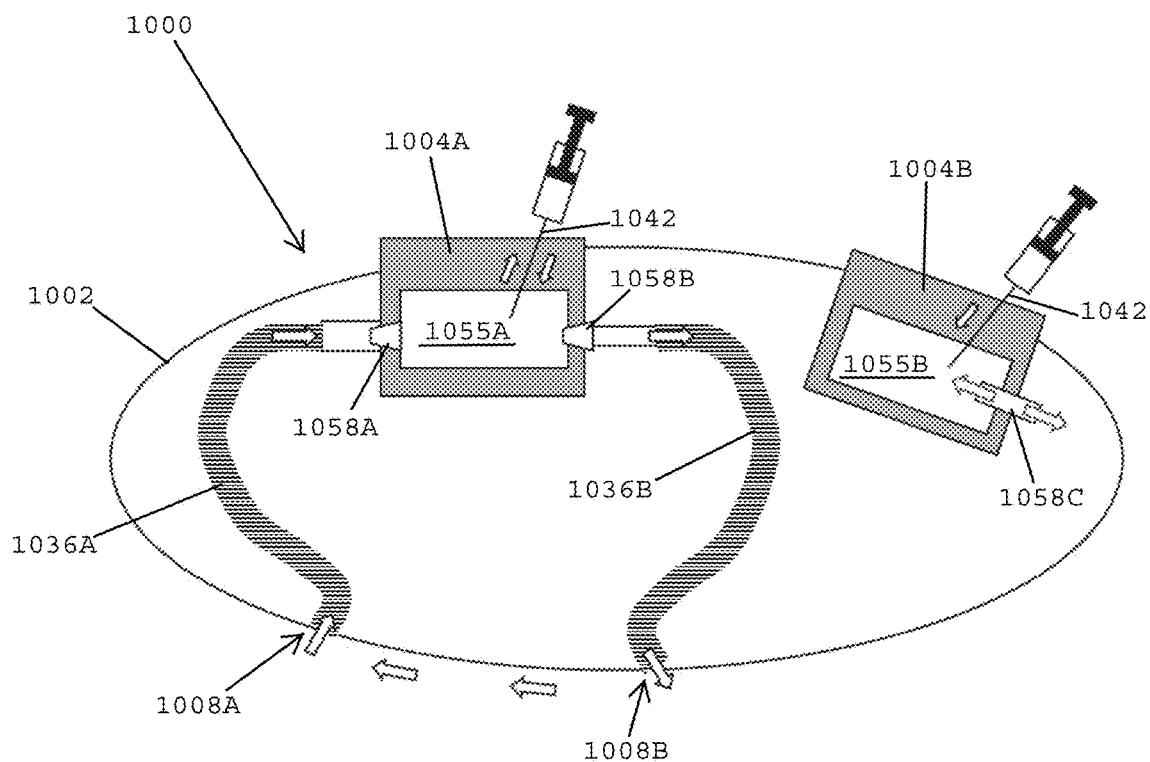
FIG. 20 shows a tissue expander having a first injection port for draining and infusing fluid, and a second ejection port for inflating the tissue expander with a solution, in accordance with one embodiment of the present patent application.

Referring to FIG. 20, in one embodiment, a tissue expander 1000 desirably includes an outer shell 1002 with a first injection port 1004A and a second injection port 1004B secured to the outer shell 1002. In one embodiment, the first injection port 1004A includes a first injection chamber 1055A in communication with a first check valve 1058A and a second check valve 1058B. In one embodiment, the tissue expander 1000 includes a first drainage conduit 1036A having a first end coupled with a drainage port in communication with the first check valve 1058A. The drainage conduit 1036A preferably includes a second end that is coupled with a drainage hole 1008A formed in the outer shell 1002 of the tissue expander 1000. In one embodiment, when a vacuum is drawn inside the first injection chamber 1055A, the first check valve 1058A opens for allowing any fluid that has accumulated around the exterior of the tissue expander 1000 to be drawn through the drainage hole 1008A, through the drainage conduit 1036A, past the open first check valve 1058A and into the first injection chamber 1055A for being withdrawn from the first injection chamber using a needle 1042.

In one embodiment, the second check valve 1058B is disposed between the first injection chamber 1055A and the first end of an infusion conduit 1036B. The infusion conduit 1036B has a second end connected with an infusion hole 1008B provided in the outer shell 1002 of the tissue expander 1000. In one embodiment, when pressure is provided inside the first injection chamber 1055A, the second check valve 1058B opens for allowing infusion fluid to flow by the second check valve 1058B, through the infusion conduit 1036B and out of the infusion hole 1008B for bathing the exterior of the outer shell 1002 with an infusion fluid.

In one embodiment, the second injection port 1004B of the tissue expander 1000 may be utilized for inflating and deflating the outer shell 1002 of the tissue expander 1000. In one embodiment, the second injection port 1004B desirably includes a second injection chamber 1055B and a third valve 1058C that opens under both pressure and vacuum. In one embodiment, when inflation fluid is injection via needle 1042 into the second injection chamber 1055B, the fluid under pressure opens the third check valve 1058C and the fluid passes into the interior region of the outer shell 1002 for inflating the tissue expander 1000. When a vacuum is drawn in the second injection chamber 1055B, the third check valve 1058C opens to allow the fluid inside the outer shell 1002 be drawn into the second injection chamber 1055B for being removed from the outer shell 1002 to deflate the tissue expander 1000.

Figure 21:
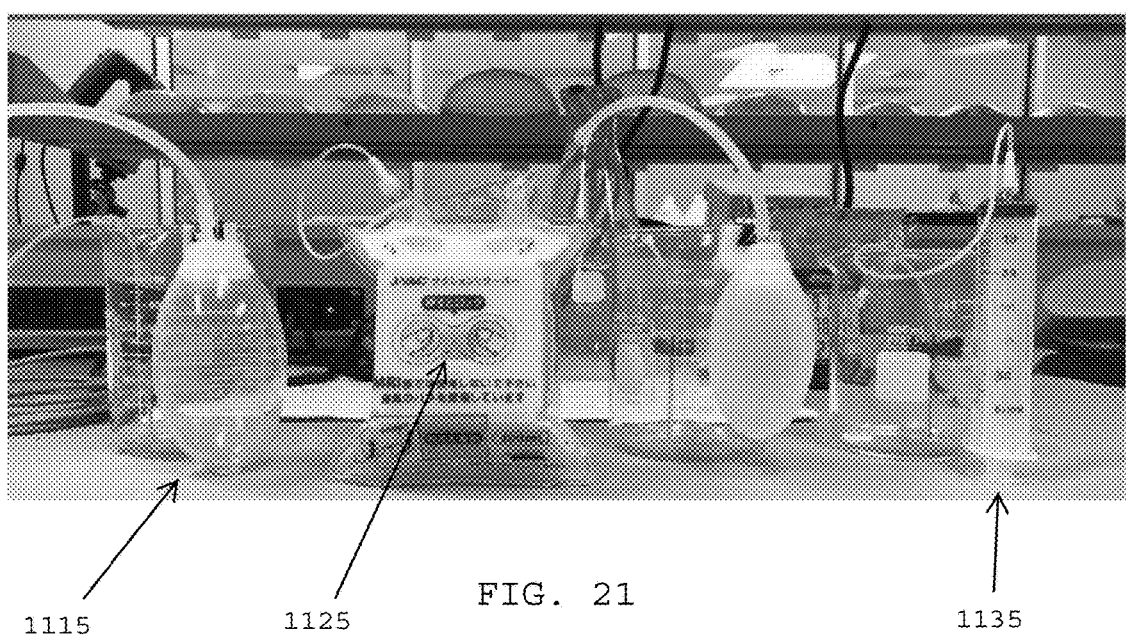
FIG. 21 shows systems for creating vacuum for draining fluids that collect around tissue expanders, in accordance with one embodiment of the present patent application.

FIG. 21 shows various systems and devices that may be used for creating a vacuum to drain fluid that has accumulated around the tissue expanders disclosed herein after the tissue expanders have been implanted inside patients. The devices may be coupled with the drainage conduits, injections chambers, and/or injection ports disclosed herein for drawing any fluid that has accumulated around the outsides of the outer shells of the respective tissue expanders. In one embodiment, In one embodiment, a system for generating a vacuum preferably includes a compressible bulb 1115. In one embodiment, vacuum may be created using a flexible, compressible reservoir 1125 that draws a substantially constant vacuum to permit uniform removal of fluid from a surgical incision through a wound drain catheter, such as the surgical fluid evacuator disclosed in U.S. Pat. No. 4,429,693 to Blake et al., the disclosure of which is hereby incorporated by reference herein. In one embodiment, a system having a metered container 1035 may be used for drawing a vacuum to permit the uniform removal of fluid from a surgical site.

Figure 22A:
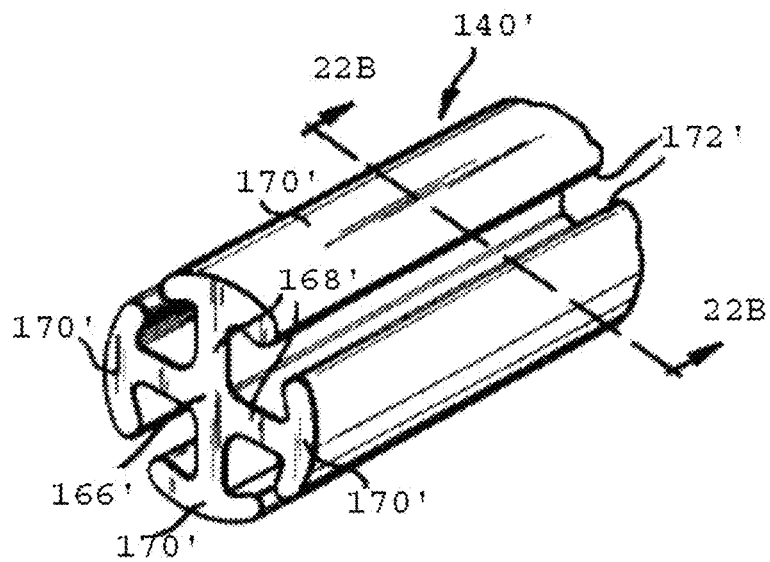
FIG. 22A shows a perspective view of a drain that is adapted for assembly with the drainage manifold of FIGS. 5A and 5B, in accordance with one embodiment of the present patent application.
Figure 22B:
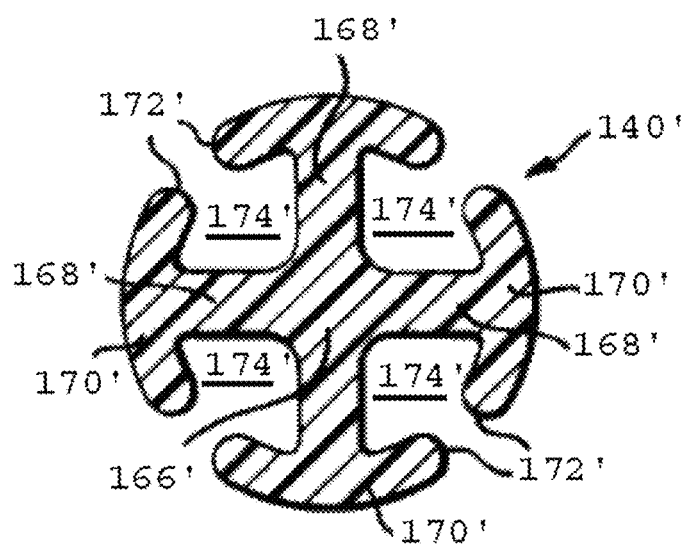
FIG. 22B shows a cross-sectional view of the drain shown in FIG. 22A.

Referring to FIGS. 22A and 22B, in one embodiment, a drain 140' preferably has an elongate, cylindrical core 166' with four struts 168' that project radially from the core 166' along the longitudinal axis of the core. The radial struts 168' are preferably of equal size and are spaced at equal angles relative to one another. Each of the outer ends of the radial struts 168' have respective overhang portions 170' which extend longitudinally throughout the length of the radial struts 168'. As shown in FIG. 6B, in one embodiment, the overhang portions 170' are thin arcuate members that extend an equal distance on either side of their respective radial struts 168'. Thus, the overhand portions 170' and the respective radial struts 168' combine to form four T-shaped members. The overhang portions 170' are sized to form a segmented circle at the periphery of the drain 140', with small gaps between the adjacent overhang portions 170'. Each of these gaps forms a longitudinal groove 172', parallel to the longitudinal axis of the core 166', and extending throughout the length of the drain 140'. The core portion 166', the radial struts 168', and the overhand portions 170' cooperate to form plural channels or lumens 174' that extend along the length of the drain 140'. The longitudinal grooves 172' permit fluid communication between the respective lumens 174' and a wound. In one embodiment, the width of the longitudinal grooves 172' is approximately 0.05-0.2 times the outside diameter of the drain 140', which ensures adequate tissue contact in the drainage area while inhibiting tissue growth or entry of debris, such as clots, into the lumens 174'.

After breast reconstruction surgery, patients will have surgical drains placed to prevent blood and lymphatic fluid from building up under the skin, allowing for a quicker recovery. Some patients are sent home with drains that are implanted and connected to an external reservoir. Emptying these reservoirs can be traumatic as they have to measure and empty the reservoirs every morning. Patients cannot wait to have drains removed. Having a means to remove seroma fluid without the need for a drain being attached 24 hours a day is a great benefit to the patient.

Figure 23A:
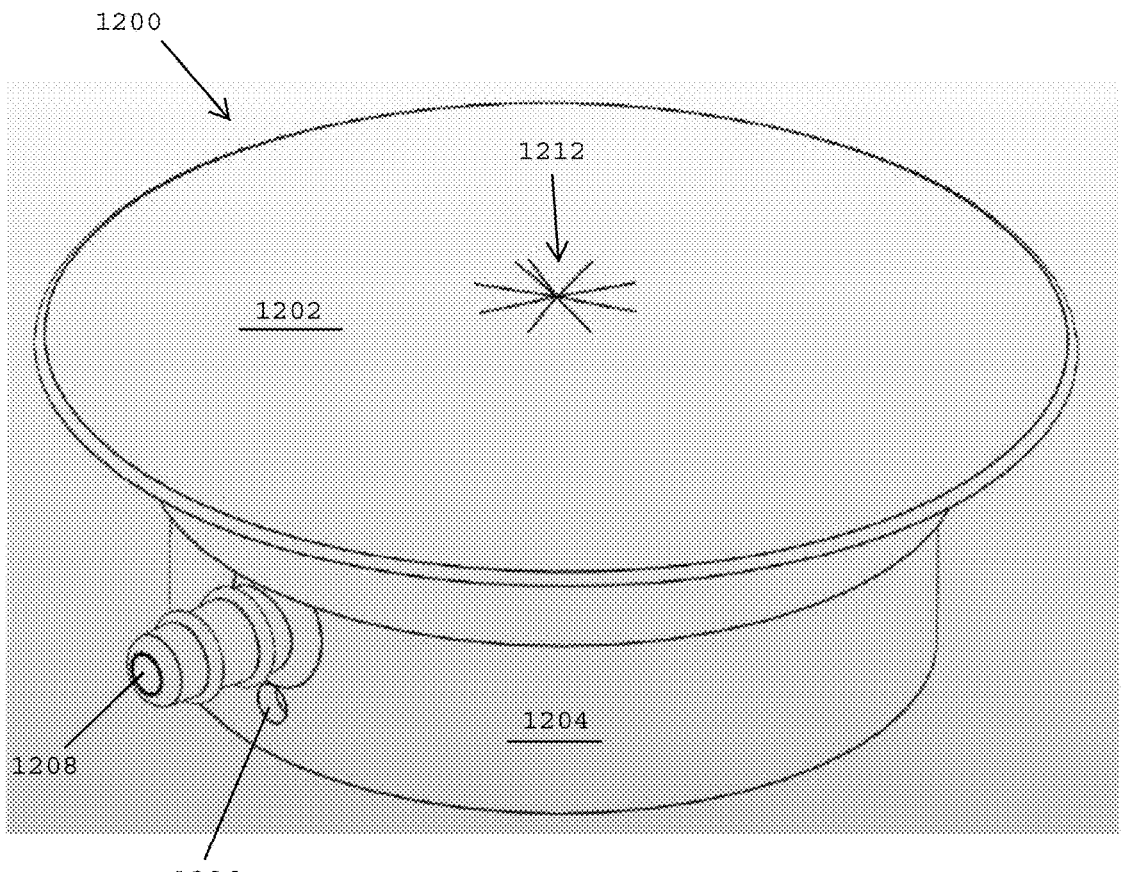
FIG. 23A is a perspective view of an injection port assembly including a needle guard and an injection dome, in accordance with one embodiment of the present patent application.
Figure 23B:
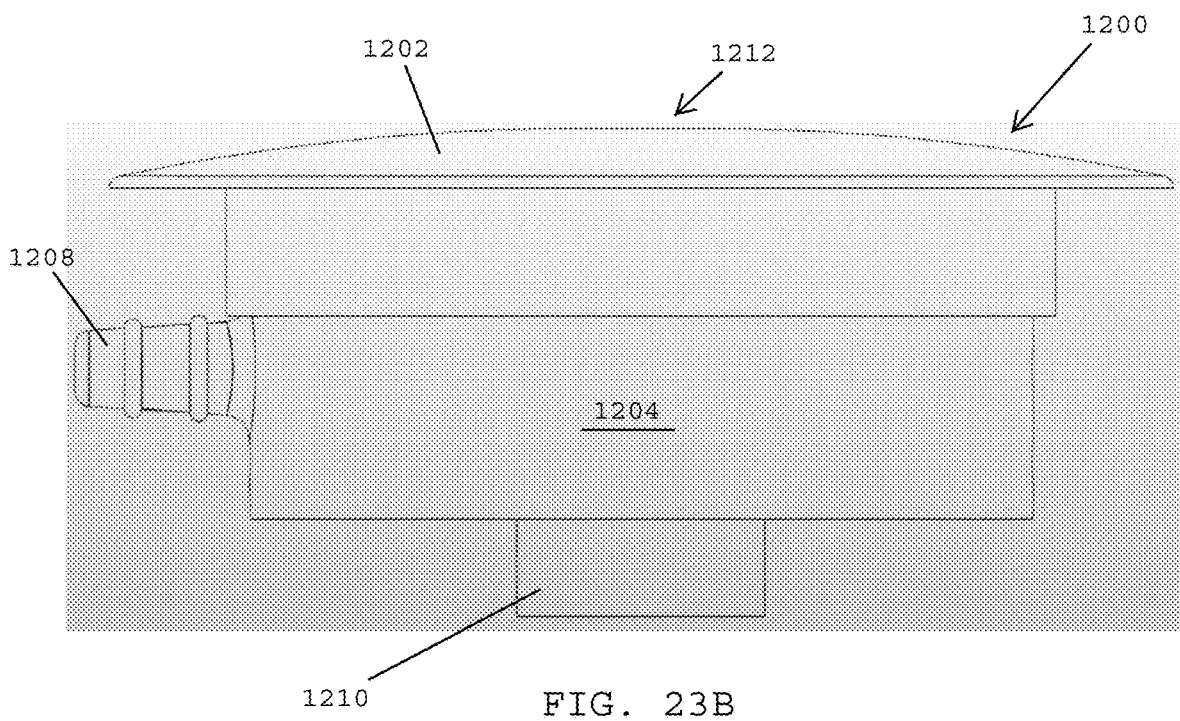
FIG. 23B is a side elevation view of the needle guard and the injection dome shown in FIG. 23A.

Referring to FIGS. 23A and 23B, in one embodiment, an injection port assembly 1200 for an implant such as a tissue expander or a mammary implant preferably includes an injection dome 1202 that is secured over an upper end of a needle guard 1204 having one or more inflation ports 1206 that are in fluid communication with an inflation chamber located inside the needle guard 1204, and a drainage port 1208 that is in fluid communication with a drainage chamber located inside the needle guard 1204. The injection port assembly 1200 may have one or more of the components and/or features disclosed in the injection port assembly 104 shown and described above in FIG. 3 of the present patent application.

Referring to FIG. 23B, in one embodiment, the injection port assembly 1200 may include a magnet case 1210 secured to an underside of the needle guard 1204. In one embodiment, the magnet case 1210 desirably contains a magnet (not shown) that may be utilized by medical personnel for locating the center 1212 of the injection dome 1202. After the injection port 1200 has been implanted inside a patient (e.g., as part of a breast reconstruction procedure), the magnet disposed inside the magnet case 1210 preferably enables medical personnel to locate the center 1212 of the injection dome 1202 so that a needle inserted into the injection dome 1202 will be located inside the perimeter of the needle guard 1204 and will not extend outside the needle guard where the needle could damage the shell of the implant or injure the patient.

Referring to FIGS. 24A-24D, in one embodiment, the needle guard 1204 preferably includes a needle guard rim 1214 having an upper end 1216 and a lower end 1218. In one embodiment, the upper end 1216 of the needle guard rim 1214 is desirably open and adapted for receiving an underside of the injection dome 1202 (FIG. 23A) as will be described in more detail herein. In one embodiment, the needle guard 1204 desirably has a needle guard base 1220 that is located at the lower end 1218 of the needle guard rim 1214 for closing the bottom of the needle guard 1204. In one embodiment, the needle guard rim 1214 may have a cylindrical shape.

Figure 24A:
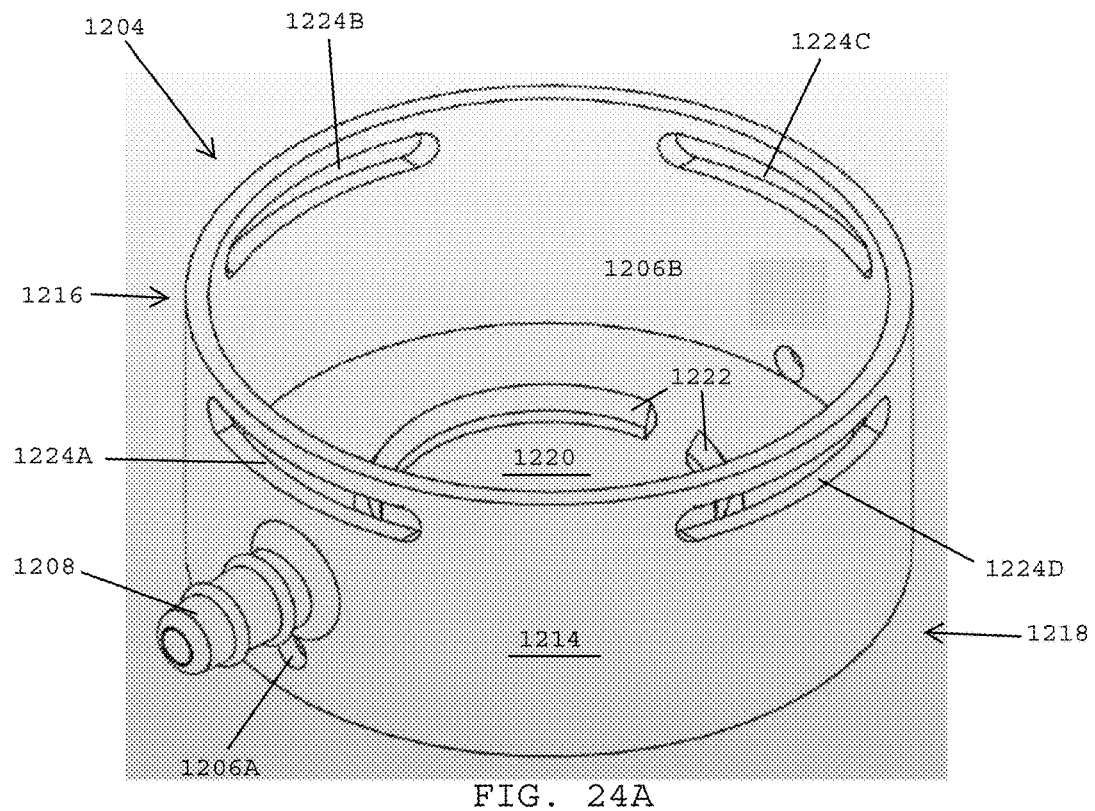
FIG. 24A is a perspective view of a top side of the needle guard shown in FIGS. 23A and 23B, in accordance with one embodiment of the present patent application.
Figure 24B:
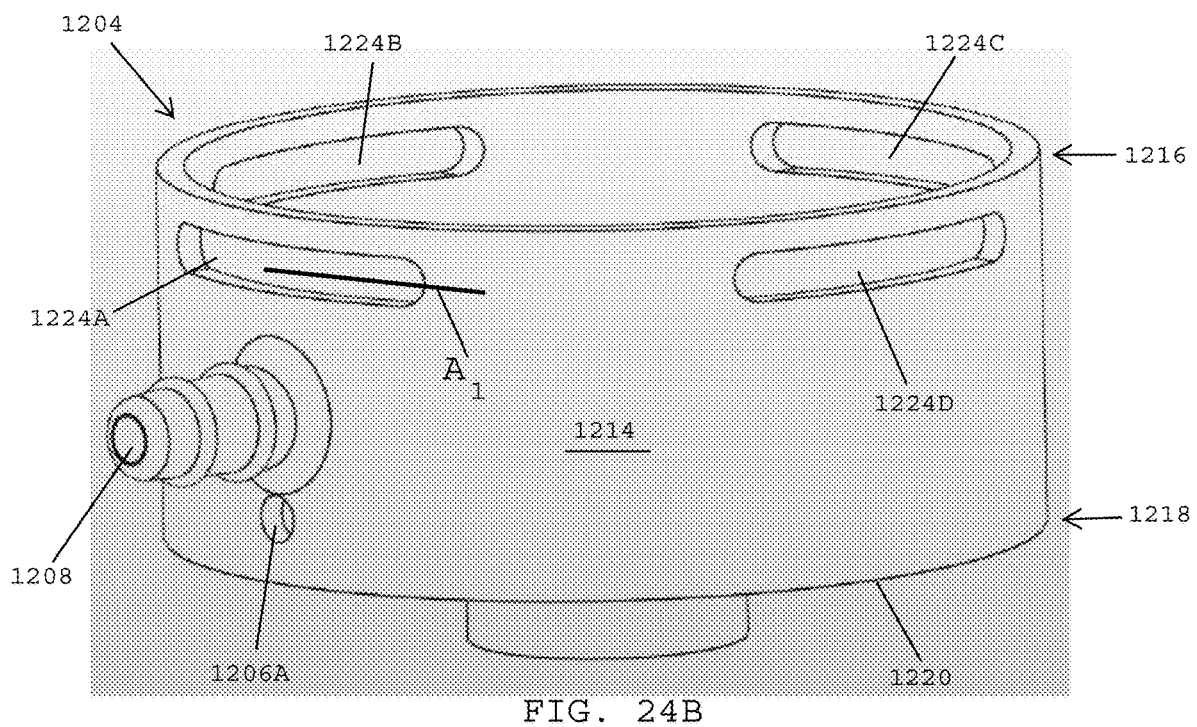
FIG. 24B is another perspective view of the needle guard shown in FIG. 24A.
Figure 24C:
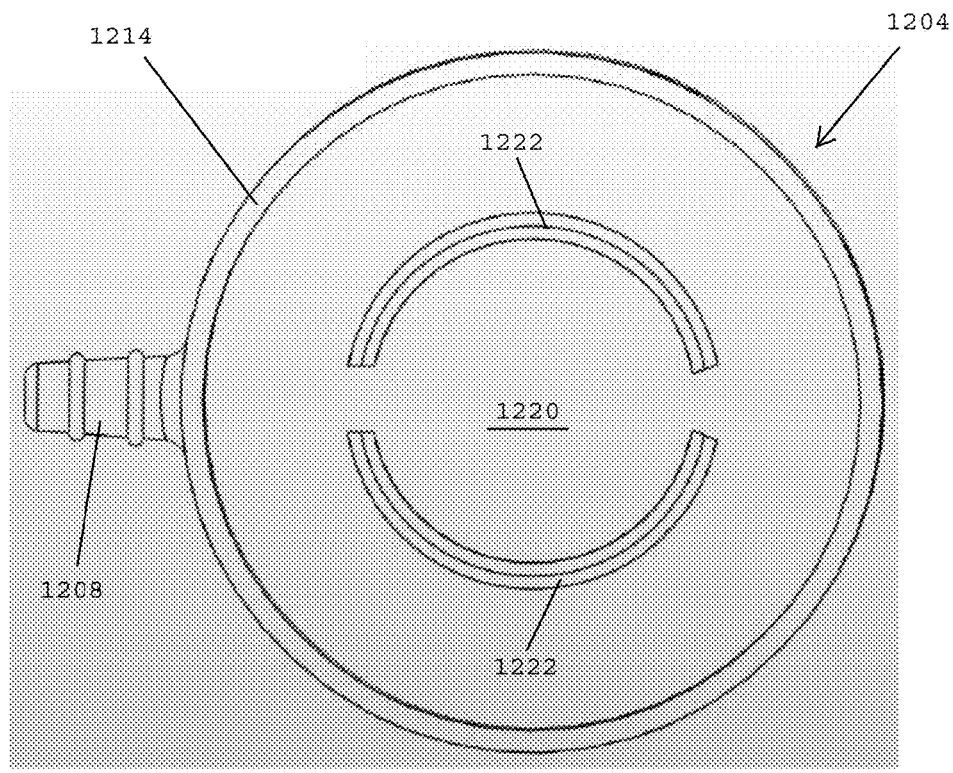
FIG. 24C is a top plan view of the needle guard shown in FIGS. 24A and 24B.
Figure 24D:
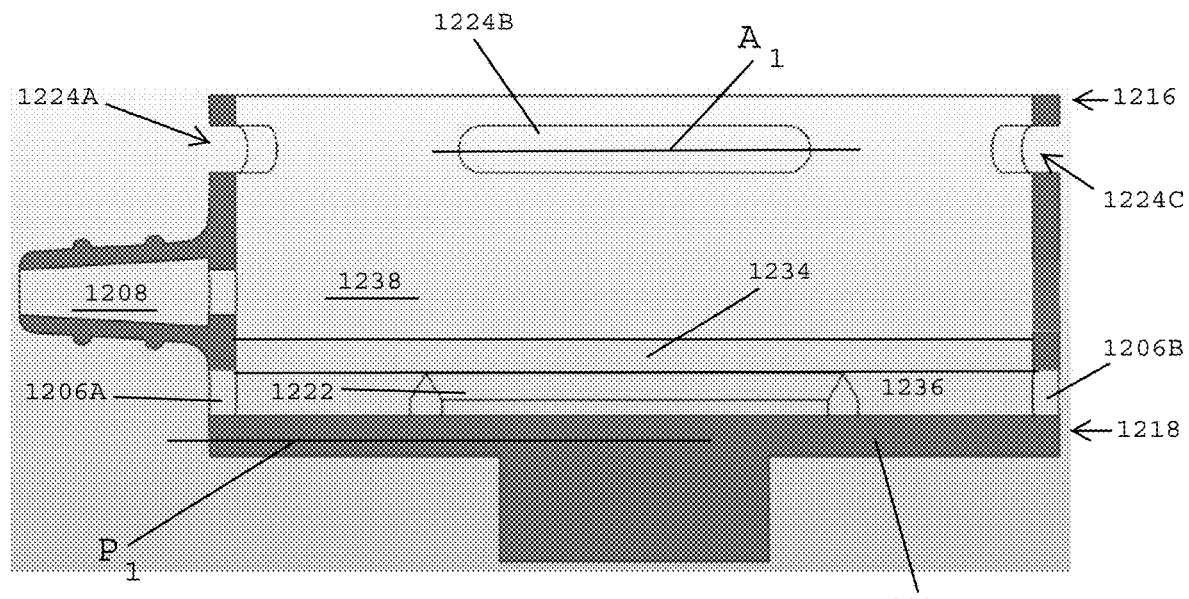
FIG. 24D is a cross-sectional view of the needle guard shown in FIGS. 24A-24C.

Referring to FIGS. 24A, 24C and 24D, in one embodiment, the needle guard base 1220 of the needle guard 1204 preferably includes a barrier membrane support 1222 that projects upwardly from the needle guard base 1220 of the needle guard 1204. The barrier membrane support 1222 preferably supports an underside of a barrier membrane to prevent tenting and/or collapsing of the barrier membrane when a distal end of a needle is pressed against and/or into the barrier membrane. In one embodiment, the barrier membrane support 1222 preferably has a circular shape. The barrier membrane support may include two or more elements that are spaced from one another (e.g., opposing half circles). In one embodiment, the barrier membrane support may include a plurality of spaced posts that project from a top surface of the needle guard base 1220, which have upper ends that are adapted to engage a barrier membrane, such as a bottom surface of the barrier membrane, for supporting the barrier membrane inside the injection dome 1204.

Referring to FIGS. 24A, 24B, and 24D, in one embodiment, the needle guard rim 1214 of the needle guard 1204 preferably includes a series of elongated slots 1224A-1224D that pass through the needle guard rim 1214 adjacent the upper end 1216 of the needle guard rim 1214. In one embodiment, the elongated slots 1224A-1224D desirably extend along longitudinal axes $A_1$ (FIG. 24D) that are parallel with a plane $P_1$ (FIG. 24D) defined by the needle guard base 1220 of the needle guard 1204.

Referring to FIGS. 24A, 24B and 24D, in one embodiment, the needle guard 1204 desirably includes inflation ports 1206A, 1206B that are formed in the needle guard rim 1214 and that are in fluid communication with the inflation chamber of the injection port assembly 1200 (FIG. 23B). The needle guard 1204 preferably includes a drainage port 1208 that desirably passes through the needle guard rim 1214 and is in fluid communication with the drainage chamber of the injection port assembly. Referring to FIG. 24D, in one embodiment, a barrier membrane 1234 is located inside the needle guard 1204 for isolating the inflation chamber 1236 from the drainage chamber 1238. In one embodiment, the barrier membrane support 1222 desirably supports an underside of the barrier membrane 1234 for preventing the barrier membrane from tenting when a distal end of a needle assembly is pressed against the barrier membrane 1234.

Figure 25A:
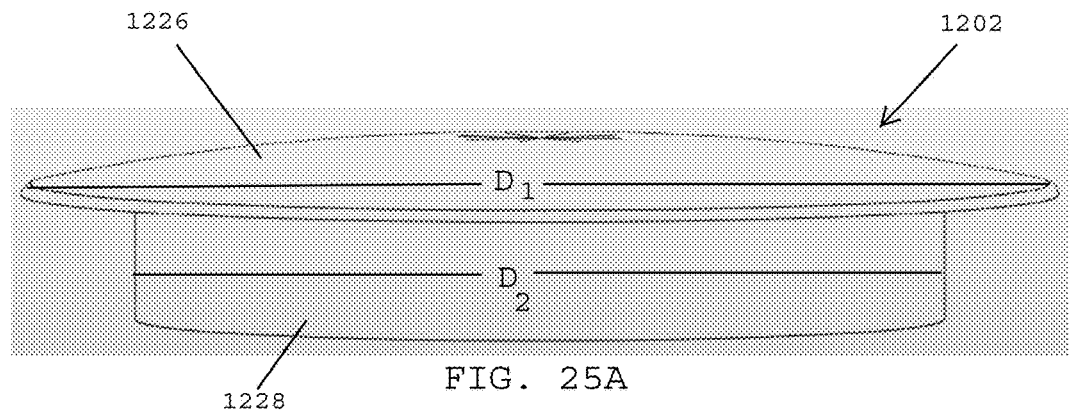
FIG. 25A is a side elevation view of the injection dome shown in FIGS. 23A and 23B.
Figure 25B:
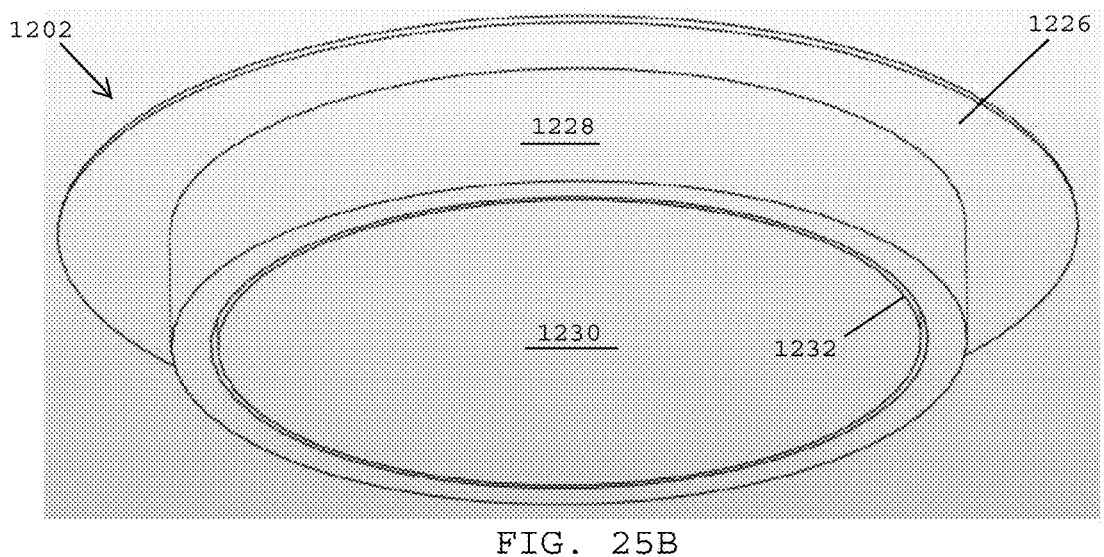
FIG. 25B is a perspective view of an underside of the injection dome shown in FIG. 25A.
Figure 25C:
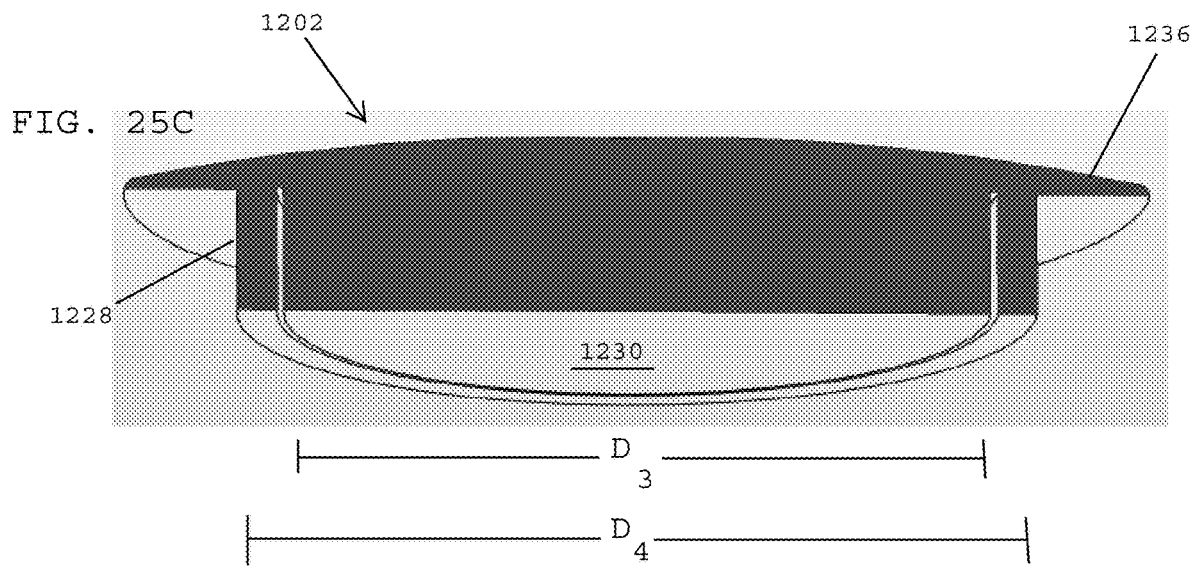
FIG. 25C is a partial cross-sectional view of the injection dome shown in FIGS. 25A and 25B.

Referring to FIGS. 25A-25C, in one embodiment, the injection dome 1202 preferably has a lid 1226 defining a first diameter $D_1$ and a base 1228 that extends from an underside of the lid 1226 having a second diameter $D_2$ that is smaller than the first diameter D1. In one embodiment, the lid 1226 has a circular shape and the base 1228 has a circular or cylindrical shape.

In one embodiment, the base 1228 of the injection dome 1202 has a bottom surface 1230 having an annular groove 1232 formed therein, which is adapted to receive the upper end 1216 of the needle guard rim 1214 of the needle guard 1204 (FIG. 24B) for securing the injection dome to the needle guard. Referring to FIGS. 25B and 25C, the annular groove 1232 formed in the bottom surface 1230 of the base 1228 extends from the bottom surface 1230 toward the lid 1226 of the injection dome 1202. Referring to FIG. 25C, in one embodiment, the annular groove 1232 preferably defines a third diameter $D_3$ that is smaller than the second diameter $D_2$ of the base 1228 of the injection dome 1202.

Figure 26:
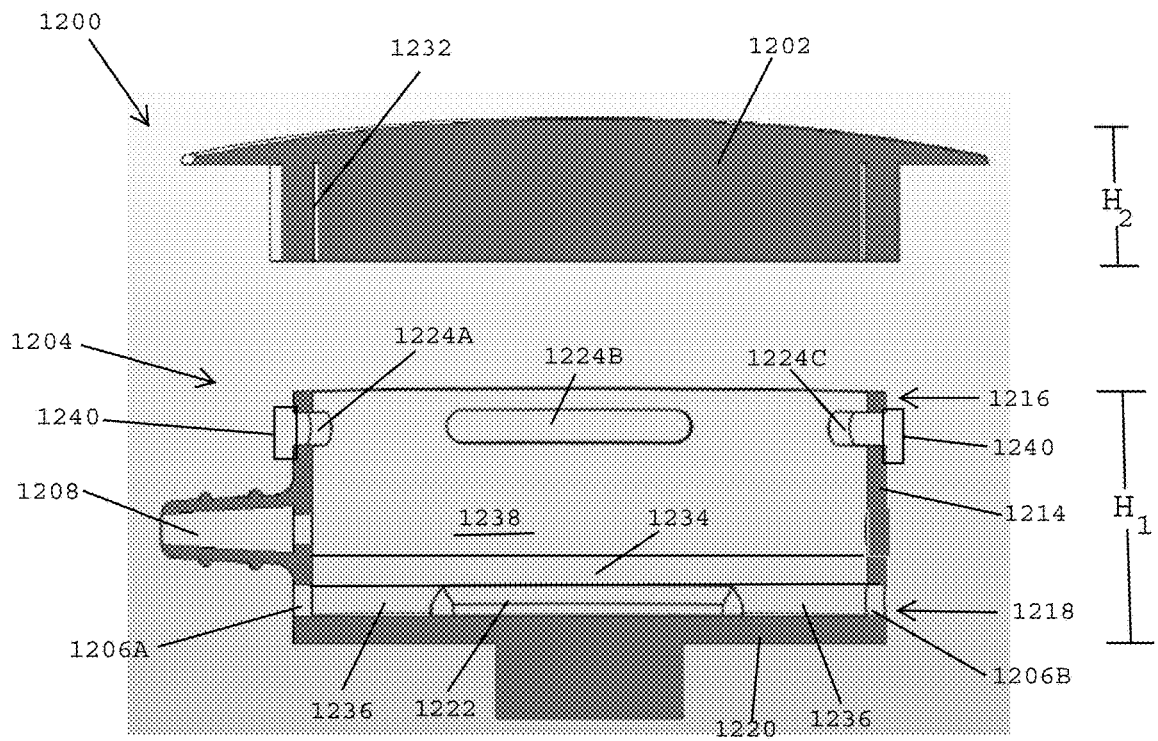
FIG. 26 illustrates a method of assembling the injection dome of FIGS. 25A-25C with the needle guard of FIGS. 24A-24D, in accordance with one embodiment of the present patent application.

Referring to FIG. 26, in one embodiment, the injection dome 1202 may be assembled with the needle guard 1204 by juxtaposing the bottom surface 1230 of the base 1228 of the injection dome 1202 with the upper end 1216 of the needle guard rim 1214 of the needle guard 1204. In one embodiment, the needle guard 1204 has a first height $H_1$ and the injection dome 1202 has a second height $H_2$ that is less than the first height $H_1$ of the needle guard.

In one embodiment, silicone material such as uncured silicone material or one or more uncured silicone sheets, or an adhesive material such as RTV may be used for securing the injection dome to the needle guard. In one embodiment, uncured silicone sheeting may be positioned at the upper end of the needle guard and, after the upper end of the needle guard and the uncured silicone sheets are inserted into the annular groove 1232 of the injection dome 1202, the uncured silicone sheets may be cured using heat for adhering the injection dome to the needle guard.

In one embodiment, the injection port assembly 1200 desirably includes the barrier membrane 1234 that divides the inside of the needle guard into an inflation chamber 1236 that is in communication with the inflation ports 1206A, 1206B formed in the needle guard rim 1214 of the needle guard 1204, and a drainage chamber 1238 that is in fluid communication with the drainage port 1208 formed in the needle guard rim 1214 of the needle guard 1204. In one embodiment, the barrier membrane 1234 preferably extends across the entire width and/or diameter of the needle guard rim 1214 of the needle guard 1204 for isolating the inflation chamber 1236 from the drainage chamber 1238. The barrier membrane support 1222 desirably projects upwardly from the needle guard base 1220 of the needle guard 1204 for supporting an underside of the barrier membrane 1234.

Figure 27:
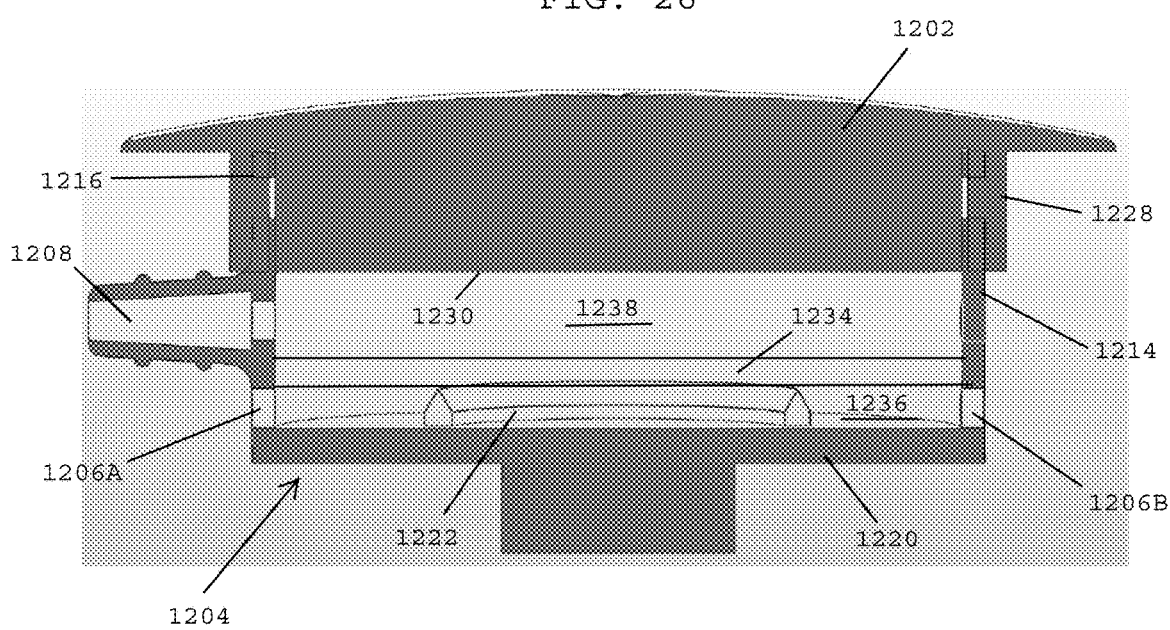
FIG. 27 is a cross-sectional view of the injection dome and the needle guard of FIG. 26 assembled together.

Referring to FIGS. 26 and 27, in one embodiment, in order to assemble the injection dome with the needle guard, the annular groove 1232 formed in the bottom surface 1230 of the base 1228 of the injection dome 1202 is desirably juxtaposed and aligned with the cylindrical shaped needle guard rim 1214 of the needle guard 1204. In one embodiment, the shapes and dimensions of the annular groove 1232 of the injection dome and the cylindrical shaped needle guard rim 1214 of the needle guard match one another.

In one embodiment, in order to secure the injection dome to the needle guard (e.g., form a hermetic seal), a joining component such as silicone sheeting 1240 may be positioned around the needle guard rim 1214 of the needle guard 1204. In one embodiment, the silicone sheeting 1240 is aligned with and covers the elongated slots 1224A-1224D (FIGS. 24A and 24B) located at the upper end 1216 of the needle guard rim 1214 of the needle guard 1204. In one embodiment, the injection dome 1202 is pressed onto the upper end 1216 of the needle guard rim 1214 of the needle guard 1204 so that that upper end 1216 of the outer wall of the needle guard and the silicone sheeting 1240 (FIG. 26) are disposed within the annular groove 1232 formed in the underside of the injection dome 1202. The silicone sheeting 1240 preferably forms a secure, water-tight attachment (e.g., a heat seal, a seal made using a silicone adhesive) between the injection dome 1202 and the needle guard rim 1214 of the needle guard 1204.

Referring to FIG. 27, in one embodiment, after the injection dome 1202 has been secured over the upper end 1216 of the needle guard rim 1214 of the needle guard 1204, the drainage chamber 1238 of the injection port assembly 1200, which is in fluid communication with the drainage port 1208, is preferably located between a top surface of the barrier membrane 1234 and the bottom surface 1230 of the base 1228 of the injection dome 1202. The inflation chamber 1236, which is in fluid communication with the inflation ports 1206A, 1206B extending through the needle guard rim 1214 of the needle guard 1204, is preferably located between a bottom surface of the barrier membrane 1234 and a top surface of the needle guard base 1220 of the needle guard 1204. The barrier membrane support 1222, projecting from the top surface of the needle guard base 1220 of the needle guard 1204, preferably supports the underside of the barrier membrane 1234.

Figure 28:
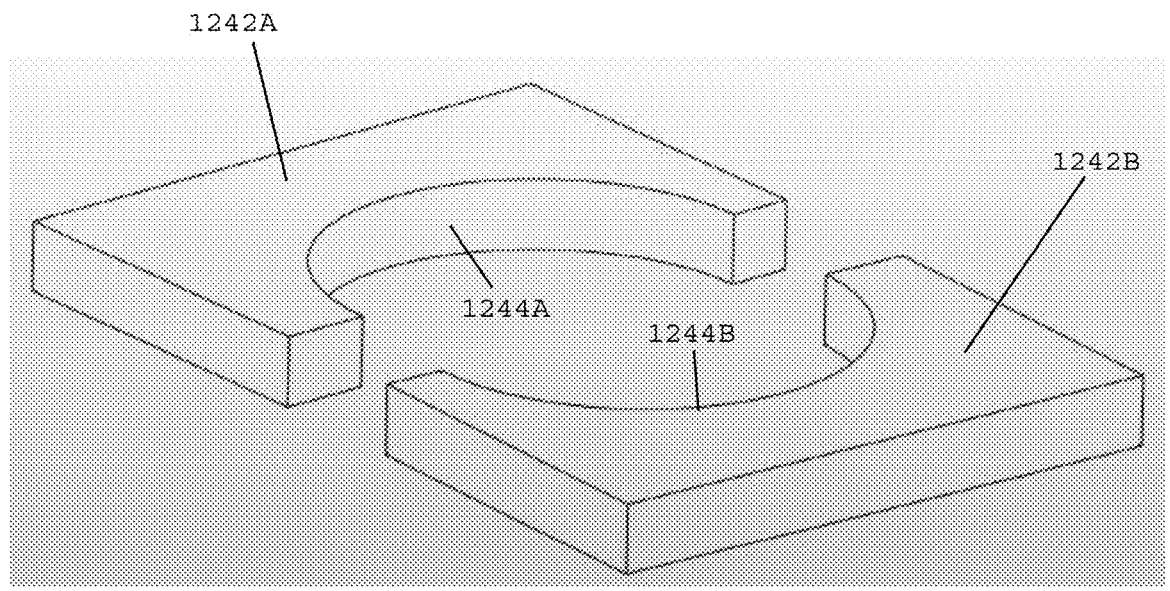
FIG. 28 is a perspective view of first and second anvils used for securing an injection dome to a needle guard, in accordance with one embodiment of the present patent application.

Referring to FIG. 28, in one embodiment, first and second anvils 1242A, 1242B may be utilized for securing the injection dome 1202 to the needle guard 1204 (FIG. 27). In one embodiment, the first anvil 1242A includes a first concave surface 1244A that substantially matches the shape of the outer perimeter of the base 1228 of the injection dome 1202 (FIG. 25B) and the shape of the outer surface of the cylindrical-shaped outer wall of the needle guard. The second anvil 1242B desirably includes a second concave surface 1244B that also matches the shape of the outer surface of the base 1228 of the injection dome 1202 (FIG. 25B) and the outer surface of the cylindrical-shaped outer wall of the needle guard. The first and second anvils preferably oppose one another on opposite sides of the base of the injection dome.

Figure 29:
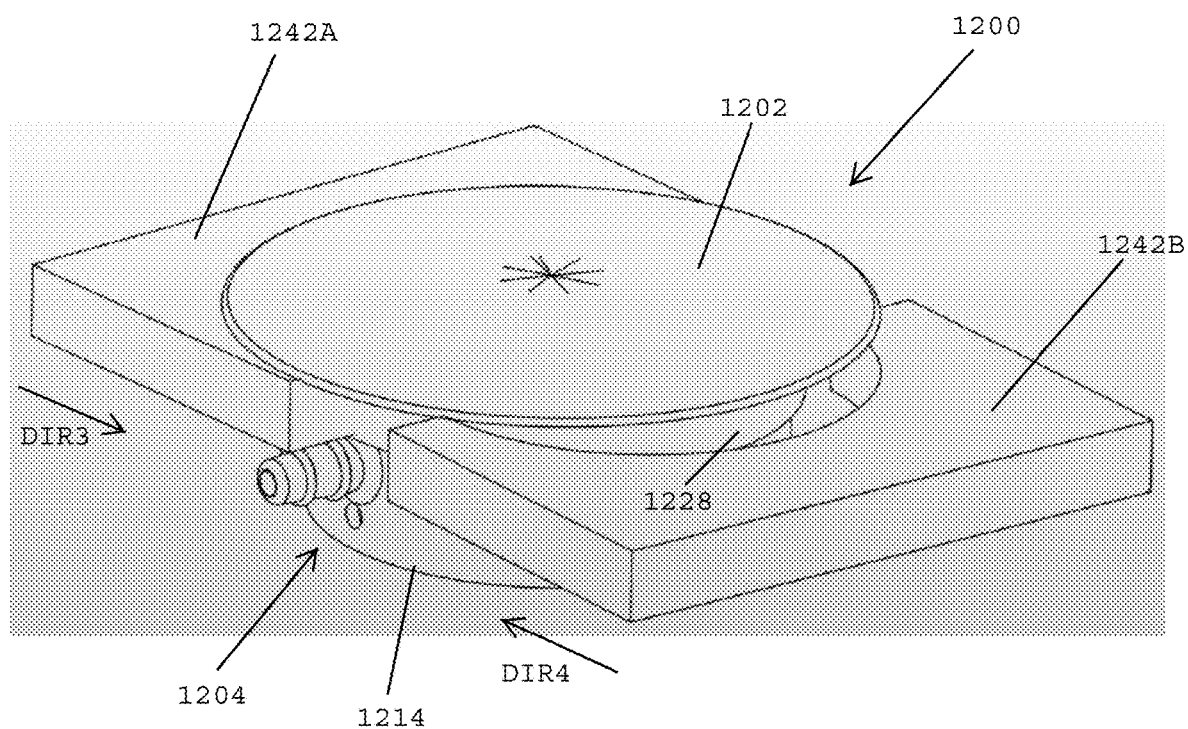
FIG. 29 is a perspective view of the first and second anvils of FIG. 28 during a stage of a method of securing an injection dome to a needle guard, in accordance with one embodiment of the present patent application.

Referring to FIG. 29, in one embodiment, after the base 1228 of the injection dome 1202 has been pressed onto the upper end 1216 of the needle guard rim 1214 of the needle guard 1204 for contacting the silicone sheeting, the first and second concave surfaces 1244A, 1244B (FIG. 28) of the first and second anvils 1242A, 1242B may be pressed against the outer surface of the base 1228 for pressing the silicone sheeting 1240 (FIG. 26) into the elongated slots 1224A-1224D located at the upper end 1216 of the needle guard rim 1214 of the needle guard 1204. In one embodiment, the first and second anvils 1242A, 1242B are pressed inwardly toward one another in the opposite directions DIR3, DIR4 for compressing the silicone sheeting 1240 onto the outer surface of the base 1228 of the injection dome 1202 for bonding the injection dome to the needle guard and preferably forming a seal therebetween. In one embodiment, the bonding of the injection dome to the needle guard may include using one or more uncured silicone sheets or a silicone adhesive for securing the injection dome to the needle guard. In one embodiment, heat may be used for curing the one or more silicone sheets of the silicone adhesive. In one embodiment, the silicone material is located in the elongated slots formed at the upper end of the needle guard to provide anchor points for adhering the injection port to the needle guard. In one embodiment, after the first and second anvils 1242A, 1242B having been used for securing the injection dome 1202 to the upper end of the needle guard 1204, the first and second anvils may be removed, whereupon the injection port assembly 1200 has the configuration shown in FIGS. 23B, 27, and 29 of the present patent application.

Figure 30:
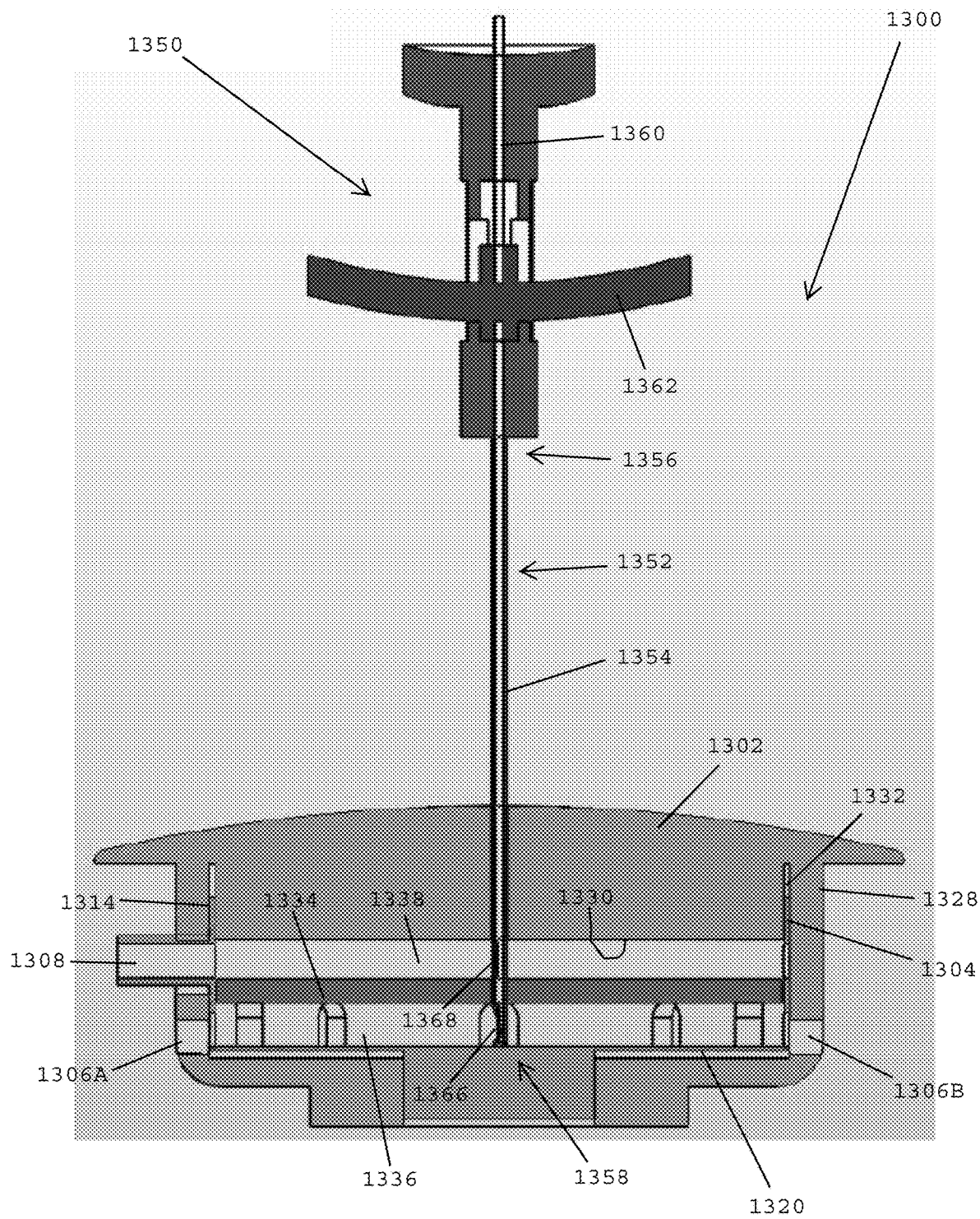
FIG. 30 is a cross-sectional view of an injection port assembly including a needle guard, a barrier membrane, an injection dome, and a needle assembly including a needle and an insert disposed inside the needle, in accordance with one embodiment of the present patent application.

In one embodiment, an injection port assembly has a configuration whereby a single needle having a moveable insert may be used for both inflating an implant shell and draining fluid that has collected around the outside of an implant shell. Referring to FIG. 30, in one embodiment, an injection port assembly 1300 preferably includes an injection dome 1302 and a needle guard 1304 having a needle guard rim 1314 that is pressed into an annular groove 1332 provided at an underside of the base of the injection dome 1302. The needle guard rim 1314 of the needle guard 1304 desirably includes first and second inflation ports 1306A, 1306B and a drainage port 1308 that is located above the inflation ports. The injection port assembly 1300 desirably includes a barrier membrane 1334 that divides an interior region of the needle guard 1304 into an inflation chamber 1336, which is located between an underside of the barrier membrane 1334 and a top surface of a needle guard base 1320 of the needle guard 1304, and a drainage chamber 1338, which is located between a top surface of the barrier membrane 1334 and the bottom surface 1330 of the base 1328 of the injection dome 1302. The inflation chamber 1336 is preferably in fluid communication with the inflation ports 1306A, 1306B formed in the needle guard rim 1314 of the needle guard 1304, and the drainage chamber 1338 is preferably in fluid communication with the drainage port 1308 formed in the outer wall of the needle guard.

In one embodiment, a needle assembly 1350 preferably includes a needle 1352 having an elongated shaft 1354 with a proximal end 1356 and a distal end 1358. In one embodiment, the needle assembly 1350 preferably includes an insert 1360 that is disposed inside the elongated shaft 1354 of the needle 1352. The insert 1360 is preferably coupled with an actuator 1362 that may be engaged for moving the insert along the longitudinal axis of the elongated shaft 1354 of the needle 1352, between an extended position for aligning the distal end of the insert 1360 with an inflation lumen 1366 of the needle 1352 and a retracted position for aligning the distal end of the insert 1360 with a drainage lumen 1368 of the needle 1352.

Figure 31A:
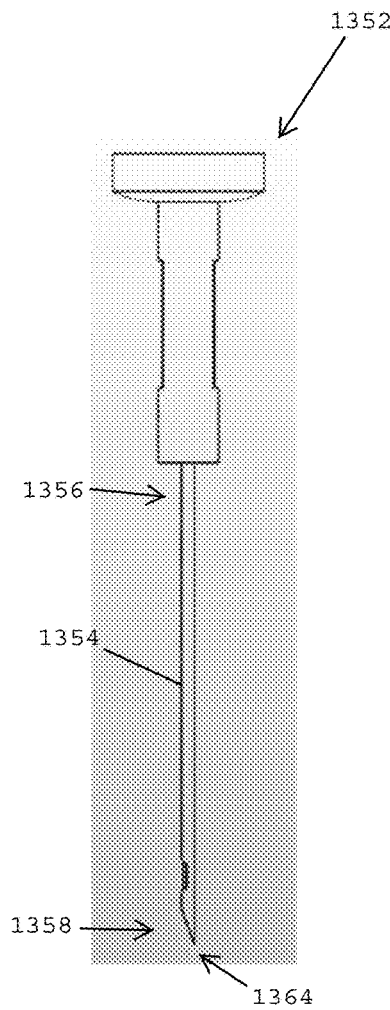
FIG. 31A is a side view of the needle shown in FIG. 30.
Figure 31B:
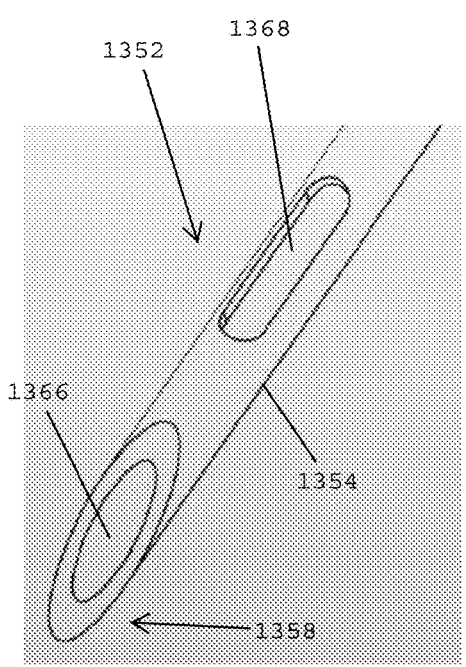
FIG. 31B is a distal end view of an elongated shaft of the needle shown, in FIG. 31A.
Figure 31C:
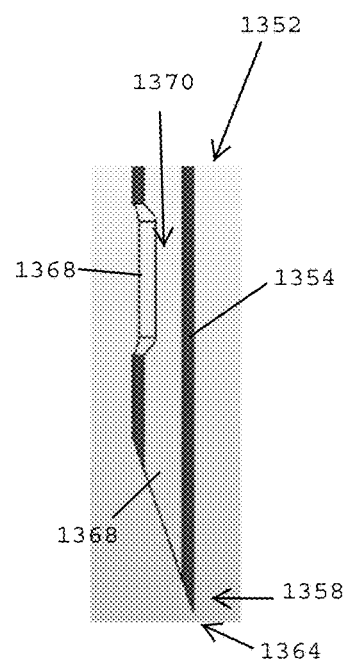
FIG. 31C is a cross-sectional view of the distal end of the elongated shaft of the needle shown in FIGS. 31A and 31B.

Referring to FIGS. 31A-31C, in one embodiment, the needle 1352 of the needle assembly 1350 (FIG. 30) preferably includes the elongated shaft 1354 of the needle having the proximal end 1356 and the distal end 1358 including a sharpened tip 1364 that facilitates passing the distal end 1358 of the elongated shaft 1354 of the needle through an object such as the injection dome disclosed herein. In one embodiment, the needle 1352 preferably includes the inflation lumen 1366, which is located at the distal end 1358 of the elongated shaft 1354, and a drainage lumen 1368, which extends through the outer wall of the elongated shaft and is proximal to the inflation lumen 1366. As will be described in more detail herein, in one embodiment, when the distal end 1358 of the elongated shaft 1354 of the needle 1352 is inserted into an injection dome of an injection dome assembly, the inflation lumen 1366 is in fluid communication with the inflation chamber 1336 of the injection port assembly 1300 (FIG. 30), and the drainage lumen 1368 is in fluid communication with the drainage chamber 1338 of the injection port assembly 1300 (FIG. 30).

Referring to FIG. 31C, in one embodiment, the needle 1352 preferably includes an elongated conduit 1370 that extends along the length of the elongated shaft 1354 of the needle. The elongated conduit 1370 is preferably in fluid communication with both the inflation lumen 1366 and the drainage lumen 1368.

Figure 32A:
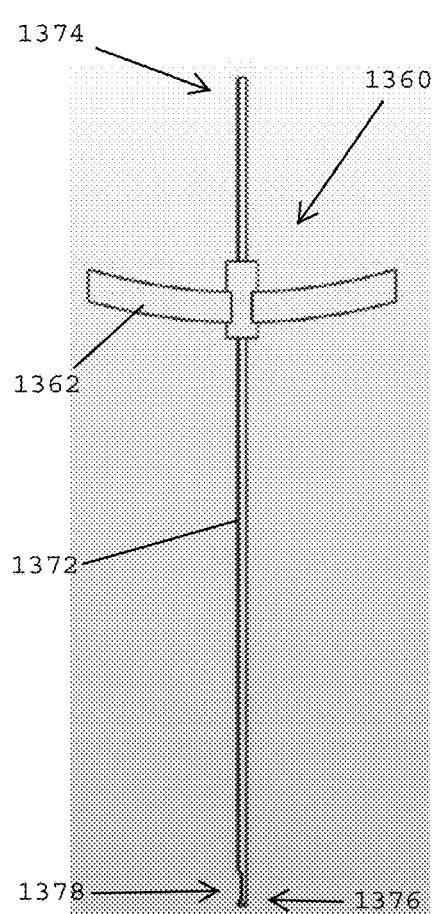
FIG. 32A is a side elevation view of the insert shown in FIG. 30.
Figure 32B:
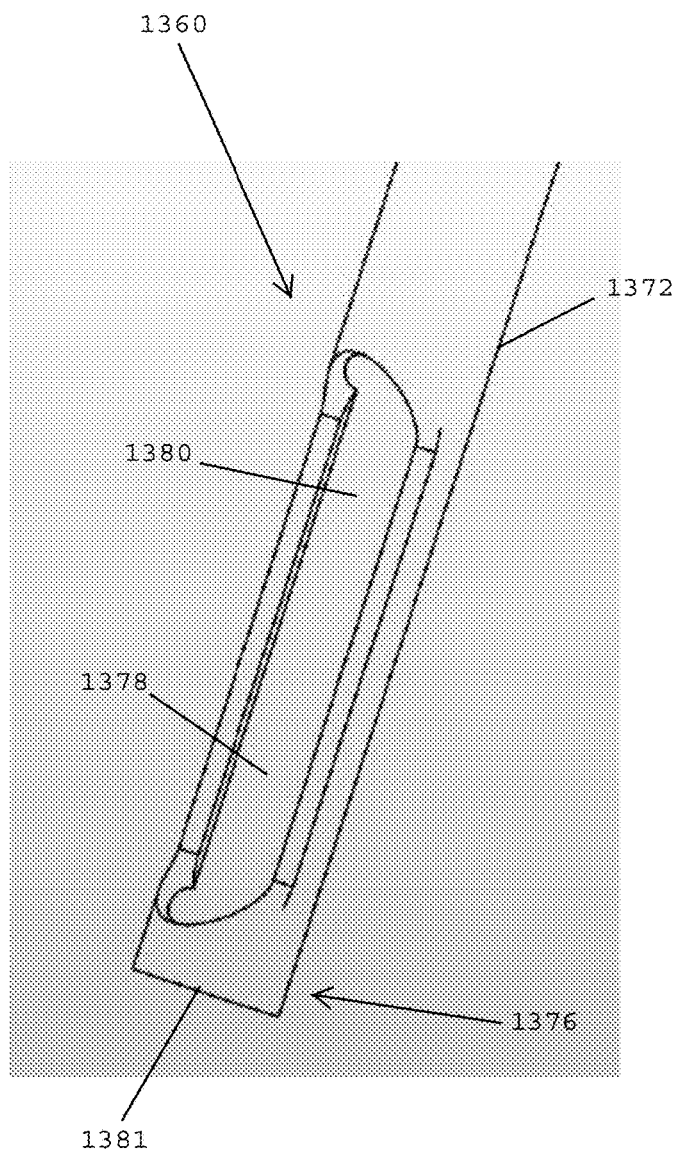
FIG. 32B is a distal end view of the insert shown in FIG. 32A.

Referring to FIGS. 32A and 32B, in one embodiment, the needle assembly 1350 (FIG. 30) preferably includes the insert 1360 that is disposed inside the elongated shaft of the needle 1354 (FIG. 31A). In one embodiment, the insert 1360 preferably includes an elongated shaft 1372 having an elongated conduit 1380 that extends along the length of the insert from a proximal end 1374 to a distal end 1376 of the insert. The distal end 1376 of the elongated shaft 1372 of the insert desirably has a side port 1378 that is in fluid communication with the elongated conduit 1380 of the insert 1360. The distal end 1376 of the elongated shaft 1372 of the insert 1360 is closed by a distal end wall 1381. The actuator 1362 (FIG. 32A) is secured to the outer surface of the elongated shaft 1372 of the insert 1360 for allowing medical personnel to move the insert relative to the needle 1352 (FIG. 31A) between an extended position in which the side port 1378 of the insert is in fluid communication with the inflation lumen 1366 (FIG. 31B) of the needle and a retracted position in which the side port 1378 of the insert is in fluid communication with the drainage lumen 1368 (FIG. 31B) of the needle.

Referring to FIG. 32B, in one embodiment, the side port 1378 is formed in the outer wall of the elongated shaft 1372 of the insert 1360. The side port 1378 is preferably located adjacent the distal end 1376 of the elongated shaft 1372. In one embodiment, the side port 1378 is preferably in fluid communication with an elongated conduit 1380 that extends along the length of the elongated shaft 1372. In one embodiment, the elongated conduit 1380 preferably extends between the proximal end 1374 and the distal end 1378 of the elongated shaft 1372 of the insert 1360 (FIG. 32A).

Referring to FIG. 33, in one embodiment, the insert 1360 is preferably disposed within the elongated shaft 1354 of the needle 1352 to form the needle assembly 1350 shown in FIG. 30. The insert 1360 preferably includes the side port 1378 that is in fluid communication with the elongated conduit 1380 that extends along the length of the insert 1360. The elongated shaft 1354 of the needle 1352 preferably includes the inflation lumen 1366 that is located adjacent the distal end 1358 of the elongated shaft 1354, and the drainage lumen 1368 that is proximal to the inflation lumen 1366.

Referring to FIGS. 33 and 34, in one embodiment, the insert 1360 is movable between the extended position shown in FIG. 33 and the retracted position shown in FIG. 34. In the extended position shown in FIG. 33, the side port 1378 of the insert 1360 is aligned with the inflation lumen 1366 located at the distal end 1358 of the elongated shaft 1354 of the needle 1352. In the extended position shown in FIG. 33, the outer wall of the elongated shaft 1372 of the insert 1360 covers the drainage lumen 1368 of the needle 1352 so that no fluid may pass through the drainage lumen 1368 of the needle 1352.

In one embodiment, the insert 1360 may be moved to the retracted position shown in FIG. 34 so that the side port 1378 of the insert is aligned with the drainage lumen 1368 of the elongated shaft 1354 of the needle 1352. In the retracted position, the closed distal end wall 1381 of the insert blocks the inflation lumen 1366 of the needle 1352 so that no fluid may pass into or out of the needle 1352 through the inflation lumen 1366 of the needle.

In one embodiment, the actuator 1362 of the needle assembly 1350 (FIG. 30) may be used for repeatedly moving the insert 1360 back and forth between the extended position shown in FIG. 33 and the retracted position shown in FIG. 34. In the extended position of FIG. 33, the side port 1378 of the insert 1360 is aligned with the inflation lumen 1366 of the needle 1352 so that fluid may pass out of the inflation lumen (e.g., for being introduced into the inflation chamber 1336 (FIG. 30) of the injection port assembly). When the insert 1360 is shifted and/or moved into the retracted position shown in FIG. 34, the side port 1378 of the insert 1360 is preferably aligned with the drainage lumen 1368 of the needle 1352 so that the elongated conduit of the insert is in fluid communication with the drainage chamber 1338 (FIG. 30) of the injection port assembly 1300 (FIG. 30).

Figure 35A:
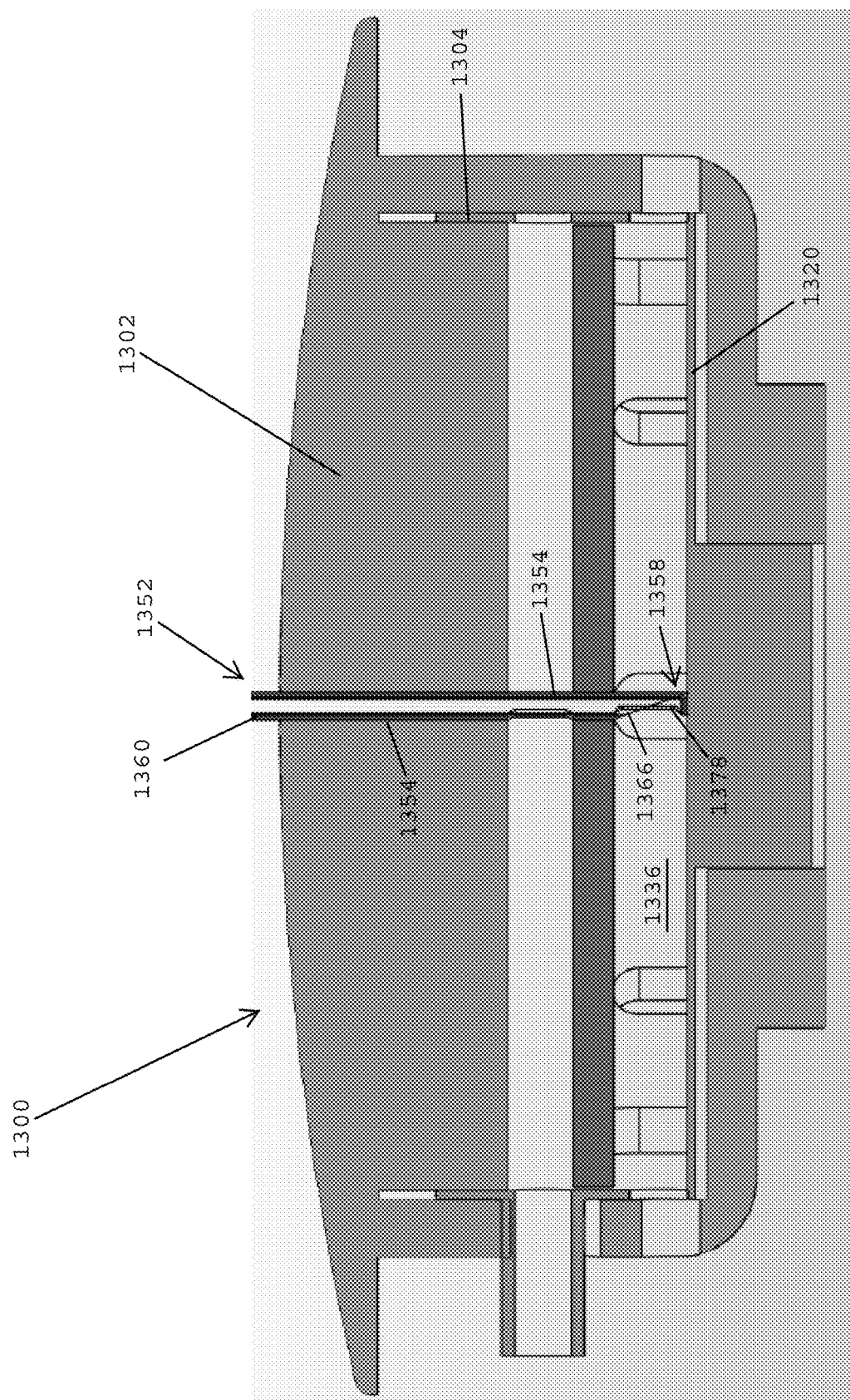
FIG. 35A is a cross-sectional view of the injection port assembly of FIG. 30 with the distal end of the needle assembly inserted into an inflation chamber of the injection port assembly, in accordance with one embodiment of the present patent application.
Figure 35B:
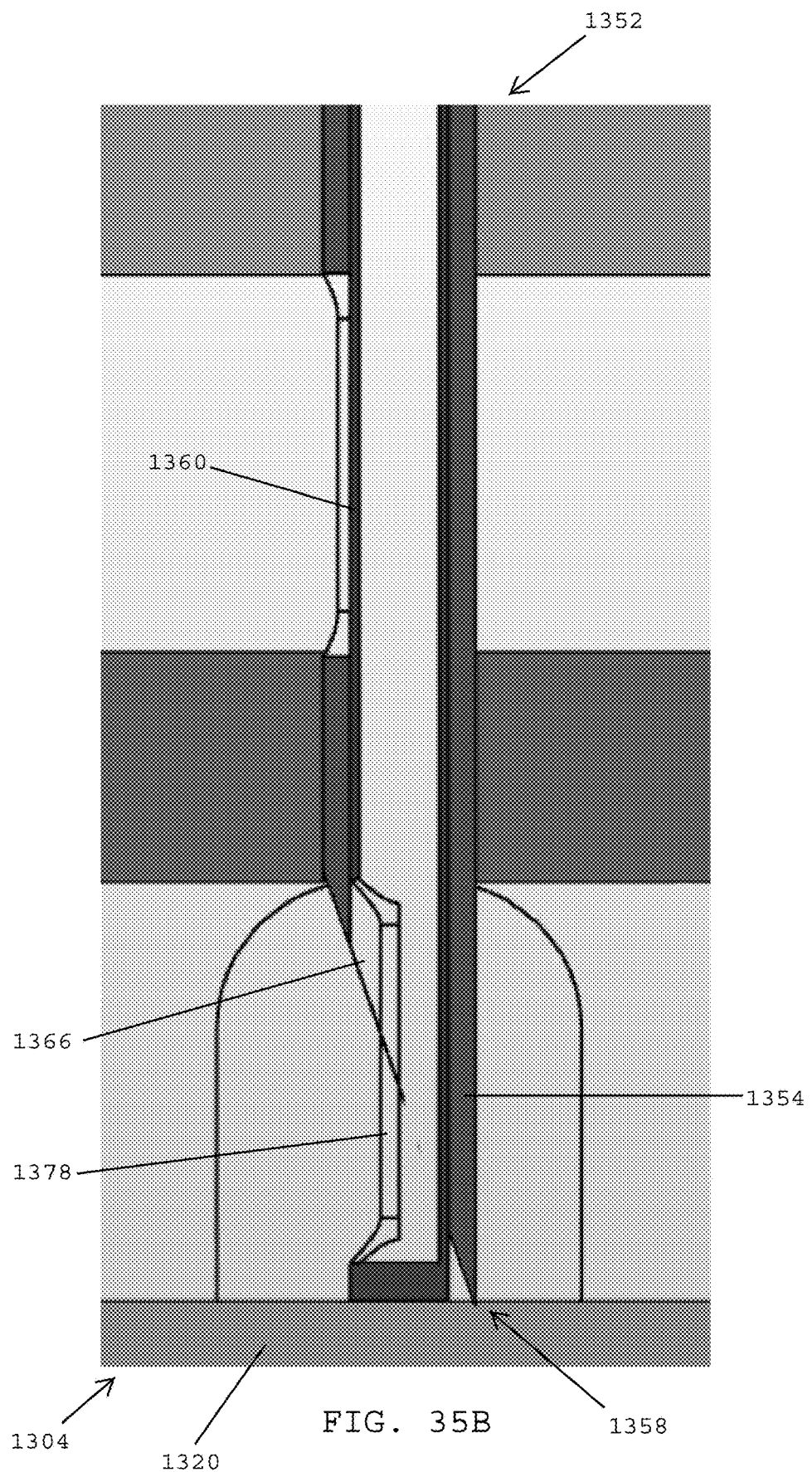
FIG. 35B is a magnified view of the distal end of the needle assembly shown in FIG. 35A inserted into the injection chamber of the injection port assembly.

Referring to FIGS. 35A and 35B, in one embodiment, the distal end 1358 of the elongated shaft 1354 of the needle 1352 may be inserted into the injection dome 1302 of the injection port assembly 1300 until the distal end 1358 of the needle 1352 abuts against the needle guard base 1320 of the needle guard 1304. In one embodiment, the insert 1360 may be shifted into the extended position so that the side port 1378 of the insert 1360 is aligned with the inflation lumen 1366 of the needle 1352. With the insert 1360 in the extended position shown in FIGS. 35A and 35B, the distal end 1358 of the needle 1352 is in fluid communication with the inflation chamber 1336 of the injection port assembly 1300, whereupon the needle may be used for directing fluid into the inflation chamber 1336 for inflating a shell and/or providing an infusing fluid around the outside of the shell.

Figure 36:
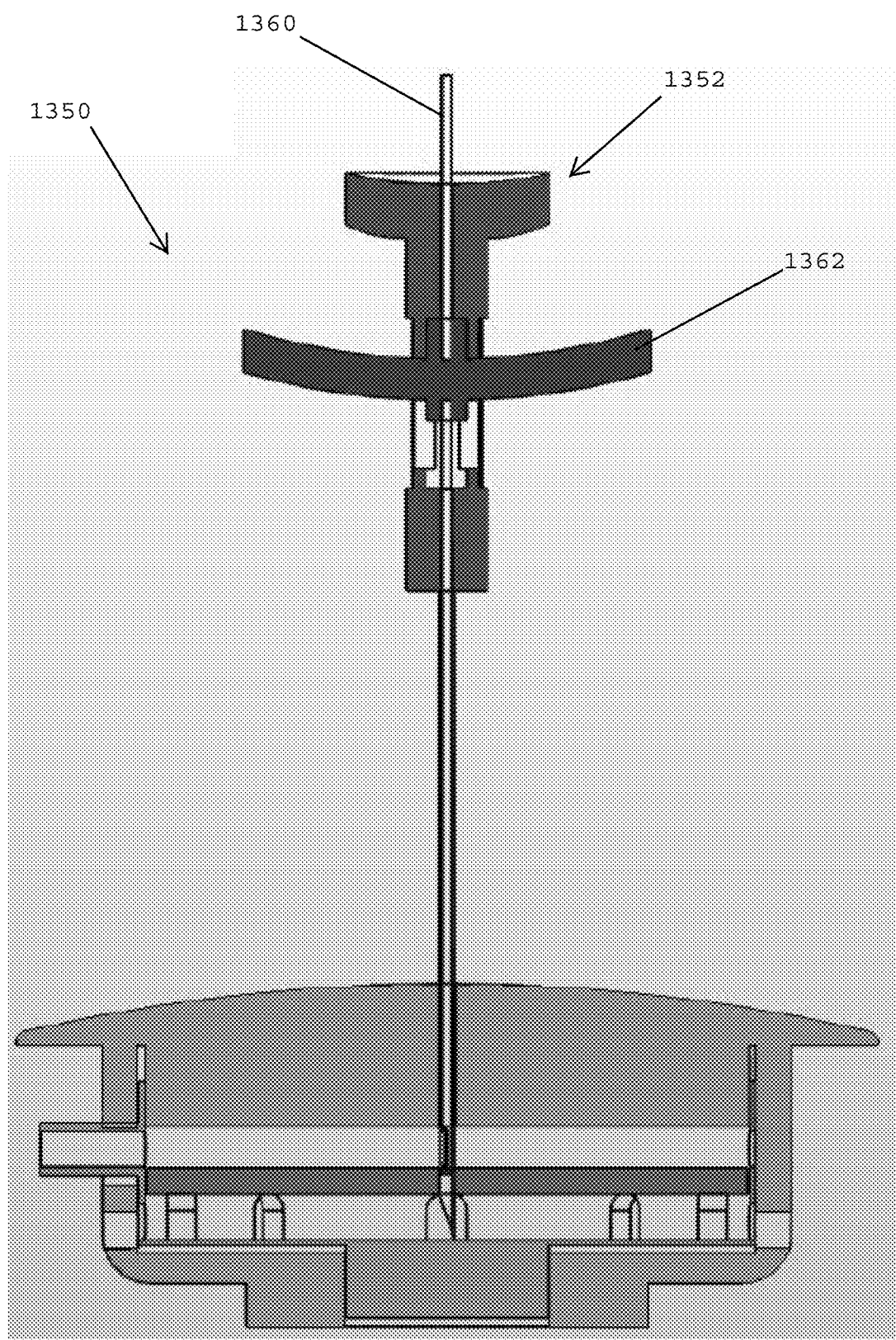
FIG. 36 is a cross-sectional view of the injection port assembly and the needle assembly of FIG. 30 with the insert in a retracted position, in accordance with one embodiment of the present patent application.

Referring to FIG. 36, in one embodiment, the actuator 1362 of the needle assembly 1350 is connected with the elongated shaft of the insert 1360 for moving the insert from the extended position shown in FIG. 33 to the retracted position shown in FIG. 34.

Figure 37A:
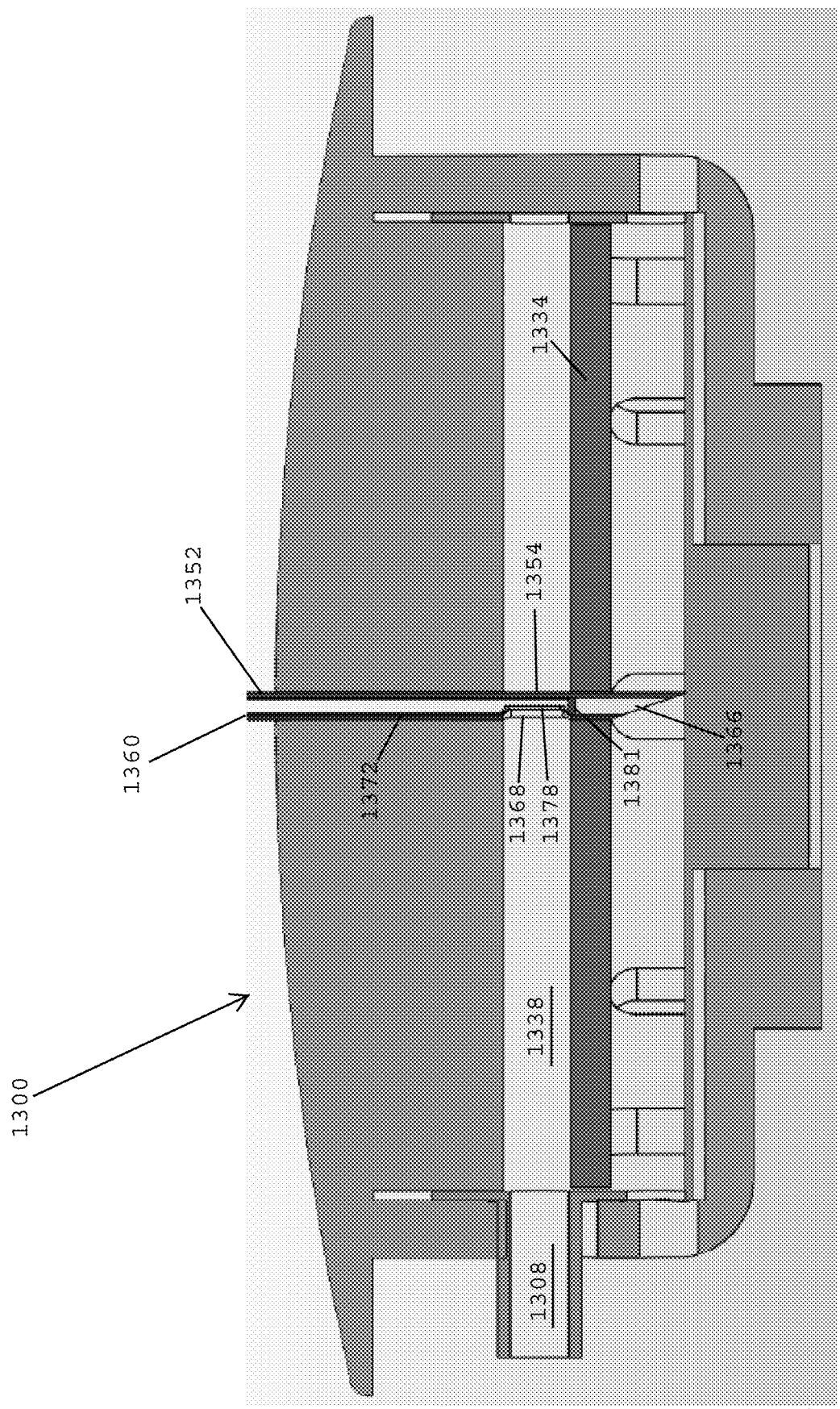
FIG. 37A is a magnified view of the injection port assembly and the needle assembly of FIG. 36 with the insert in the retracted position, in accordance with one embodiment of the present patent application.
Figure 37B:
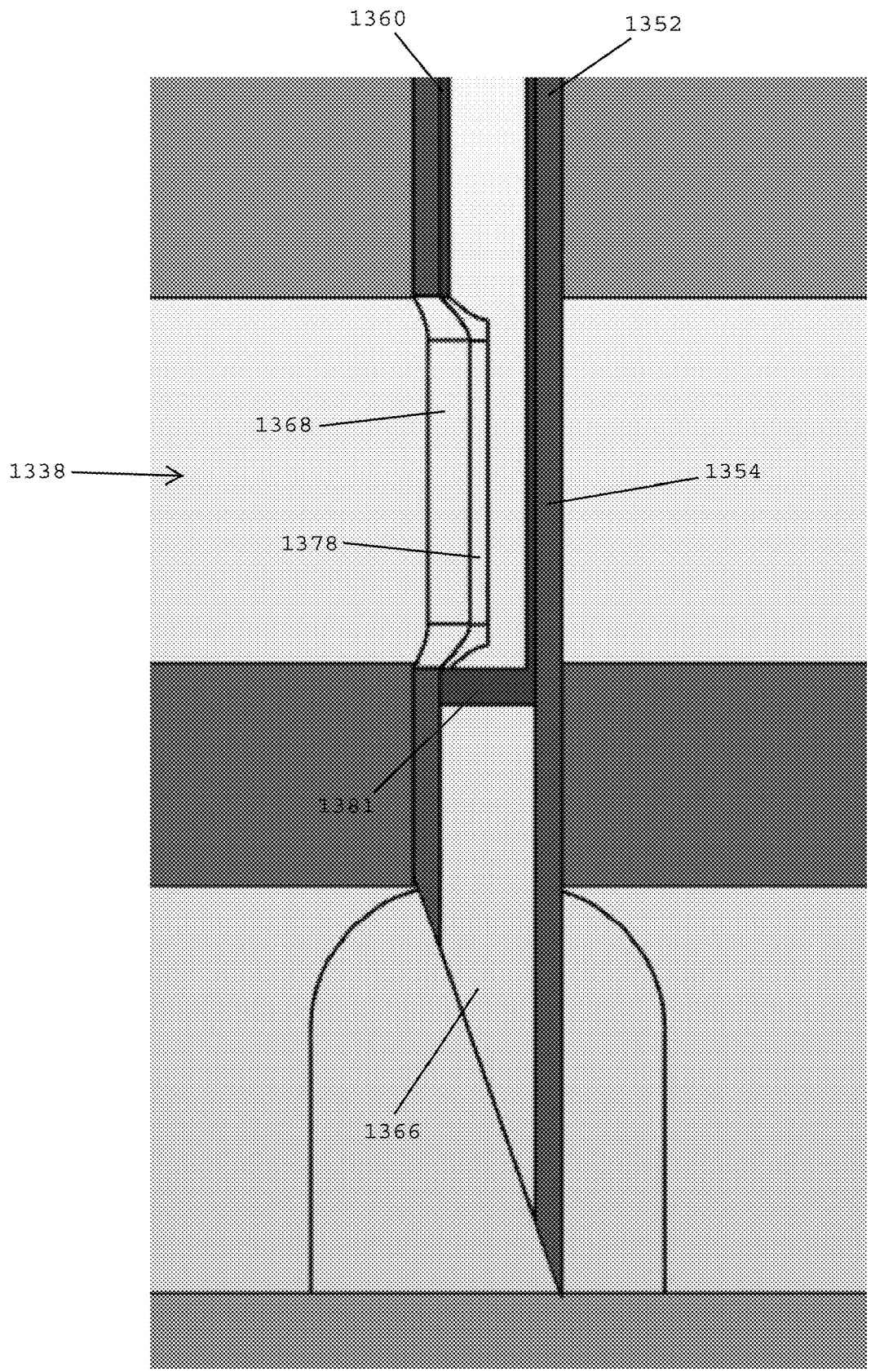
FIG. 37B is a magnified view of the distal end of the needle assembly of FIG. 37A with the insert in the retracted position for being aligned with a drainage chamber of the injection port assembly, in accordance with one embodiment of the present patent application.

Referring to FIGS. 37A and 37B, in one embodiment, with the insert 1360 in the retracted position, the side port 1378 of the insert 1360 is aligned with the drainage lumen 1368 of the elongated shaft 1354 of the needle 1352. The distal end wall 1381 located at the distal end of the elongated shaft 1372 of the insert 1360 closes the inflation lumen 1366 at the distal end 1358 of the needle 1352. In the retracted position, the side port 1378 of the insert 1360 is aligned with the drainage lumen 1368 of the needle 1352 so that the needle 1352 is in fluid communication with the drainage chamber 1338 of the injection port assembly 1300. As a result, fluid that is drawn into the drainage port 1308 may be sucked into the drainage lumen 1368 for being removed from a proximal end of the needle 1352.

Figure 38:
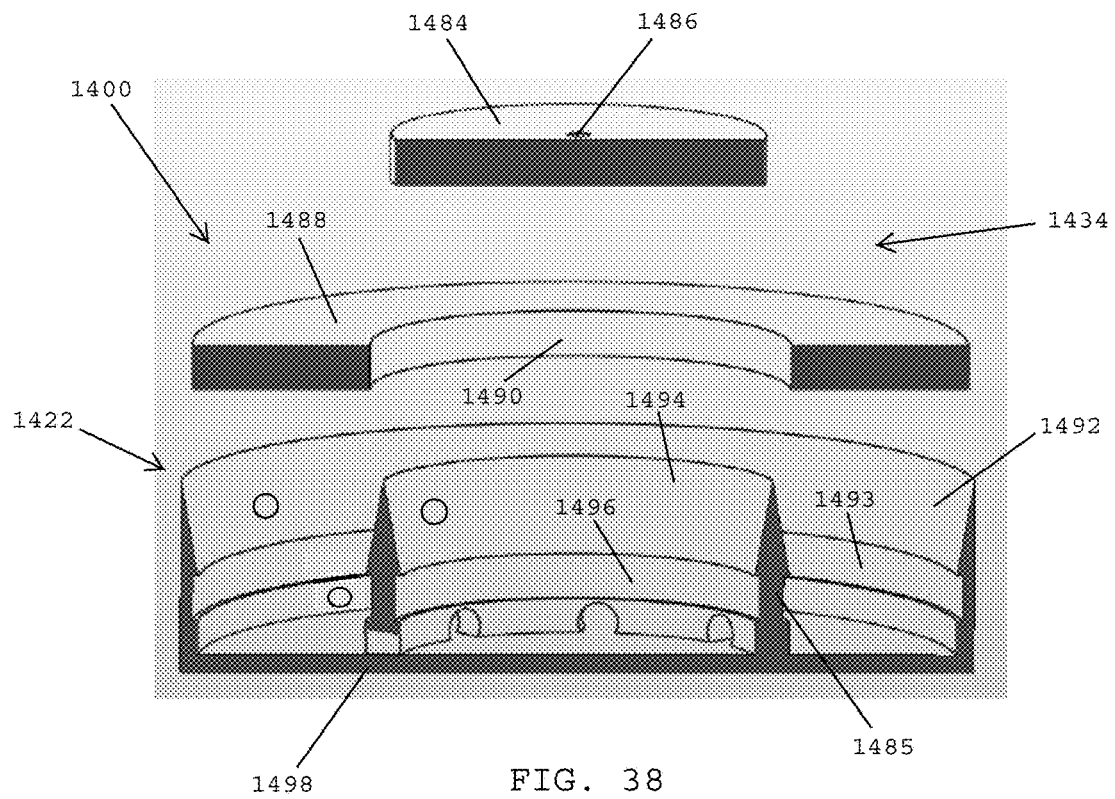
FIG. 38 is a cross-sectional view of a barrier membrane support for an injection dome assembly, the barrier membrane support being adapted to receive an inner barrier membrane and an outer barrier membrane, in accordance with one embodiment of the present patent application.

Referring to FIG. 38, in one embodiment, an injection port assembly 1400 may include a barrier membrane support 1422 that is adapted to support a barrier membrane 1434 that is located inside a needle guard. In one embodiment, the barrier membrane 1434 preferably includes an inner barrier membrane 1484 with a central opening 1486 and an outer barrier membrane 1488 having a donut-shaped opening 1490 in its center.

In one embodiment, the barrier membrane support 1422 preferably includes an annular outer wall 1492 having an inner surface with an inner annular groove 1493, an annular inner wall 1494 having an outer surface with an outer annular groove 1495 and an inner surface with an inner annular groove 1496. In one embodiment, the barrier membrane support 1422 preferably includes a central post 1497 (FIG. 39) that is surrounded by the inner annular wall 1494. The barrier membrane support 1422 preferably has a bottom wall 1498 that closes the bottom of the barrier membrane support 1422. The outer annular wall 1492, the inner annular wall 1494, and the central post 1497 (FIG. 39) preferably project away from the bottom wall 1498 of the barrier membrane support 1422.

Figure 39:
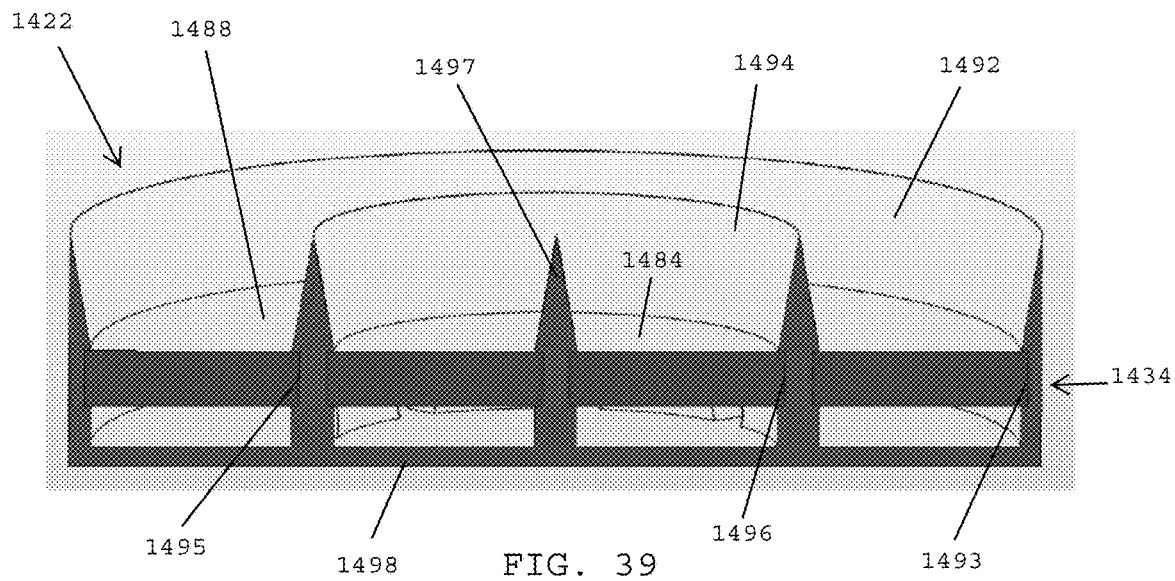
FIG. 39 is a cross-sectional view of the barrier membrane support, the inner barrier membrane, and the outer barrier membrane of FIG. 38.

Referring to FIG. 39, in one embodiment, the inner barrier membrane 1484 is preferably pressed onto the central post 1497 with the central post passing through the central opening 1486 (FIG. 38) of the inner barrier membrane 1484. The outer perimeter of the inner barrier membrane 1484 is preferably seated within the inner annular groove 1496 (FIG. 38) formed in the inner annular wall 1494 of the barrier membrane support 1422.

In one embodiment, the outer barrier membrane 1488 is preferably pressed into the space between the outer annular wall 1492 and the inner annular wall 1494. The outer perimeter of the outer barrier membrane 1488 is preferably seated within the inner annular groove 1493 of the outer annular wall 1492, and the inner perimeter of the outer barrier membrane 1488 is preferably seated within the outer annular groove 1495 formed in the inner annular wall 1494.

After the inner and outer barrier membranes 1484, 1488 have been assembled with the barrier membrane support 1422, the barrier membrane 1434 preferably divides the barrier membrane support 1422 into an inflation chamber 1436 that is disposed between an underside of the barrier membrane 1434 and the top surface of the bottom wall 1498 of the barrier membrane support 1422 and a drainage chamber 1438 that is located above the barrier membrane 1434.

Figure 40:
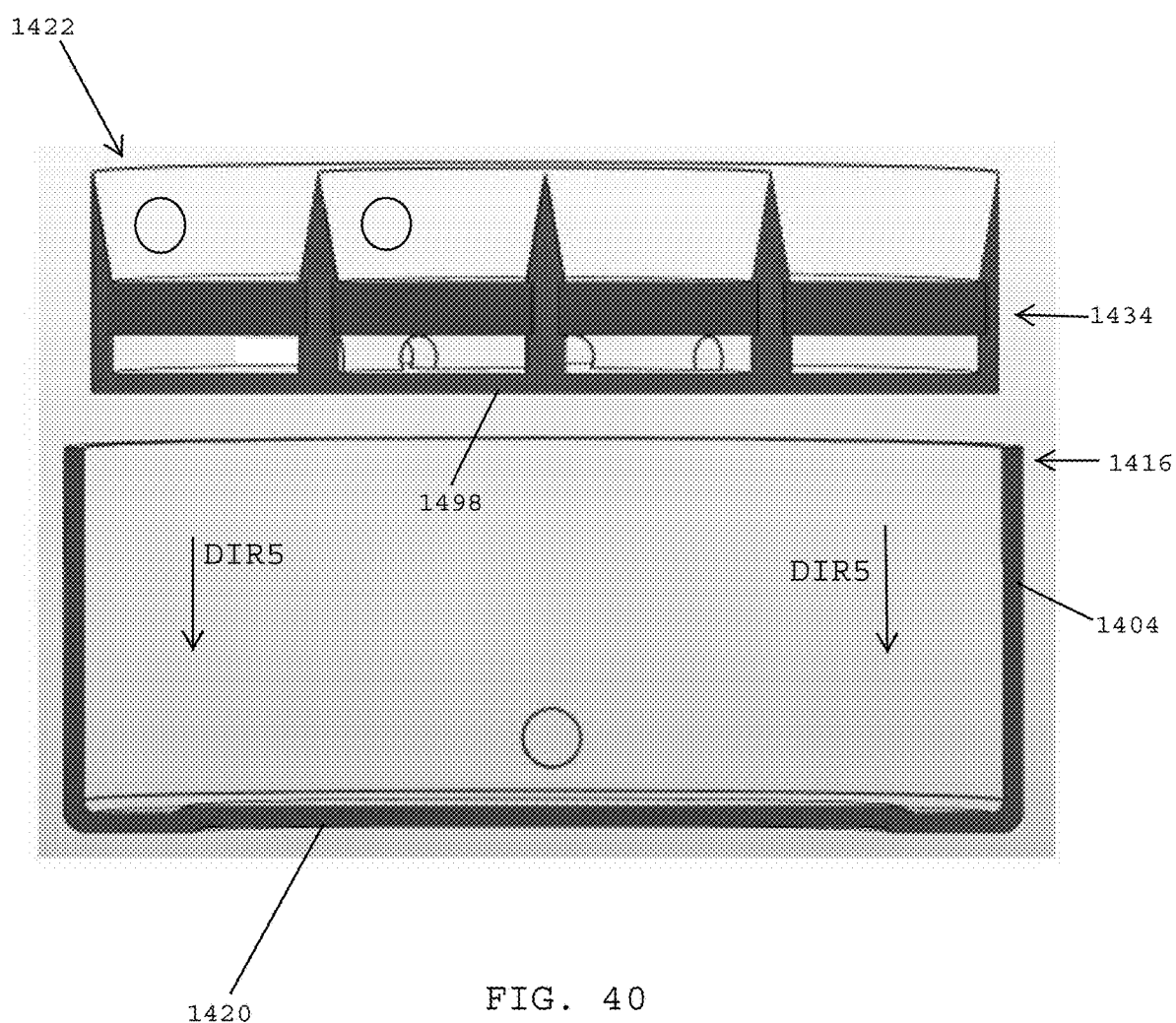
FIG. 40 shows a stage of a method of assembling the barrier membrane support of FIG. 38 with a needle guard, in accordance with one embodiment of the present patent application.

Referring to FIG. 40, in one embodiment, the barrier membrane support 1422 and the barrier membrane 1434 shown in FIG. 39 may be juxtaposed with an open upper end of a needle guard 1404 having a needle guard rim 1414. In one embodiment, the bottom wall 1498 of the barrier membrane support 1422 is preferably juxtaposed with the opening at the upper end 1416 of the needle guard rim 1414 of the needle guard 1404. The barrier membrane support 1422 is preferably passed through the opening at the upper end 1416 of the needle guard rim 1414 of the needle guard 1404 in the direction DIR5 until the bottom wall 1498 of the barrier membrane support 1402 abuts against a top surface of a needle guard base 1420 of the needle guard 1404.

Figure 41:
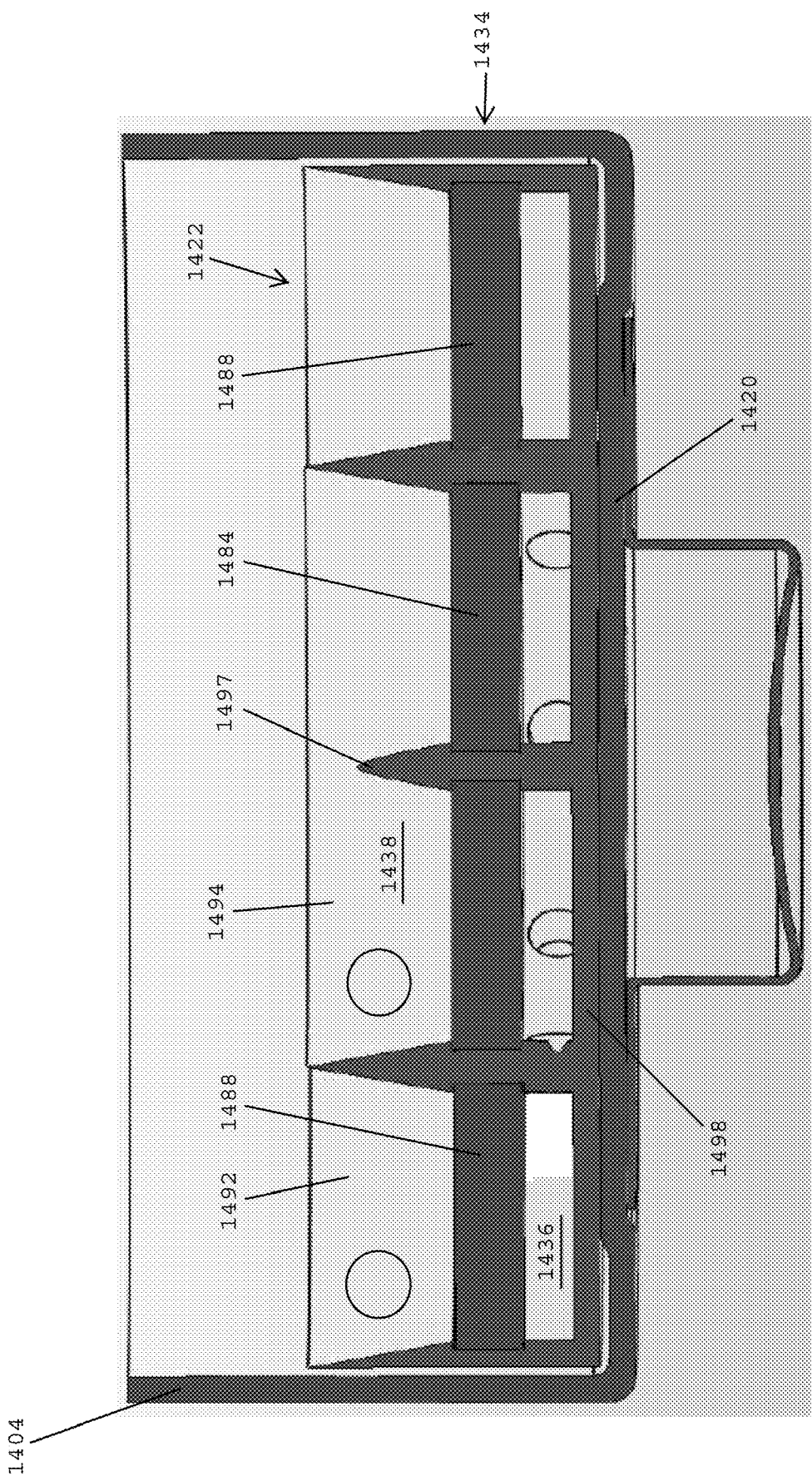
FIG. 41 is a cross-sectional view of the barrier membrane support and the needle guard of FIG. 40 after the barrier membrane support has been secured with the needle guard, in accordance with one embodiment of the present patent application.

Referring to FIG. 41, after the barrier membrane support 1422 is fully inserted into the needle guard 1404, the bottom wall 1498 of the barrier membrane support 1422 preferably abuts against the needle guard base 1420 of the needle guard 1404. The outer barrier membrane 1488 preferably extends between and is supported by annular grooves formed in the respective outer annular wall 1492 and inner annular wall 1494 of the barrier membrane support 1422. The inner barrier membrane 1484 is preferably supported by the inner annular wall 1494 and the central post 1497. The barrier membrane support 1422 preferably holds the inner and outer barrier membranes 1484, 1488 at a position that is spaced away from the bottom wall 1498 of the barrier membrane support. As a result, the barrier membrane 1434 defines the inflation chamber 1436 that is preferably located between an underside of the barrier membrane 1434 and a top surface of the bottom wall 1498 of the barrier membrane support 1422, and a drainage chamber 1438 that is located above the barrier membrane 1434.

Figure 42:
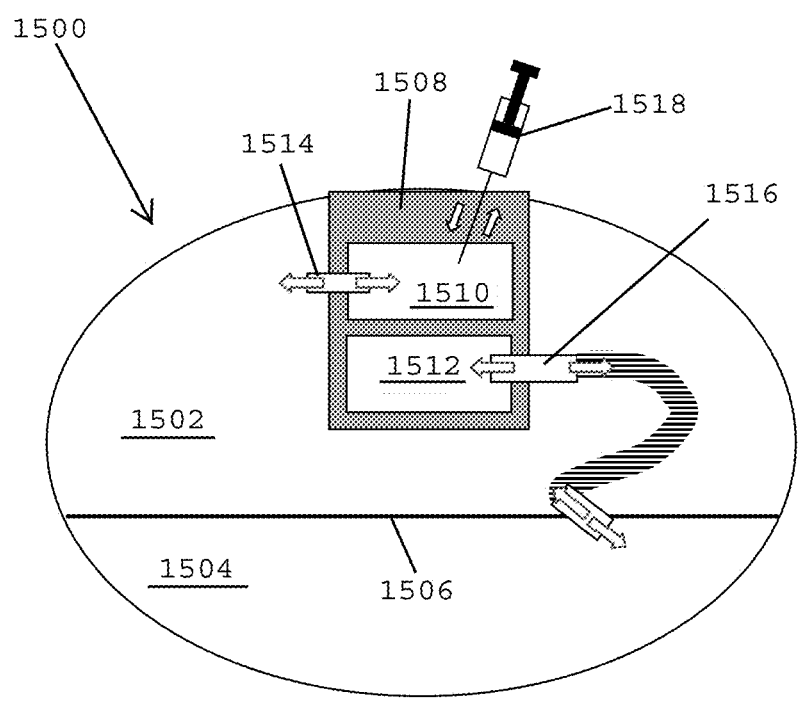
FIG. 42 is a schematic view of a tissue expander having two expansion zones that are isolated from one another and a multi-compartment injection dome assembly, in accordance with one embodiment of the present patent application.

Referring to FIG. 42, in one embodiment, an implant shell 1500 preferably has a first expandable chamber 1502 and a second expandable chamber 1504 that is isolated from the first expandable chamber 1502 by a membrane 1506 that extends across the interior of the shell 1500. In one embodiment, the implant shell 1500 desirably includes a multi-compartment injection dome 1508 having a first fluid compartment 1510 and a second fluid compartment 1512 that is isolated from the first fluid compartment 1510.

In one embodiment, the first fluid compartment 1510 of the injection dome 1508 is in communication with the first expandable chamber 1502 of the implant shell 1500 via a first valve 1514. The second fluid compartment 1512 of the injection dome 1508 is desirably in fluid communication with the second expandable chamber 1504 of the implant shell 1500 via a second valve 1516. In one embodiment, when an injection needle 1518 is used to introduce a first fluid into the first fluid compartment 1510 of the injection dome 1508, the first expandable chamber 1502 of the shell 1500 may be expanded by the first fluid. When the needle 1518 is used to deliver a second fluid into the second fluid compartment 1512 of the injection dome 1508, the second expandable chamber 1504 of the implant shell 1500 may be expanded with the second fluid. The first and second fluids may have the same properties (e.g., both saline solutions) or different properties (e.g., the first fluid is saline solution and the second fluid is an antibiotic solution).

In one embodiment, the injection needle 1518 may have a construction similar to the needle assembly 1350 with the moveable insert 1360 shown and described above in FIGS. 30-37B of the present patent application. Thus, a needle may be inserted into the injection dome 1508 and, without moving the position of the needle relative to the injection dome, the needle insert may be moved between a retracted position and an extended position for accessing both the first fluid compartment 1510 and the second fluid compartment 1512 of the injection dome 1508. In one embodiment, with the insert in a retracted position, the needle may be used for introducing fluid into the first fluid compartment 1510 of the injection dome 1508. In one embodiment, with the insert in an extended position, the needle may be used for introducing fluid into the second fluid compartment 1512 of the injection dome 1508.

In one embodiment, an implant shell may include two or more expandable chambers (e.g., three expandable chambers). In one embodiment, each of the two or more expandable chambers is associated with a different fluid compartment of an injection dome. For example, in an embodiment in which the implant shell has four expandable chambers, the injection dome may have four fluid chambers, whereby each fluid chamber of the injection dome is in fluid communication with a different one of the expandable chambers of the implant shell. In one embodiment, an injection dome may have more fluid chambers than the number of expandable chambers that are present in an implant shell. For example, an injection dome may have four fluid chambers in fluid communication with four respective expandable chambers of an implant shell and a fifth fluid chamber that is in fluid communication with a drainage conduit for draining fluids that collect around the outside of the implant shell.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A tissue expander having an integrated drain comprising:
a shell having an injection port opening and one or more drainage holes formed in said shell that are spaced from said injection port opening;
an injection port assembly disposed in said injection port opening, wherein said injection port assembly forms a fluid-tight seal with said shell;
said injection port assembly including a needle guard having a needle guard base with a top surface;
a barrier membrane disposed within said needle guard that overlies the top surface of said needle guard base, wherein said barrier membrane defines an inflation chamber located between the top surface of said needle guard base and a bottom surface of said barrier membrane, and wherein said barrier membrane defines a drainage chamber located within said needle guard that overlies a top surface of said barrier membrane;
one or more inflation ports in fluid communication with said inflation chamber for inflating and deflating said shell with a first fluid;
a drainage conduit in fluid communication with and extending between said drainage chamber and said one or more drainage holes formed in said shell for draining a second fluid from outside said shell;
said drainage conduit comprising a second end coupled with a drain, which, in turn, is in fluid communication with said one of more drainage holes formed in said shell;
a drainage manifold that is aligned with and covers said one or more drainage holes formed in said shell.

2. The tissue expander as claimed in claim 1, further comprising:
a first needle having an inflation lumen at a distal tip, wherein said first needle is adapted for insertion into said injection port assembly so that said inflation lumen of said first needle is aligned with said inflation chamber for selectively inflating and deflating said shell using the first fluid;
a second needle having a closed distal tip and a drainage lumen spaced proximally from said closed distal tip, wherein said second needle is adapted for insertion into said injection port assembly so that said drainage lumen of said second needle is aligned with said drainage chamber for draining the second fluid from outside said shell.

3. The tissue expander as claimed in claim 1, further comprising a needle assembly adapted for insertion into said injection port assembly, wherein said needle assembly has a first configuration in which an inflation lumen of said needle assembly is in fluid communication with said inflation chamber for selectively inflating and deflating said shell using the first fluid and a second configuration in which a drainage lumen of said needle assembly is in fluid communication with said drainage chamber for draining the second fluid from outside said shell.

4. The tissue expander as claimed in claim 3, wherein said needle assembly comprises:
a needle having an elongated shaft with a proximal end and a distal end, said needle including said inflation lumen located at the distal end of said elongated shaft that is aligned with said inflation chamber and said drainage lumen that is proximal to said inflation lumen that is aligned with said drainage chamber, wherein said barrier membrane isolates said inflation lumen from said drainage lumen;
an insert disposed inside said elongated shaft of said needle and being moveable between an extended position in which said inflation lumen is open and said drainage lumen is closed, and a retracted position in which said inflation lumen is closed and said drainage lumen is open.

5. The tissue expander as claimed in claim 4, wherein said insert of said needle assembly comprises an elongated shaft having a proximal end that is open, a distal end that is closed by a distal end wall, and an elongated conduit that extends from the proximal end to the distal end of said insert, said insert including a side port formed in an outer wall of said elongated shaft of said insert that is in communication with the elongated conduit of said insert, wherein said side port of said insert is in alignment with said inflation lumen of said needle when said insert is in the extended position and said side port of said insert is in alignment with said drainage lumen of said needle when said insert is in the retracted position.

6. The tissue expander as claimed in claim 1, further comprising:
said needle guard including a needle guard rim that extends upwardly from said needle guard base;
a barrier membrane support that projects from the top surface of said needle guard base toward the bottom surface of said barrier membrane for supporting an underside of said barrier membrane.

7. The tissue expander as claimed in claim 6, wherein said injection port assembly further comprises an injection dome secured to an upper end of said needle guard rim, wherein said injection dome comprises a base having a bottom surface with an annular groove formed therein, and wherein the upper end of said needle guard rim is disposed within said annular groove of said injection dome for securing said injection dome to said needle guard.

8. The tissue expander as claimed in claim 7, wherein said needle guard rim has a first height, and wherein said injection dome has a second height that is less than the first height of said needle guard rim.

9. The tissue expander as claimed in claim 7, wherein said needle guard rim has one or more assembly openings formed therein that are located adjacent the upper end of said needle guard rim, and wherein the one or more assembly openings are disposed within said annular groove of said injection dome.

10. The tissue expander as claimed in claim 9, further comprising a drainage port that passes through said needle guard rim for interconnecting said drainage chamber and said drainage conduit, and wherein said drainage port is located between the bottom surface of said base of said injection dome and said needle guard base.

11. The tissue expander as claimed in claim 10, further comprising silicone material overlying the upper end of said needle guard rim and in contact with the one or more assembly openings formed in said needle guard rim, wherein said silicone material secures said injection dome to the upper end of said needle guard rim.

12. The tissue expander as claimed in claim 10, wherein said drainage chamber is located between the bottom surface of said injection dome and the top surface of said barrier membrane.

13. The tissue expander as claimed in claim 12, wherein said one or more inflation ports pass through lateral openings provided in said needle guard rim, and wherein said one or more inflation ports are located between said drainage port and a top surface of said needle guard base.

14. The tissue expander as claimed in claim 1, wherein said drainage manifold comprises a drainage manifold port, and wherein the second end of said drainage conduit is secured to said drainage manifold port for connecting said drainage conduit to said drainage manifold.

15. The tissue expander as claimed in claim 14, wherein said drainage conduit comprises a one-way check valve that is configured to enable fluid passing through said drainage conduit to move in only one direction toward said drainage chamber of said injection port assembly.

16. The tissue expander as claimed in claim 15, wherein said drainage manifold has an inner face and an outer face, wherein said drainage manifold port projects from said inner face of said drainage manifold, and wherein said outer face of said drainage manifold is secured to an inner surface of said shell to form a water-tight seal between said drainage manifold and the inner surface of said shell.

17. The tissue expander as claimed in claim 16, wherein the inner face of said drainage manifold surrounds a trough, wherein said drain comprises one or more drains that are disposed in said trough and that are aligned with said one of more drainage holes formed in said shell, and wherein said drainage manifold port is in fluid communication with said trough and said one or more drains that are disposed within said trough.

18. The tissue expander as claimed in claim 1, further comprising:
    said drainage manifold having an inner face and an outer face, the outer face of said drainage manifold forming a water-tight seal with an inner surface of said shell and surrounding said one or more drainage openings formed in said shell;
    said drain including a sealed drain cover that is secured with the inner face of said drainage manifold, wherein the second end of said drainage conduit is coupled with said drainage manifold.

19. A tissue expander having an integrated drain comprising:
    a shell having an injection port opening and one or more drainage holes formed in said shell that are spaced from said injection port opening;
    an injection port assembly disposed in said injection port opening, wherein said injection port assembly forms a fluid-tight seal with said shell;
    said injection port assembly including a needle guard having a needle guard base with a top surface;
    a barrier membrane disposed within said needle guard that overlies the top surface of said needle guard base, wherein said barrier membrane defines an inflation chamber located between the top surface of said needle guard base and a bottom surface of said barrier membrane, and wherein said barrier membrane defines a drainage chamber located within said needle guard that overlies a top surface of said barrier membrane;
    one or more inflation ports in fluid communication with said inflation chamber for inflating and deflating said shell with a first fluid;
    a drainage conduit in fluid communication with and extending between said drainage chamber and said one or more drainage holes formed in said shell for draining a second fluid from outside said shell;
    an infusion chamber overlying the top surface of said barrier membrane and separated from said drainage chamber;
    an infusion conduit in fluid communication with and extending between said infusion chamber and at least one of said one or more drainage holes formed in said shell for delivering an infusion fluid to the outside said shell.

20. A tissue expander having an integrated drain comprising:
    a shell having an injection port opening and one or more drainage holes formed in said shell;
    an injection port assembly disposed in said injection port opening for forming a fluid-tight seal with said shell;
    said injection port assembly including a needle guard having a needle guard base with a top surface and a needle guard rim that extends upwardly from said needle guard base and that surrounds an outer perimeter of said needle guard base;
    a barrier membrane disposed within said needle guard that overlies the top surface of said needle guard base;
    said barrier membrane defining an inflation chamber located between the top surface of said needle guard base and a bottom surface of said barrier membrane for inflating and deflating said shell with a first fluid;
    said needle guard rim having one or more lateral openings that define one or more shell inflation ports that are in fluid communication with said inflation chamber;
    said barrier membrane defining a drainage chamber located within said needle guard that overlies a top surface of said barrier membrane for draining a second fluid from outside said shell through said one or more drainage holes;
    a needle assembly configured for insertion into said injection port assembly, wherein said needle assembly has a first configuration in which an inflation lumen of said needle assembly is in fluid communication with said inflation chamber for selectively inflating and deflating said shell using the first fluid and a second configuration in which a drainage lumen of said needle assembly is in fluid communication with said drainage chamber for draining the second fluid from outside said shell.

21. The tissue expander as claimed in claim 20, further comprising a barrier membrane support that projects from the top surface of said needle guard base toward the bottom surface of said barrier membrane.

22. The tissue expander as claimed in claim 20, further comprising:
    said injection port assembly including an injection dome secured to an upper end of said needle guard rim;
    said injection dome including a base having a bottom surface with an annular groove formed therein, wherein the upper end of said needle guard rim is disposed within said annular groove of said injection dome for securing said injection dome to said needle guard.

23. The tissue expander as claimed in claim 22, further comprising:
    said needle guard rim has one or more assembly openings formed therein that are located adjacent the upper end of said needle guard rim, wherein the one or more assembly openings are disposed within said annular groove of said injection dome; and
    silicone material overlying the upper end of said needle guard rim and in contact with the one or more assembly openings formed in said needle guard rim, wherein said silicone material secures said injection dome to the upper end of said needle guard rim.

24. A tissue expander having an integrated drain comprising:

a shell having an injection port opening and one or more drainage holes formed in said shell that are spaced from said injection port opening;

an injection port assembly disposed in said injection port opening, wherein said injection port assembly forms a fluid-tight seal with said shell;

said injection port assembly including a needle guard having a needle guard base with a top surface and a needle guard rim that extends upwardly from the top surface of said needle guard base;

a barrier membrane disposed within said needle guard that overlies the top surface of said needle guard base and that extends from one side of said needle guard rim to an opposite side of said needle guard rim, wherein said barrier membrane divides said injection port into an inflation chamber and a drainage chamber;

a barrier membrane support that projects from the top surface of said needle guard base toward the bottom surface of said barrier membrane, wherein said barrier membrane support is spaced inwardly from and is surrounded by said needle guard rim for supporting an underside of said barrier membrane;

one or more inflation ports in fluid communication with said inflation chamber for inflating and deflating said shell with a first fluid;

a drainage conduit in fluid communication with and extending between said drainage chamber and said one or more drainage holes formed in said shell for draining a second fluid from outside said shell.

* * * * *